(12) United States Patent
Ikegaya et al.

(10) Patent No.: US 6,620,961 B1
(45) Date of Patent: Sep. 16, 2003

(54) BIARYLALKYLENECARBAMIC ACID DERIVATIVES AND BACTERIOCIDES FOR AGRICULTURAL AND HORTICULTURAL USE

(75) Inventors: Kazuhiro Ikegaya, Shizuoka (JP); Masami Ozaki, Shizuoka (JP); Takahiro Kawashima, Shizuoka (JP); Ichiro Miura, Miyagi (JP); Norimichi Muramatsu, Shizuoka (JP)

(73) Assignees: Kumiai Chemical Industry Co., Ltd., Tokyo (JP); Ihara Chemical Industry Co. Ltd., Tokyo (JP)

( * ) Notice: Subject to any disclaimer, the term of this patent is extended or adjusted under 35 U.S.C. 154(b) by 0 days.

(21) Appl. No.: 09/485,689

(22) PCT Filed: Aug. 24, 1998

(86) PCT No.: PCT/JP98/03736

§ 371 (c)(1),
(2), (4) Date: Feb. 25, 2000

(87) PCT Pub. No.: WO99/10317

PCT Pub. Date: Mar. 4, 1999

(30) Foreign Application Priority Data

Aug. 26, 1997 (JP) ................................. 9-244559

(51) Int. Cl.$^7$ .................... C07C 261/00; C07C 273/00
(52) U.S. Cl. ......................... 560/29; 560/24; 560/30; 560/32; 564/56
(58) Field of Search ........................ 564/56; 560/24, 560/29, 30, 32

(56) References Cited

U.S. PATENT DOCUMENTS 5,808,151 A * 9/1998 Epperson et al. ............. 564/48

\* cited by examiner

*Primary Examiner*—Paul J. Killos
(74) *Attorney, Agent, or Firm*—Oblon, Spivak, McClelland, Maier & Neustadt, P.C.

(57) ABSTRACT

Biarylalkylenecarbamic acid derivative represented by general formula (I):

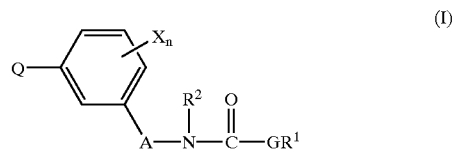

[wherein Q is a phenyl group which may be substituted or the like, X is a halogen atom, a ($C_1$–$C_6$) alkyl group or the like, n is 0 or an integer of from 1 to 4, $R^1$ is a ($C_1$–$C_6$) alkyl group or the like, $R^2$ is a hydrogen atom, a ($C_1$–$C_6$) alkyl group or the like, A is a ($C_1$–$C_7$) alkylene group which may be branched, and G is an oxygen atom, a sulfur atom or a group —NR— (wherein $R^3$ is a hydrogen atom or a ($C_1$–$C_4$) alkyl group)] and agricultural and horticultural fungicides.

The agricultural and horticultural fungicides of the present invention are useful as agricultural and horticultural fungicides because they have high preventive effects on cucumber downy mildew, apple scab, wheat powdery mildew, rice blast, cucumber gray mold and rice sheath blight without damaging crops, and are excellent in residual effectiveness and rain-resistance.

20 Claims, No Drawings

BIARYLALKYLENECARBAMIC ACID DERIVATIVES AND BACTERIOCIDES FOR AGRICULTURAL AND HORTICULTURAL USE

TECHNICAL FIELD

The present invention relates to novel biarylalkylenecarbamic acid derivatives and agricultural and horticultural fungicides containing them as active ingredients.

BACKGROUND ART

The biarylalkylenecarbamic acid derivatives as the compounds of the present invention have not been known to have excellent fungicidal activity although a number of carbamic acid derivatives have been reported so far.

The present inventors have conducted extensive research to develop novel agricultural and horticultural fungicides and have found out that the biarylalkylenecarbamic acid derivatives of the present invention (hereinafter referred to as the compounds of the present invention) are novel compounds which have not been reported in the literature and show remarkable effects as agricultural and horticultural fungicides. The present invention is accomplished on the basis of the discovery.

DISCLOSURE OF THE INVENTION

Namely, the present invention provides biarylalkylenecarbamic acid derivatives represented by general formula (I):

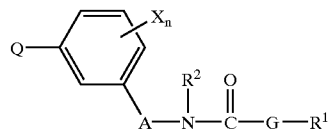

(I)

{wherein X is a halogen atom, a $(C_1-C_6)$ alkyl group, a $(C_1-C_6)$ alkoxy group, a $(C_1-C_4)$ haloalkyl group or a $(C_1-C_4)$ haloalkoxy group, n is 0 or an integer of from 1 to 4, $R^1$ is a $(C_1-C_6)$ alkyl group, a $(C_2-C_6)$ alkenyl group, a $(C_2-C_6)$ alkynyl group, a $(C_3-C_6)$ cycloalkyl group or a $(C_1-C_4)$ haloalkyl group, $R^2$ is a hydrogen atom, a $(C_1-C_6)$ alkyl group, a $(C_2-C_6)$ alkenyl group, a $(C_2-C_6)$ alkynyl group, a $(C_1-C_4)$ alkoxy group, a $(C_1-C_6)$ alkoxy $(C_1-C_4)$ alkyl group, a $(C_1-C_6)$ alkylthio $(C_1-C_4)$ alkyl group, a $(C_1-C_4)$ haloalkyl group, a $(C_1-C_6)$ alkylcarbonyl group, a phenylcarbonyl group, a $(C_1-C_4)$ alkoxycarbonyl group or an aryl $(C_1-C_4)$ alkyl group [which may be substituted with a halogen atom, a $(C_1-C_3)$ alkyl group or a $(C_1-C_3)$ alkoxy group], A is a $(C_1-C_7)$ alkylene group which may be branched, G is an oxygen atom, a sulfur atom or a group—NR— [wherein $R^3$ is a hydrogen atom or a $(C_1-C_4)$ alkyl group], and Q is a group represented by general formula:

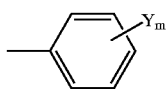

(A-1)

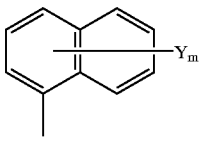

(A-2)

or

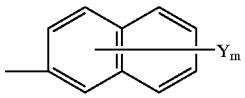

(A-3)

wherein Y is a halogen atom, nitro, cyano, hydroxy, a $(C_1-C_6)$ alkyl group, a $(C_2-C_6)$ alkenyl group, a $(C_2-C_6)$ alkynyl group, a $(C_3-C_6)$ cycloalkyl group, a $(C_3-C_6)$ cycloalkyl $(C_1-C_4)$ alkyl group, a $(C_1-C_6)$ alkoxy group, a $(C_2-C_6)$ alkenyloxy group, a $(C_2-C_6)$ alkynyloxy group, a $(C_3-C_6)$ cycloalkoxy group, a $(C_1-C_6)$ alkylthio group, a $(C_1-C_6)$ alkylsulfinyl group, a $(C_1-C_6)$ alkylsulfonyl group, a $(C_1-C_4)$ alkoxy $(C_1-C_4)$ alkyl group, a $(C_1-C_4)$ alkylthio $(C_1-C_4)$ alkyl group, a $(C_1-C_4)$ haloalkyl group, a $(C_1-C_4)$ haloalkoxy group, a $(C_1-C_4)$ haloalkylthio group, a $(C_1-C_4)$ haloalkylsulfinyl group, a $(C_1-C_4)$ haloalkylsulfonyl group, a $(C_1-C_4)$ alkylcarbonyl group, a $(C_1-C_4)$ alkoxycarbonyl group, a group —$CONR^4R^5$ [wherein $R^4$ and $R^5$ which may be the same or different, are hydrogen atoms or $(C_1-C_4)$ alkyl groups], an amino group, a mono$(C_1-C_4)$ alkylamino group, a di$(C_1-C_4)$ alkylamino group, a $(C_1-C_4)$ alkylcarbonylamino group, an aryl group [which may be substituted with a halogen atom, a $(C_{01}-C_4)$ alkyl group or a $(C_1-C_4)$ alkoxy group], an aryloxy group [which may be substituted with a halogen atom, a $(C_1-C_4)$ alkyl group or a $(C_1-C_4)$ alkoxy group], an aryl $(C_1-C_4)$ alkoxy group [which may be substituted with a halogen atom, a $(C_1-C_4)$ alkyl group or a $(C_1-C_4)$ alkoxy group], or may form a methylenedioxy group together with an adjacent Y, and m is 0 or an integer of from 1 to 5} and agricultural and horticultural fungicides containing them as active ingredients.

The symbols and terms used herein are explained below.

A halogen atom is a fluorine atom, a chlorine atom, a bromine atom or an iodine atom.

An expression such as $(C_1-C_6)$ means that the carbon number of the preceded group is, in this case, from 1 to 6.

A $(C_1-C_6)$ alkyl group is a linear or branched alkyl group such as methyl, ethyl, n-propyl, isopropyl, n-butyl, isobutyl, sec-butyl, tert-butyl, n-pentyl, isopentyl, neopentyl, n-hexyl, 3,3-dimethylbutyl or the like.

A $(C_3-C_6)$ cycloalkyl group is, for example, cyclopropyl, cyclopentyl, cyclohexyl or the like.

A $(C_1-C_4)$ haloalkyl group is a linear or branched alkyl group substituted with halogen atom(s) such as fluoromethyl, chloromethyl, difluoromethyl, dichloromethyl, trifluoromethyl, pentafluoroethyl or the like.

A $(C_2-C_6)$ alkenyl group is a linear or branched alkenyl group such as vinyl, 1-propenyl, 2-propenyl, isopropenyl, 1-butenyl, 2-butenyl or the like.

A $(C_2-C_6)$ alkynyl group is a linear or branched alkynyl group such as ethynyl, 1-propynyl, 2-propynyl, 1-butynyl, 2-butynyl, 3-butynyl, 4-methyl-1-pentynyl, 3-methyl-1-pentynyl or the like.

A $(C_1-C_6)$ alkoxy group is an alkyloxy group having such an alkyl moiety as mentioned above.

A $(C_2-C_6)$ alkenyloxy group is an alkenyloxy group having such an alkenyl moiety as mentioned above.

A $(C_2-C_6)$ alkynyloxy group is an alkynyloxy group having such an alkynyl moiety as mentioned above.

A (C₃–C₆) cycloalkoxy group is a cycloalkyloxy group having such a cycloalkyl moiety as mentioned above.

A (C₁–C₄) haloalkoxy group is a haloalkyloxy group having such a haloalkyl moiety as mentioned above.

A (C₁–C₆) alkylthio group is an alkylthio group having such an alkyl moiety as mentioned above.

A (C₁–C₆) alkylsulfinyl group is an alkylsulfinyl group having such an alkyl moiety as mentioned above.

A (C₁–C₆) alkylsulfonyl group is an alkylsulfonyl group having such an alkyl moiety as mentioned above.

A (C₁–C₄) haloalkylthio group is a haloalkylthio group having such a haloalkyl moiety as mentioned above.

A (C₁–C₄) haloalkylsulfinyl group is a haloalkylsulfinyl group having such a haloalkyl moiety as mentioned above.

A (C₁–C₄) haloalkylsulfonyl group is a haloalkylsulfonyl group having such a haloalkyl moiety as mentioned above.

A (C₁–C₇) alkylene group which may be branched is, for example, —CH₂—, —CH(CH₃)—, —C(CH₃)₂—, —CH₂CH₂—, —CH₂CH₂CH₂— or the like.

An aryl group is phenyl, α-naphthyl, β-naphthyl or the like.

An aryl (C₁–C₄) alkyl group is benzyl or the like.

An aryloxy group is phenoxy, naphthoxy or the like.

An aryl (C₁–C₄) alkoxy group is benzyloxy or the like.

Specific examples of the compounds of the present invention are given below in Tables 1 to 53. However, the compounds of the present invention are by no means restricted to those specific examples. The compound Nos. are referred to in the description hereinafter.

TABLE 1

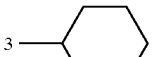

| Comp. No. | Ym | G | R¹ | R² | m.p. (° C.) |
|---|---|---|---|---|---|
| 1-1 | H | O | CH₃ | H | 49–52 |
| 1-2 | 2-Cl | O | CH₃ | H | oily |
| 1-3 | 3-Cl | O | CH₃ | H | oily |
| 1-4 | 4-Cl | O | CH₃ | H | 85–88 |
| 1-5 | 2-F | O | CH₃ | H | |
| 1-6 | 3-F | O | CH₃ | H | oily |
| 1-7 | 4-F | O | CH₃ | H | 60–61 |
| 1-8 | 3-Br | O | CH₃ | H | |
| 1-9 | 4-Br | O | CH₃ | H | 126–129 |
| 1-10 | 2-CH₃ | O | CH₃ | H | oily |
| 1-11 | 3-CH₃ | O | CH₃ | H | oily |
| 1-12 | 4-CH₃ | O | CH₃ | H | 64–67 |
| 1-13 | 3-C₂H₅ | O | CH₃ | H | oily |
| 1-14 | 4-C₂H₅ | O | CH₃ | H | 57–58 |
| 1-15 | 3-C₃H₇ | O | CH₃ | H | |
| 1-16 | 4-C₃H₇ | O | CH₃ | H | |
| 1-17 | 3-C₃H₇-i | O | CH₃ | H | oily |
| 1-18 | 4-C₃H₇-i | O | CH₃ | H | 46–48 |
| 1-19 | 3-C₄H₉-t | O | CH₃ | H | |
| 1-20 | 4-C₄H₉-t | O | CH₃ | H | |
| 1-21 | 3-C₆H₁₃ | O | CH₃ | H | |
| 1-22 | 4-C₆H₁₃ | O | CH₃ | H | |
| 1-23 | 3-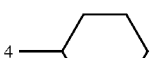 | O | CH₃ | H | |
| 1-24 | 4- | O | CH₃ | H | |

TABLE 1-continued

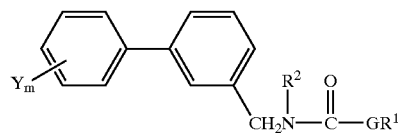

| Comp. No. | Ym | G | R¹ | R² | m.p. (° C.) |
|---|---|---|---|---|---|
| 1-25 | 3- | O | CH₃ | H | |
| 1-26 | 4- | O | CH₃ | H | |
| 1-27 | 3-—CH₂CH₂-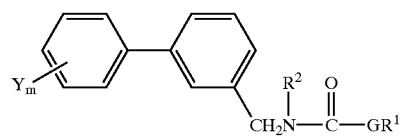 | O | CH₃ | H | |
| 1-28 | 4-—CH₂CH₂-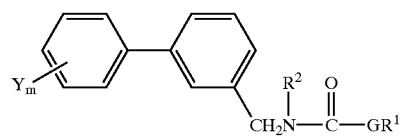 | O | CH₃ | H | |

TABLE 2

| Comp. No. | Ym | G | R¹ | R² | m.p. (° C.) |
|---|---|---|---|---|---|
| 1-29 | 3-CH=CH₂ | O | CH₃ | H | |
| 1-30 | 4-CH=CH₂ | O | CH₃ | H | |
| 1-31 | 3-C≡CHCH₃ | O | CH₃ | H | |
| 1-32 | 4-C≡CHCH₃ | O | CH₃ | H | |
| 1-33 | 2-CF₃ | O | CH₃ | H | 61–64 |
| 1-34 | 3-CF₃ | O | CH₃ | H | oily |
| 1-35 | 4-CF₃ | O | CH₃ | H | 94–95 |
| 1-36 | 3-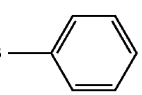 | O | CH₃ | H | |
| 1-37 | 4-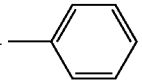 | O | CH₃ | H | |
| 1-38 | 3-OH | O | CH₃ | H | |
| 1-39 | 4-OH | O | CH₃ | H | |
| 1-40 | 2-OCH₃ | O | CH₃ | H | oily |
| 1-41 | 3-OCH₃ | O | CH₃ | H | oily |
| 1-42 | 4-OCH₃ | O | CH₃ | H | 93–95 |
| 1-43 | 3-OC₂H₅ | O | CH₃ | H | |
| 1-44 | 4-OC₂H₅ | O | CH₃ | H | |
| 1-45 | 3-OC₃H₇-i | O | CH₃ | H | |
| 1-46 | 4-OC₃H₇-i | O | CH₃ | H | |
| 1-47 | 3-—O-phenyl | O | CH₃ | H | |
| 1-48 | 4-—O-phenyl | O | CH₃ | H | |

TABLE 2-continued

| Comp. No. | Ym | G | R¹ | R² | m.p. (° C.) |
|---|---|---|---|---|---|
| 1-49 | 3-O-(2-chlorophenyl) | O | CH₃ | H | |
| 1-50 | 4-O-(2-chlorophenyl) | O | CH₃ | H | |
| 1-51 | 3-O-(2-methylphenyl) | O | CH₃ | H | |
| 1-52 | 4-O-(2-methylphenyl) | O | CH₃ | H | |
| 1-53 | 3-O-(2-methoxyphenyl) | O | CH₃ | H | |
| 1-54 | 4-O-(2-methoxyphenyl) | O | CH₃ | H | |

TABLE 3

| Comp. No. | Ym | G | R¹ | R² | m.p. (° C.) |
|---|---|---|---|---|---|
| 1-55 | 3-OCH₂-phenyl | O | CH₃ | H | |
| 1-56 | 4-OCH₂-phenyl | O | CH₃ | H | |
| 1-57 | 3-OCH₂-(2-methoxyphenyl) | O | CH₃ | H | |
| 1-58 | 4-OCH₂-(2-methoxyphenyl) | O | CH₃ | H | |
| 1-59 | 3-OCH₂-(2-chlorophenyl) | O | CH₃ | H | |
| 1-60 | 4-OCH₂-(2-chlorophenyl) | O | CH₃ | H | |
| 1-61 | 3-O-cyclopentyl | O | CH₃ | H | |
| 1-62 | 4-O-cyclopentyl | O | CH₃ | H | |
| 1-63 | 3-OCH₂CH=CH₂ | O | CH₃ | H | |
| 1-64 | 4-OCH₂CH=CH₂ | O | CH₃ | H | |
| 1-65 | 3-OCH₂C≡CH | O | CH₃ | H | |
| 1-66 | 4-OCH₂C≡CH | O | CH₃ | H | |
| 1-67 | 3-CH₂OCH₃ | O | CH₃ | H | |
| 1-68 | 4-CH₂OCH₃ | O | CH₃ | H | |
| 1-69 | 3-CH₂OC₂H₅ | O | CH₃ | H | |
| 1-70 | 4-CH₂OC₂H₅ | O | CH₃ | H | |
| 1-71 | 3-OCF₃ | O | CH₃ | H | oily |
| 1-72 | 4-OCF₃ | O | CH₃ | H | 51–54 |
| 1-73 | 3-OCHF₂ | O | CH₃ | H | |
| 1-74 | 4-OCHF₂ | O | CH₃ | H | |
| 1-75 | 3-SCH₃ | G | CH₃ | H | |
| 1-76 | 4-SCH₃ | O | CH₃ | H | |
| 1-77 | 3-SOCH₃ | O | CH₃ | H | |
| 1-78 | 4-SOCH₃ | O | CH₃ | H | |
| 1-79 | 3-SO₂CH₃ | O | CH₃ | H | |

TABLE 4

| Comp. No. | Ym | G | R¹ | R² | m.p. (° C.) |
|---|---|---|---|---|---|
| 1-80 | 4-SO₂CH₃ | O | CH₃ | H | |
| 1-81 | 3-CH₂SCH₃ | O | CH₃ | H | |
| 1-82 | 4-CH₂SCH₃ | O | CH₃ | H | |
| 1-83 | 3-SCHF₂ | O | CH₃ | H | |
| 1-84 | 4-SCHF₂ | O | CH₃ | H | |
| 1-85 | 3-SOCHF₂ | O | CH₃ | H | |
| 1-86 | 4-SOCHF₂ | O | CH₃ | H | |
| 1-87 | 3-SCF₃ | O | CH₃ | H | |
| 1-88 | 4-SCF₃ | O | CH₃ | H | |
| 1-89 | 3-SOCF₃ | O | CH₃ | H | |
| 1-90 | 4-SOCF₃ | O | CH₃ | H | |
| 1-91 | 3-SO₂CF₃ | O | CH₃ | H | |
| 1-92 | 4-SO₂CF₃ | O | CH₃ | H | |
| 1-93 | 3-COCH₃ | O | CH₃ | H | 92–93 |
| 1-94 | 4-COCH₃ | O | CH₃ | H | 103–104 |
| 1-95 | 3-COOCH₃ | O | CH₃ | H | |
| 1-96 | 4-COOCH₃ | O | CH₃ | H | |
| 1-97 | 3-COOC₂H₅ | O | CH₃ | H | |
| 1-98 | 4-COOC₂H₅ | O | CH₃ | H | |
| 1-99 | 3-CONH₂ | O | CH₃ | H | |
| 1-100 | 4-CONH₂ | O | CH₃ | H | |
| 1-101 | 3-CON(CH₃)₂ | O | CH₃ | H | |
| 1-102 | 4-CON(CH₃)₂ | O | CH₃ | H | |
| 1-103 | 3-NO₂ | O | CH₃ | H | 79–82 |
| 1-104 | 4-NO₂ | O | CH₃ | H | |
| 1-105 | 3-CN | O | CH₃ | H | |

TABLE 4-continued

| Comp. No. | Ym | G | $R^1$ | $R^2$ | m.p. (° C.) |
|---|---|---|---|---|---|
| 1-106 | 4-CN | O | $CH_3$ | H | |
| 1-107 | 3-$NH_2$ | O | $CH_3$ | H | |
| 1-108 | 4-$NH_2$ | O | $CH_3$ | H | |
| 1-109 | 3-$NHCH_3$ | O | $CH_3$ | H | |
| 1-110 | 4-$NHCH_3$ | O | $CH_3$ | H | |
| 1-111 | 3-$N(CH_3)_2$ | O | $CH_3$ | H | |

TABLE 5

| Comp. No. | Ym | G | $R^1$ | $R^2$ | m.p. (° C.) |
|---|---|---|---|---|---|
| 1-112 | 4-$N(CH_3)_2$ | O | $CH_3$ | H | |
| 1-113 | 3-$NHCOCH_3$ | O | $CH_3$ | H | |
| 1-114 | 4-$NHCOCH_3$ | O | $CH_3$ | H | |
| 1-115 | 3-$NHCOC_2H_5$ | O | $CH_3$ | H | |
| 1-116 | 4-$NHCOC_2H_5$ | O | $CH_3$ | H | |
| 1-117 | 2,4-$Cl_2$ | O | $CH_3$ | H | 77–80 |
| 1-118 | 3,4-$Cl_2$ | O | $CH_3$ | H | oily |
| 1-119 | 3,5-$Cl_2$ | O | $CH_3$ | H | oily |
| 1-120 | 3,4-$F_2$ | O | $CH_3$ | H | 40–43 |
| 1-121 | 3,5-$F_2$ | O | $CH_3$ | H | |
| 1-122 | 3-Cl, 4-F | O | $CH_3$ | H | 60–61 |
| 1-123 | 2,4-$(CH_3)_2$ | O | $CH_3$ | H | |
| 1-124 | 3,5-$(CH_3)_2$ | O | $CH_3$ | H | |
| 1-125 | 3,4-$(CH_3)_2$ | O | $CH_3$ | H | oily |
| 1-126 | 2,4-$(OCH_3)_2$ | O | $CH_3$ | H | |
| 1-127 | 3,4-$(OCH_3)_2$ | O | $CH_3$ | H | |
| 1-128 | 3.5-$(OCH_3)_2$ | O | $CH_3$ | H | |
| 1-129 | 3-F, 4-$CH_3$ | O | $CH_3$ | H | |
| 1-130 | 3-Cl, 4-$CH_3$ | O | $CH_3$ | H | |
| 1-131 | 3-$CH_3$, 4-F | O | $CH_3$ | H | |
| 1-132 | 3-$CH_3$, 4-Cl | O | $CH_3$ | H | |
| 1-133 | 3-$CH_3$, 4-Br | O | $CH_3$ | H | |
| 1-134 | 4-Cl, 3-$OCH_3$ | O | $CH_3$ | H | |
| 1-135 | 4-Cl, 3-$OC_2H_5$ | O | $CH_3$ | H | |
| 1-136 | 3,5-$(CH_3)_2$, 4-F | O | $CH_3$ | H | |
| 1-137 | 3-$NO_2$, 4-$CH_3$ | O | $CH_3$ | H | 82–83 |
| 1-138 | 3,5-$(CF_3)_2$ | O | $CH_3$ | H | |
| 1-139 | 2,4-$(CF_3)_2$ | O | $CH_3$ | H | |
| 1-140 | 2-$OCH_3$, 5-Br | O | $CH_3$ | H | |
| 1-141 | 2-F, 4-$CF_3$ | O | $CH_3$ | H | |
| 1-142 | 3,4-$(OCH_2O)$ | O | $CH_3$ | H | |
| 1-143 | 3,4,5-$Cl_3$ | O | $CH_3$ | H | |

TABLE 6

| Comp. No. | Ym | G | $R^1$ | $R^2$ | m.p. (° C.) |
|---|---|---|---|---|---|
| 1-144 | 3,5-$F_2$, 4-Cl | O | $CH_3$ | H | |
| 1-145 | 2,4,6-$(CH_3)_3$ | O | $CH_3$ | H | 89–91 |
| 1-146 | H | O | $C_2H_5$ | H | oily |
| 1-147 | H | O | $C_3H_7$ | H | oily |
| 1-148 | H | O | $C_4H_9$ | H | oily |
| 1-149 | H | O | $C_5H_{11}$ | H | |
| 1-150 | H | O | $C_3H_7$-i | H | 61–64 |
| 1-151 | H | O | $CH_2CH=CH_2$ | H | |
| 1-152 | H | O | $CH_2C\equiv CH$ | H | |
| 1-153 | H | O |  | H | |
| 1-154 | 3-$CH_3$ | O |  | H | |
| 1-155 | 4-$CH_3$ | O |  | H | |

TABLE 6-continued

| Comp. No. | Ym | G | $R^1$ | $R^2$ | m.p. (° C.) |
|---|---|---|---|---|---|
| 1-156 | H | O | 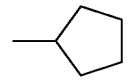 | H | |
| 1-157 | H | O | $CH_2Cl$ | H | |
| 1-158 | 3-$CH_3$ | O | $CH_2Cl$ | H | |
| 1-159 | 4-$CH_3$ | O | $CH_2Cl$ | H | |
| 1-160 | H | O | $CH_2CF_3$ | H | |
| 1-161 | 3-$CH_3$ | O | $CH_2CF_3$ | H | |
| 1-162 | 4-$CH_3$ | O | $CH_2CF_3$ | H | |
| 1-163 | H | O | $CH_3$ | $CH_3$ | oily |
| 1-164 | H | O | $C_2H_5$ | $CH_3$ | |
| 1-165 | H | O | $CH_3$ | $C_2H_5$ | oily |
| 1-166 | H | O | $CH_3$ | $C_3H_7$ | oily |
| 1-167 | H | O | $CH_3$ | $C_4H_9$ | |
| 1-168 | H | O | $CH_3$ | $CH_2CH=CH_2$ | oily |
| 1-169 | 3-$CH_3$ | O | $CH_3$ | $CH_2CH=CH_2$ | |
| 1-170 | 4-$CH_3$ | C | $CH_3$ | $CH_2CH=CH_2$ | |
| 1-171 | 3-F | O | $CH_3$ | $CH_2CH=CH_2$ | |
| 1-172 | 4-F | O | $CH_3$ | $CH_2CH=CH_2$ | |
| 1-173 | 2-Cl | O | $CH_3$ | $CH_2CH=CH_2$ | |
| 1-174 | 3-Cl | O | $CH_3$ | $CH_2CH=CH_2$ | |

TABLE 7

| Comp. No. | Ym | G | $R^1$ | $R^2$ | m.p. (° C.) |
|---|---|---|---|---|---|
| 1-175 | 4-Cl | O | $CH_3$ | $CH_2CH=CH_2$ | |
| 1-176 | 3-$CF_3$ | O | $CH_3$ | $CH_2CH=CH_2$ | |
| 1-177 | 4-$CF_3$ | O | $CH_3$ | $CH_2CH=CH_2$ | |
| 1-178 | H | O | $CH_3$ | $CH_2C\equiv CH$ | oily |
| 1-179 | 3-$CH_3$ | O | $CH_3$ | $CH_2C\equiv CH$ | |
| 1-180 | 4-$CH_3$ | O | $CH_3$ | $CH_2C\equiv CH$ | |
| 1-181 | 2-Cl | O | $CH_3$ | $CH_2C\equiv CH$ | |
| 1-182 | 3-Cl | O | $CH_3$ | $CH_2C\equiv CH$ | |
| 1-183 | 4-Cl | O | $CH_3$ | $CH_2C\equiv CH$ | |
| 1-184 | 3-$CF_3$ | O | $CH_3$ | $CH_2C\equiv CH$ | |
| 1-185 | 4-$CF_3$ | O | $CH_3$ | $CH_2C\equiv CH$ | |
| 1-186 | H | O | $C_2H_5$ | $CH_2C\equiv CH$ | |
| 1-187 | H | O | $CH_3$ | $CH_2CF_3$ | |
| 1-188 | H | O | $CH_3$ | 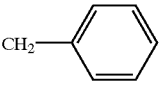 | oily |
| 1-189 | H | O | $CH_3$ |  | |
| 1-190 | H | O | $CH_3$ |  | |
| 1-191 | H | O | $CH_3$ | 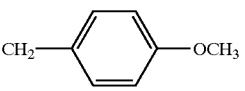 | |
| 1-192 | H | O | $CH_3$ | $CH_2OCH_3$ | oily |
| 1-193 | 2-$CH_3$ | O | $CH_3$ | $CH_2OCH_3$ | oily |
| 1-194 | 3-$CH_3$ | O | $CH_3$ | $CH_2OCH_3$ | oily |
| 1-195 | 4-$CH_3$ | O | $CH_3$ | $CH_2OCH_3$ | oily |
| 1-196 | 2-$OCH_3$ | O | $CH_3$ | $CH_2OCH_3$ | |
| i-197 | 3-$OCH_3$ | O | $CH_3$ | $CH_2OCH_3$ | |
| 1-198 | 4-$OCH_3$ | O | $CH_3$ | $CH_2OCH_3$ | oily |
| 1-199 | 2-F | O | $CH_3$ | $CH_2OCH_3$ | |
| 1-200 | 3-F | O | $CH_3$ | $CH_2OCH_3$ | |

TABLE 7-continued

| Comp. No. | Ym | G | R¹ | R² | m.p. (° C.) |
|---|---|---|---|---|---|
| 1-201 | 4-F | O | CH₃ | CH₂OCH₃ | oily |
| 1-202 | 2-Cl | O | CH₃ | CH₂OCH₃ | oily |

TABLE 8

| Comp. No. | Ym | G | R¹ | R² | m.p. (° C.) |
|---|---|---|---|---|---|
| 1-203 | 3-Cl | O | CH₃ | CH₂OCH₃ | |
| 1-204 | 4-Cl | O | CH₃ | CH₂OCH₃ | |
| 1-205 | 3-CF₃ | O | CH₃ | CH₂OCH₃ | |
| 1-206 | 4-CF₃ | O | CH₃ | CH₂OCH₃ | |
| 1-207 | 3,4-(CH₃)₂ | O | CH₃ | CH₂OCH₃ | |
| 1-208 | 3,4-Cl₂ | O | CH₃ | CH₂OCH₃ | |
| 1-209 | H | O | CH₃ | CH₂OC₂H₅ | |
| 1-210 | 3-Cl | O | CH₃ | CH₂OC₂H₅ | |
| 1-211 | 4-Cl | O | CH₃ | CH₂OC₂H₅ | |
| 1-212 | 3-CH₃ | O | CH₃ | CH₂OC₂H₅ | |
| 1-213 | 4-CH₃ | O | CH₃ | CH₂OC₂H₅ | |
| 1-214 | H | O | CH₃ | CH₂SCH₃ | |
| 1-215 | 2-CH₃ | O | CH₃ | CH₂SCH₃ | |
| 1-216 | 3-CH₃ | O | CH₃ | CH₂SCH₃ | |
| 1-217 | 4-CH₃ | O | CH₃ | CH₂SCH₃ | |
| 1-218 | 2-OCH₃ | O | CH₃ | CH₂SCH₃ | |
| 1-219 | 3-OCH₃ | O | CH₃ | CH₂SCH₃ | |
| 1-220 | 4-OCH₃ | O | CH₃ | CH₂SCH₃ | |
| 1-221 | 2-F | O | CH₃ | CH₂SCH₃ | |
| 1-222 | 3-F | O | CH₃ | CH₂SCH₃ | |
| 1-223 | 4-F | O | CH₃ | CH₂SCH₃ | |
| 1-224 | 2-Cl | O | CH₃ | CH₂SCH₃ | |
| 1-225 | 3-Cl | O | CH₃ | CH₂SCH₃ | |
| 1-226 | 4-Cl | O | CH₃ | CH₂SCH₃ | |
| 1-227 | 3-CF₃ | O | CH₃ | CH₂SCH₃ | |
| 1-228 | 4-CF₃ | O | CH₃ | CH₂SCH₃ | |
| 1-229 | 3,4-(CH₃)₂ | O | CH₃ | CH₂SCH₃ | |
| 1-230 | 3,4-Cl₂ | O | CH₃ | CH₂SCH₃ | |
| 1-231 | H | O | CH₃ | COCH₃ | oily |
| 1-232 | H | O | CH₃ | COC₂H₅ | |
| 1-233 | H | O | CH₃ | COC₄H₉ | |
| 1-234 | H | O | CH₃ | CO-C₆H₅ | |

TABLE 9

| Comp. No. | Ym | G | R¹ | R² | m.p. (° C.) |
|---|---|---|---|---|---|
| 1-235 | 3-CH₃ | O | CH₃ | COCH₃ | |
| 1-236 | 4-CH₃ | O | CH₃ | COCH₃ | |
| 1-237 | 2-Cl | O | CH₃ | COCH₃ | |
| 1-238 | 3-Cl | O | CH₃ | COCH₃ | |
| 1-239 | 4-Cl | O | CH₃ | COCH₃ | |
| 1-240 | 3-CF₃ | O | CH₃ | COCH₃ | |
| 1-241 | 4-CF₃ | O | CH₃ | COCH₃ | |
| 1-242 | 3,4-(CH₃)₂ | C | CH₃ | COCH₃ | |
| 1-243 | H | O | CH₃ | COOCH₃ | |
| 1-244 | H | O | CH₃ | COOC₂H₅ | |
| 1-245 | H | S | CH₃ | H | 85–88 |
| 1-246 | 3-CH₃ | S | CH₃ | H | |
| 1-247 | 4-CH₃ | S | CH₃ | H | 105–107 |
| 1-248 | 2-Cl | S | CH₃ | H | |
| 1-249 | 3-Cl | S | CH₃ | H | |
| 1-250 | 4-Cl | S | CH₃ | H | |
| 1-251 | 3-CF₃ | S | CH₃ | H | |
| 1-252 | 4-CF₃ | S | CH₃ | H | |
| 1-253 | H | NH | CH₃ | H | 115–118 |
| 1-254 | 3-CH₃ | NH | CH₃ | H | 148–151 |
| 1-255 | 4-CH₃ | NH | CH₃ | H | |
| 1-256 | 3-Cl | NH | CH₃ | H | |
| 1-257 | 4-Cl | NH | CH₃ | H | |
| 1-258 | 3-CF₃ | NH | CH₃ | H | |
| 1-259 | 4-CF₃ | NH | CH₃ | H | |
| 1-260 | H | NH | C₂H₅ | H | 136–137 |
| 1-261 | H | NH | C₃H₇ | H | |
| 1-262 | H | NCH₃ | CH₃ | H | oily |
| 1-263 | H | NC₂H₅ | C₂H₅ | H | |
| 1-264 | H | O | CH₃ | OCH₃ | oily |
| 1-265 | 2-CH₃ | O | CH₃ | OCH₃ | |
| 1-266 | 3-CH₃ | O | CH₃ | OCH₃ | oily |

TABLE 10

| Comp. No. | Ym | G | R¹ | R² | m.p. (° C.) |
|---|---|---|---|---|---|
| 1-267 | 4-CH₃ | O | CH₃ | OCH₃ | |
| 1-268 | 2-OCH₃ | O | CH₃ | OCH₃ | |
| 1-269 | 3-OCH₃ | O | CH₃ | OCH₃ | |
| 1-270 | 4-OCH₃ | O | CH₃ | OCH₃ | |
| 1-271 | 2-F | O | CH₃ | OCH₃ | |
| 1-272 | 3-F | O | CH₃ | OCH₃ | |
| 1-273 | 4-F | O | CH₃ | OCH₃ | |
| 1-274 | 2-Cl | O | CH₃ | OCH₃ | |
| 1-275 | 3-Cl | O | CH₃ | OCH₃ | oily |
| 1-276 | 4-Cl | O | CH₃ | OCH₃ | |
| 1-277 | 3-CF₃ | O | CH₃ | OCH₃ | oily |
| 1-278 | 4-CF₃ | O | CH₃ | OCH₃ | |
| 1-279 | 3,4-(CH₃)₂ | O | CH₃ | OCH₃ | |
| 1-280 | 3,4-Cl₂ | O | CH₃ | OCH₃ | |
| 1-281 | H | O | CH₃ | OC₂H₅ | |
| 1-282 | 2-CH₃ | O | CH₃ | OC₂H₅ | |
| 1-283 | 3-CH₃ | O | CH₃ | OC₂H₅ | |
| 1-284 | 4-CH₃ | O | CH₃ | OC₂H₅ | |
| 1-285 | 2-OCH₃ | O | CH₃ | OC₂H₅ | |
| 1-286 | 3-OCH₃ | O | CH₃ | OC₂H₅ | |
| 1-287 | 4-OCH₃ | O | CH₃ | OC₂H₅ | |
| 1-288 | 2-F | O | CH₃ | OC₂H₅ | |
| 1-289 | 3-F | O | CH₃ | OC₂H₅ | |
| 1-290 | 4-F | O | CH₃ | OC₂H₅ | |
| 1-291 | 2-Cl | O | CH₃ | OC₂H₅ | |
| 1-292 | 3-Cl | O | CH₃ | OC₂H₅ | |
| 1-293 | 4-Cl | O | CH₃ | OC₂H₅ | |
| 1-294 | 3-CF₃ | O | CH₃ | OC₂H₅ | |
| 1-295 | 4-CF₃ | O | CH₃ | OC₂H₅ | |
| 1-298 | 3,4-(CH₃)₂ | O | CH₃ | OC₂H₅ | |
| 1-297 | 3,4-Cl₂ | O | CH₃ | OC₂H₅ | |
| 1-298 | 4-C₆H₅ | O | CH₃ | H | 134–136 |

TABLE 11

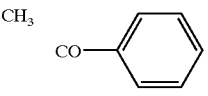

| Comp. No. | Ym | X¹ | X² | X³ | X⁴ | m.p. (° C.) |
|---|---|---|---|---|---|---|
| 2-1 | H | CH₃ | H | H | H | 91–94 |
| 2-2 | 3-F | CH₃ | H | H | H | |
| 2-3 | 4-F | CH₃ | H | H | H | |

TABLE 11-continued

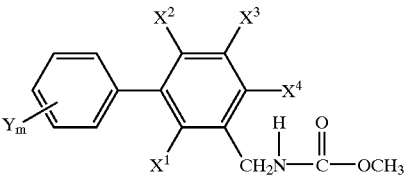

| Comp. No. | Ym | X¹ | X² | X³ | X⁴ | m.p. (° C.) |
|---|---|---|---|---|---|---|
| 2-4 | 3-Cl | CH₃ | H | H | H | |
| 2-5 | 4-Cl | CH₃ | H | H | H | |
| 2-6 | 3-CH₃ | CH₃ | H | H | H | |
| 2-7 | 4-CH₃ | CH₃ | H | H | H | |
| 2-8 | 3-C₂H₅ | CH₃ | H | H | H | |
| 2-9 | 4-C₂H₅ | CH₃ | H | H | H | |
| 2-10 | 3-OCH₃ | CH₃ | H | H | H | |
| 2-11 | 4-OCH₃ | CH₃ | H | H | H | |
| 2-12 | 3,4-(CH₃)₂ | CH₃ | H | H | H | |
| 2-13 | 3,5-(CH₃)₂ | CH₃ | H | H | H | |
| 2-14 | 2,4-Cl₂ | CH₃ | H | H | H | |
| 2-15 | 3,4-Cl₂ | CH₃ | H | H | H | |
| 2-16 | 3,5-Cl₂ | CH₃ | H | H | H | |
| 2-17 | H | H | F | H | H | 66–69 |
| 2-18 | 3-F | H | F | H | H | |
| 2-19 | 4-F | H | F | H | H | |
| 2-20 | 3-Cl | H | F | H | H | |
| 2-21 | 4-Cl | H | F | H | H | 87–90 |
| 2-22 | 3-CH₃ | H | F | H | H | oily |
| 2-23 | 4-CH₃ | H | F | H | H | |
| 2-24 | 3-C₂H₅ | H | F | H | H | |
| 2-25 | 4-C₂H₅ | H | F | H | H | |
| 2-26 | 3-OCH₃ | H | F | H | H | |
| 2-27 | 4-OCH₃ | H | F | H | H | |
| 2-28 | 3-CF₃ | H | F | H | H | |

TABLE 12

| Comp. No. | Ym | X¹ | X² | X³ | X⁴ | m.p. (° C.) |
|---|---|---|---|---|---|---|
| 2-29 | 4-CF₃ | H | F | H | H | |
| 2-30 | 2,4-Cl₂ | H | F | H | H | |
| 2-31 | 3,4-Cl₂ | H | F | H | H | |
| 2-32 | 3,4-(CH₃)₂ | H | F | H | H | |
| 2-33 | 3,5-(CH₃)₂ | H | F | H | H | |
| 2-34 | H | H | Cl | H | H | |
| 2-35 | 3-F | H | Cl | H | H | |
| 2-36 | 4-F | H | Cl | H | H | |
| 2-37 | 3-Cl | H | Cl | H | H | |
| 2-38 | 4-Cl | H | Cl | H | H | |
| 2-39 | 3-CH₃ | H | Cl | H | H | |
| 2-40 | 4-CH₃ | H | Cl | H | H | |
| 2-41 | 3-C₂H₅ | H | Cl | H | H | |
| 2-42 | 4-C₂H₅ | H | Cl | H | H | |
| 2-43 | 3-OCH₃ | H | Cl | H | H | |
| 2-44 | 4-OCH₃ | H | Cl | H | H | |
| 2-45 | 3-CF₃ | H | Cl | H | H | |
| 2-46 | 4-CF₃ | H | Cl | H | H | |
| 2-47 | 3,4-Cl₂ | H | Cl | H | H | |
| 2-48 | 3,4-(CH₃)₂ | H | Cl | H | H | |
| 2-49 | 3,5-(CH₃)₂ | H | Cl | H | H | |
| 2-50 | H | H | CH₃ | H | H | 67–70 |
| 2-51 | 3-F | H | CH₃ | H | H | |
| 2-52 | 4-F | H | CH₃ | H | H | |
| 2-53 | 3-Cl | H | CH₃ | H | H | |
| 2-54 | 4-Cl | H | CH₃ | H | H | 111–114 |
| 2-55 | 3-CH₃ | H | CH₃ | H | H | |
| 2-56 | 4-CH₃ | H | CH₃ | H | H | 91–94 |
| 2-57 | 3-C₂H₅ | H | CH₃ | H | H | |
| 2-58 | 4-C₂H₅ | H | CH₃ | H | H | |
| 2-59 | 4-OCH₃ | H | CH₃ | H | H | |

TABLE 13

| Comp. No. | Ym | X¹ | X² | X³ | X⁴ | m.p. (° C.) |
|---|---|---|---|---|---|---|
| 2-60 | 3-CF₃ | H | CH₃ | H | H | |
| 2-61 | 4-CF₃ | H | CH₃ | H | H | |
| 2-62 | 3,4-Cl₂ | H | CH₃ | H | H | |
| 2-63 | 3,4-(CH₃)₂ | H | CH₃ | H | H | |
| 2-64 | 3,5-(CH₃)₂ | H | CH₃ | H | H | |
| 2-65 | H | H | OCH₃ | H | H | 70–73 |
| 2-66 | 3-F | H | OCH₃ | H | H | |
| 2-67 | 4-F | H | OCH₃ | H | H | |
| 2-68 | 3-Cl | H | OCH₃ | H | H | |
| 2-69 | 4-Cl | H | OCH₃ | H | H | |
| 2-70 | 3-CH₃ | H | OCH₃ | H | H | |
| 2-71 | 4-CH₃ | H | OCH₃ | H | H | 73–76 |
| 2-72 | 3-C₂H₅ | H | OCH₃ | H | H | |
| 2-73 | 4-C₂H₅ | H | OCH₃ | H | H | |
| 2-74 | 4-OCH₃ | H | OCH₃ | H | H | |
| 2-75 | 3-CF₃ | H | OCH₃ | H | H | |
| 2-76 | 4-CF₃ | H | OCH₃ | H | H | |
| 2-77 | 3,4-Cl₂ | H | OCH₃ | H | H | |
| 2-78 | 3,4-(CH₃)₂ | H | OCH₃ | H | H | |
| 2-79 | 3,5-(CH₃)₂ | H | OCH₃ | H | H | |
| 2-80 | H | H | H | Cl | H | |
| 2-81 | 3-F | H | H | Cl | H | |
| 2-82 | 4-F | H | H | Cl | H | |
| 2-83 | 3-Cl | H | H | Cl | H | |
| 2-84 | 4-Cl | H | H | Cl | H | |
| 2-85 | 3-CH₃ | H | H | Cl | H | |
| 2-86 | 4-CH₃ | H | H | Cl | H | |
| 2-87 | 3-CF₃ | H | H | Cl | H | |
| 2-88 | 4-CF₃ | H | H | Cl | H | |
| 2-89 | 3,4-Cl₂ | H | H | Cl | H | |
| 2-90 | 3,4-(CH₃)₂ | H | H | Cl | H | |

TABLE 14

| Comp. No. | Ym | X¹ | X² | X³ | X⁴ | m.p. (° C.) |
|---|---|---|---|---|---|---|
| 2-91 | H | H | H | CH₃ | H | 68–71 |
| 2-92 | 3-F | H | H | CH₃ | H | |
| 2-93 | 4-F | H | H | CH₃ | H | |
| 2-94 | 3-Cl | H | H | CH₃ | H | |
| 2-95 | 4-Cl | H | H | CH₃ | H | 103–106 |
| 2-96 | 3-CH₃ | H | H | CH₃ | H | |
| 2-97 | 4-CH₃ | H | H | CH₃ | H | 89–92 |
| 2-98 | 3-CF₃ | H | H | CH₃ | H | oily |
| 2-99 | 4-CF₃ | H | H | CH₃ | H | |
| 2-100 | 3,4-Cl₂ | H | H | CH₃ | H | |
| 2-101 | 3,4-(CH₃)₂ | H | H | CH₃ | H | |
| 2-102 | H | H | H | H | F | 87–88 |
| 2-103 | 3-F | H | H | H | F | 43–46 |
| 2-104 | 4-F | H | H | H | F | 77–79 |
| 2-105 | 2-Cl | H | H | H | F | |
| 2-106 | 3-Cl | H | H | H | F | oily |
| 2-107 | 4-Cl | H | H | H | F | 113–114 |
| 2-108 | 2-CH₃ | H | H | H | F | |
| 2-109 | 3-CH₃ | H | H | H | F | oily |
| 2-110 | 4-CH₃ | H | H | H | F | 106–108 |
| 2-111 | 3-C₂H₅ | H | H | H | F | oily |
| 2-112 | 4-C₂H₅ | H | H | H | F | 86–88 |
| 2-113 | 3-C₃H₇-i | H | H | H | F | oily |
| 2-114 | 4-C₃H₇-i | H | H | H | F | 61–62 |
| 2-115 | 3-C₄H₉-t | H | H | H | F | |
| 2-116 | 4-C₄H₉-t | H | H | H | F | oily |
| 2-117 | 3-▷ | H | H | H | F | |
| 2-118 | 4-▷ | H | H | H | F | |

TABLE 14-continued

| Comp. No. | Ym | X¹ | X² | X³ | X⁴ | m.p. (° C.) |
|---|---|---|---|---|---|---|
| 2-119 | 3-phenyl | H | H | H | F | |
| 2-120 | 4-phenyl | H | H | H | F | |
| 2-121 | 3-CF$_3$ | H | H | H | F | 87–89 |

TABLE 15

| Comp. No. | Ym | X¹ | X² | X³ | X⁴ | m.p. (° C.) |
|---|---|---|---|---|---|---|
| 2-122 | 4-CF$_3$ | H | H | H | F | 71–74 |
| 2-123 | 3-OCH$_3$ | H | H | H | F | oily |
| 2-124 | 4-OCH$_3$ | H | H | H | F | 131–134 |
| 2-125 | 3-OCF$_3$ | H | H | H | F | oily |
| 2-126 | 4-OCF$_3$ | H | H | H | F | oily |
| 2-127 | 3-OCHF$_2$ | H | H | H | F | |
| 2-128 | 4-OCHF$_2$ | H | H | H | F | |
| 2-129 | 3-O-phenyl | H | H | H | F | |
| 2-130 | 4-O-phenyl | H | H | H | F | 94–95 |
| 2-131 | 3-OCH$_2$-phenyl | H | H | H | F | |
| 2-132 | 4-OCH$_2$-phenyl | H | H | H | F | |
| 2-133 | 3-SCHF$_2$ | H | H | H | F | |
| 2-134 | 4-SCHF$_2$ | H | H | H | F | |
| 2-135 | 3-SCF$_3$ | H | H | H | F | |
| 2-136 | 4-SCF$_3$ | H | H | H | F | |
| 2-137 | 3-COOCH$_3$ | H | H | H | F | |
| 2-138 | 4-COOCH$_3$ | H | H | H | F | |
| 2-139 | 3-COCH$_3$ | H | H | H | F | 75–76 |
| 2-140 | 4-COCH$_3$ | H | H | H | F | 105–106 |
| 2-141 | 3-CONH$_2$ | H | H | H | F | |
| 2-142 | 4-CONH$_2$ | H | H | H | F | |
| 2-143 | 3-NO$_2$ | H | H | H | F | |
| 2-144 | 4-NO$_2$ | H | H | H | F | |
| 2-145 | 3-CN | H | H | H | F | |
| 2-146 | 4-CN | H | H | H | F | |
| 2-147 | 3-SCH$_3$ | H | H | H | F | |
| 2-148 | 4-SCH$_3$ | H | H | H | F | |
| 2-149 | 3-SOCH$_3$ | H | H | H | F | |
| 2-150 | 4-SOCH$_3$ | H | H | H | F | |
| 2-151 | 3-SO$_2$CH$_3$ | H | H | H | F | |
| 2-152 | 4-SO$_2$CH$_3$ | H | H | H | F | |

TABLE 16

| Comp. No. | Ym | X¹ | X² | X³ | X⁴ | m.p. (° C.) |
|---|---|---|---|---|---|---|
| 2-153 | 4-CH=CH$_2$ | H | H | H | F | |
| 2-154 | 3-NH$_2$ | H | H | H | F | |
| 2-155 | 4-NH$_2$ | H | H | H | F | |
| 2-156 | 3-NHCH$_3$ | H | H | H | F | |
| 2-157 | 4-NHCH$_3$ | H | H | H | F | |
| 2-158 | 3-N(CH$_3$)$_2$ | H | H | H | F | |
| 2-159 | 4-N(CH$_3$)$_2$ | H | H | H | F | |
| 2-160 | 3-NHCOCH$_3$ | H | H | H | F | |
| 2-161 | 4-NHCOCH$_3$ | H | H | H | F | |
| 2-162 | 3-NHCOC$_2$H$_5$ | H | H | H | F | |
| 2-163 | 4-NHCOC$_2$H$_5$ | H | H | H | F | |
| 2-164 | 3,4-Cl$_2$ | H | H | H | F | 97–98 |
| 2-165 | 3,5-Cl$_2$ | H | H | H | F | |
| 2-166 | 3,4-(CH$_3$)$_2$ | H | H | H | F | oily |
| 2-167 | 3,5-(CH$_3$)$_2$ | H | H | H | F | |
| 2-168 | 3-F,4-CH$_3$ | H | H | H | F | |
| 2-169 | 3-Cl,4-CH$_3$ | H | H | H | F | |
| 2-170 | 3-Cl, 4-CF$_3$ | H | H | H | F | |
| 2-171 | 4-F, 3-CH$_3$ | H | H | H | F | 64–66 |
| 2-172 | 4-Cl, 3-CH$_3$ | H | H | H | F | |
| 2-173 | 4-Br, 3-CH$_3$ | H | H | H | F | |
| 2-174 | 4-Cl, 3-OCH$_3$ | H | H | H | F | |
| 2-175 | 4-Cl, 3-OC$_2$H$_5$ | H | H | H | F | |
| 2-176 | 3,5-(CH$_3$)$_2$, 4-F | H | H | H | F | |
| 2-177 | 3-NO$_2$, 4-CH$_3$ | H | H | H | F | |
| 2-178 | 3,5-(CF$_3$)$_2$ | H | H | H | F | |
| 2-179 | 2,4-(CF$_3$)$_2$ | H | H | H | F | |
| 2-180 | 5-Br, 2-OCH$_3$ | H | H | H | F | |
| 2-181 | 2,4,6-(CH$_3$)$_3$ | H | H | H | F | |
| 2-182 | H | H | H | H | Cl | 88–91 |
| 2-183 | 3-F | H | H | H | Cl | 81–82 |

TABLE 17

| Comp. No. | Ym | X¹ | X² | X³ | X⁴ | m.p. (° C.) |
|---|---|---|---|---|---|---|
| 2-184 | 4-F | H | H | H | Cl | 82–83 |
| 2-185 | 2-Cl | H | H | H | Cl | oily |
| 2-186 | 3-Cl | H | H | H | Cl | oily |
| 2-187 | 4-Cl | H | H | H | Cl | 111–114 |
| 2-188 | 2-CH$_3$ | H | H | H | Cl | oily |
| 2-189 | 3-CH$_3$ | H | H | H | Cl | oily |
| 2-190 | 4-CH$_3$ | H | H | H | Cl | 106–109 |
| 2-191 | 3-C$_2$H$_5$ | H | H | H | Cl | oily |
| 2-192 | 4-C$_2$H$_5$ | H | H | H | Cl | 107–110 |
| 2-193 | 3-C$_3$H$_7$-i | H | H | H | Cl | oily |
| 2-194 | 4-C$_3$H$_7$-i | H | H | H | Cl | 68–71 |
| 2-195 | 3-C$_4$H$_9$-t | H | H | H | Cl | |
| 2-196 | 4-C$_4$H$_9$-t | H | H | H | Cl | oily |
| 2-197 | 3-cyclopropyl | H | H | H | Cl | |
| 2-198 | 4-cyclopropyl | H | H | H | Cl | |
| 2-199 | 3-phenyl | H | H | H | Cl | |
| 2-200 | 4-phenyl | H | H | H | Cl | |
| 2-201 | 3-CF$_3$ | H | H | H | Cl | 99–101 |
| 2-202 | 4-CF$_3$ | H | H | H | Cl | 101–104 |
| 2-203 | 3-OCH$_3$ | H | H | H | Cl | 65–67 |
| 2-204 | 4-OCH$_3$ | H | H | H | Cl | 121–124 |
| 2-205 | 3-OCF$_3$ | H | H | H | Cl | 85–88 |

TABLE 17-continued

| Comp. No. | Ym | $X^1$ | $X^2$ | $X^3$ | $X^4$ | m.p. (° C.) |
|---|---|---|---|---|---|---|
| 2-206 | 4-OCF$_3$ | H | H | H | Cl | 73–76 |
| 2-207 | 3-OCHF$_2$ | H | H | H | Cl | 47–50 |
| 2-208 | 4-OCHF$_2$ | H | H | H | Cl | 86–89 |
| 2-209 | 3-O-C$_6$H$_5$ | H | H | H | Cl | |
| 2-210 | 4-O-C$_6$H$_5$ | H | H | H | Cl | |
| 2-211 | 3-OCH$_2$-C$_6$H$_5$ | H | H | H | Cl | |
| 2-212 | 4-OCH$_2$-C$_6$H$_5$ | H | H | H | Cl | |
| 2-213 | 3-SCHF$_2$ | H | H | H | Cl | |
| 2-214 | 4-SCHF$_2$ | H | H | H | Cl | |

TABLE 18

| Comp. No. | Ym | $X^1$ | $X^2$ | $X^3$ | $X^4$ | m.p. (° C.) |
|---|---|---|---|---|---|---|
| 2-215 | 3-SCF$_3$ | H | H | H | Cl | 124–126 |
| 2-216 | 4-SCF$_3$ | H | H | H | Cl | 125–128 |
| 2-217 | 3-COOCH$_3$ | H | H | H | Cl | |
| 2-218 | 4-COOCH$_3$ | H | H | H | Cl | |
| 2-219 | 3-COOC$_2$H$_5$ | H | H | H | Cl | |
| 2-220 | 4-COOC$_2$H$_5$ | H | H | H | Cl | 119–122 |
| 2-221 | 3-CONH$_2$ | H | H | H | Cl | |
| 2-222 | 4-CONH$_2$ | H | H | H | Cl | |
| 2-223 | 3-NO$_2$ | H | H | H | Cl | 198–201 |
| 2-224 | 4-NO$_2$ | H | H | H | Cl | |
| 2-225 | 3-CN | H | H | H | Cl | |
| 2-226 | 4-CN | H | H | H | Cl | 161–164 |
| 2-227 | 3-SCH$_3$ | H | H | H | Cl | |
| 2-228 | 4-SCH$_3$ | H | H | H | Cl | |
| 2-229 | 3-SOCH$_3$ | H | H | H | Cl | |
| 2-230 | 4-SOCH$_3$ | H | H | H | Cl | |
| 2-231 | 3-SO$_2$CH$_3$ | H | H | H | Cl | |
| 2-232 | 4-SO$_2$CH$_3$ | H | H | H | Cl | |
| 2-233 | 4-CH=CH$_2$ | H | H | H | Cl | |
| 2-234 | 3-NH$_2$ | H | H | H | Cl | |
| 2-235 | 4-NH$_2$ | H | H | H | Cl | |
| 2-236 | 3-NHCH$_3$ | H | H | H | Cl | |
| 2-237 | 4-NHCH$_3$ | H | H | H | Cl | |
| 2-238 | 3-N(CH$_3$)$_2$ | H | H | H | Cl | |
| 2-239 | 4-N(CH$_3$)$_2$ | H | H | H | Cl | |
| 2-240 | 3-NHCOCH$_3$ | H | H | H | Cl | |
| 2-241 | 4-NHCOCH$_3$ | H | H | H | Cl | |
| 2-242 | 3-NHCOC$_2$H$_5$ | H | H | H | Cl | |
| 2-243 | 4-NHCOC$_2$H$_5$ | H | H | H | Cl | |
| 2-244 | 3,4-Cl$_2$ | H | H | H | Cl | 86–89 |
| 2-245 | 3,5-Cl$_2$ | H | H | H | Cl | 114–117 |

TABLE 19

| Comp. No. | Ym | $X^1$ | $X^2$ | $X^3$ | $X^4$ | m.p. (° C.) |
|---|---|---|---|---|---|---|
| 2-246 | 3,4-(CH$_3$)$_2$ | H | H | H | Cl | 67–68 |
| 2-247 | 3,5-(CH$_3$)$_2$ | H | H | H | Cl | 91–94 |
| 2-248 | 3-F, 4-CH$_3$ | H | H | H | Cl | 97–98 |
| 2-249 | 3-Cl, 4-CH$_3$ | H | H | H | Cl | 84–85 |
| 2-250 | 3-Cl, 4-CF$_3$ | H | H | H | Cl | |
| 2-251 | 4-F, 3-CH$_3$ | H | H | H | Cl | 75–78 |
| 2-252 | 4-Cl, 3-CH$_3$ | H | H | H | Cl | |
| 2-253 | 4-Br, 3-CH$_3$ | H | H | H | Cl | |
| 2-254 | 4-Cl, 3-OCH$_3$ | H | H | H | Cl | |
| 2-255 | 4-Cl, 3-OC$_2$H$_5$ | H | H | H | Cl | |
| 2-256 | 3,5-(CH$_3$)$_2$, 4-F | H | H | H | Cl | |
| 2-257 | 3-NO$_2$, 4-CH$_3$ | H | H | H | Cl | 119–122 |
| 2-258 | 3,5-(CF$_3$)$_2$ | H | H | H | Cl | 170–171 |
| 2-259 | 2,4-(CF$_3$)$_2$ | H | H | H | Cl | |
| 2-260 | 5-Br, 2-OCH$_3$ | H | H | H | Cl | |
| 2-261 | 2,4,6-(CH$_3$)$_3$ | H | H | H | Cl | 160–161 |
| 2-262 | H | H | H | H | Br | |
| 2-263 | 3-F | H | H | H | Br | |
| 2-264 | 4-F | H | H | H | Br | |
| 2-265 | 3-Cl | H | H | H | Br | |
| 2-266 | 4-Cl | H | H | H | Br | 133–136 |
| 2-267 | 3-CH$_3$ | H | H | H | Br | |
| 2-268 | 4-CH$_3$ | H | H | H | Br | 114–117 |
| 2-269 | 3-C$_2$H$_5$ | H | H | H | Br | |
| 2-270 | 4-C$_2$H$_5$ | H | H | H | Br | |
| 2-271 | 3-C$_3$H$_7$-i | H | H | H | Br | |
| 2-272 | 4-C$_3$H$_7$-i | H | H | H | Br | |
| 2-273 | 3-C$_4$H$_9$-t | H | H | H | Br | |
| 2-274 | 4-C$_4$H$_9$-t | H | H | H | Br | |
| 2-275 | 3-OCH$_3$ | H | H | H | Br | |
| 2-276 | 4-OCH$_3$ | H | H | H | Br | |

TABLE 20

| Comp. No. | Ym | $X^1$ | $X^2$ | $X^3$ | $X^4$ | m.p. (° C.) |
|---|---|---|---|---|---|---|
| 2-277 | 3-CF$_3$ | H | H | H | Br | 113–115 |
| 2-278 | 4-CF$_3$ | H | H | H | Br | |
| 2-279 | 3,4-Cl$_2$ | H | H | H | Br | |
| 2-280 | 3,4-(CH$_3$)$_2$ | H | H | H | Br | 109–112 |
| 2-281 | 3,5-(CH$_3$)$_2$ | H | H | H | Br | |
| 2-282 | 3-OCF$_3$ | H | H | H | Br | |
| 2-283 | 4-OCF$_3$ | H | H | H | Br | |
| 2-284 | H | H | H | H | CH$_3$ | oily |
| 2-285 | 3-F | H | H | H | CH$_3$ | |
| 2-286 | 4-F | H | H | H | CH$_3$ | |
| 2-287 | 3-Cl | H | H | H | CH$_3$ | |
| 2-288 | 4-Cl | H | H | H | CH$_3$ | 90–93 |
| 2-289 | 3-CH$_3$ | H | H | H | CH$_3$ | |
| 2-290 | 4-CH$_3$ | H | H | H | CH$_3$ | 71–73 |
| 2-291 | 3-C$_2$H$_5$ | H | H | H | CH$_3$ | |
| 2-292 | 4-C$_2$H$_5$ | H | H | H | CH$_3$ | |
| 2-293 | 3-C$_3$H$_7$-i | H | H | H | CH$_3$ | |
| 2-294 | 4-C$_3$H$_7$-i | H | H | H | CH$_3$ | |
| 2-295 | 3-C$_4$H$_9$-t | H | H | H | CH$_3$ | |
| 2-296 | 4-C$_4$H$_9$-t | H | H | H | CH$_3$ | |
| 2-297 | 3-OCH$_3$ | H | H | H | CH$_3$ | |
| 2-298 | 4-OCH$_3$ | H | H | H | CH$_3$ | |
| 2-299 | 3-CF$_3$ | H | H | H | CH$_3$ | 79–82 |
| 2-300 | 4-CF$_3$ | H | H | H | CH$_3$ | 105–108 |
| 2-301 | 3,4-Cl$_2$ | H | H | H | CH$_3$ | |
| 2-302 | 3,4-(CH$_3$)$_2$ | H | H | H | CH$_3$ | |
| 2-303 | 3,5-(CH$_3$)$_2$ | H | H | H | CH$_3$ | |
| 2-304 | 3-OCF$_3$ | H | H | H | CH$_3$ | |
| 2-305 | 4-OCF$_3$ | H | H | H | CH$_3$ | |
| 2-306 | H | H | H | H | CF$_3$ | |
| 2-307 | 3-F | H | H | H | CF$_3$ | |

TABLE 21

| Comp. No. | Ym | $X^1$ | $X^2$ | $X^3$ | $X^4$ | m.p. (° C.) |
|---|---|---|---|---|---|---|
| 2-308 | 4-F | H | H | H | $CF_3$ | |
| 2-309 | 3-Cl | H | H | H | $CF_3$ | |
| 2-310 | 4-Cl | H | H | H | $CF_3$ | |
| 2-311 | 3-$CH_3$ | H | H | H | $CF_3$ | |
| 2-312 | 4-$CH_3$ | H | H | H | $CF_3$ | |
| 2-313 | 3-$C_2H_5$ | H | H | H | $CF_3$ | |
| 2-314 | 4-$C_2H_5$ | H | H | H | $CF_3$ | |
| 2-315 | 3-$C_3H_7$-i | H | H | H | $CF_3$ | |
| 2-316 | 4-$C_3H_7$-i | H | H | H | $CF_3$ | |
| 2-317 | 3-$C_4H_9$-t | H | H | H | $CF_3$ | |
| 2-318 | 4-$C_4H_9$-t | H | H | H | $CF_3$ | |
| 2-319 | 3-$OCH_3$ | H | H | H | $CF_3$ | |
| 2-320 | 4-$OCH_3$ | H | H | H | $CF_3$ | |
| 2-321 | 3-$CF_3$ | H | H | H | $CF_3$ | |
| 2-322 | 4-$CF_3$ | H | H | H | $CF_3$ | |
| 2-323 | 3,4-$Cl_2$ | H | H | H | $CF_3$ | |
| 2-324 | 3,4-$(CH_3)_2$ | H | H | H | $CF_3$ | |
| 2-325 | 3,5-$(CH_3)_2$ | H | H | H | $CF_3$ | |
| 2-326 | 3-$OCF_3$ | H | H | H | $CF_3$ | |
| 2-327 | 4-$OCF_3$ | H | H | H | $CF_3$ | |
| 2-328 | H | H | H | H | $OCH_3$ | 77–79 |
| 2-329 | 3-F | H | H | H | $OCH_3$ | |
| 2-330 | 4-F | H | H | H | $OCH_3$ | |
| 2-331 | 3-Cl | H | H | H | $OCH_3$ | 89–92 |
| 2-332 | 4-Cl | H | H | H | $OCH_3$ | 116–119 |
| 2-333 | 3-$CH_3$ | H | H | H | $OCH_3$ | |
| 2-334 | 4-$CH_3$ | H | H | H | $OCH_3$ | 107–108 |
| 2-335 | 3-$C_2H_5$ | H | H | H | $OCH_3$ | |
| 2-336 | 4-$C_2H_5$ | H | H | H | $OCH_3$ | |
| 2-337 | 3-$C_3H_7$-i | H | H | H | $OCH_3$ | |
| 2-338 | 4-$C_3H_7$-i | H | H | H | $OCH_3$ | |

TABLE 22

| Comp. No. | Ym | $X^1$ | $X^2$ | $X^3$ | $X^4$ | m.p. (° C.) |
|---|---|---|---|---|---|---|
| 2-339 | 3-$C_4H_9$-t | H | H | H | $OCH_3$ | |
| 2-340 | 4-$C_4H_9$-t | H | H | H | $OCH_3$ | |
| 2-341 | 3-$OCH_3$ | H | H | H | $OCH_3$ | |
| 2-342 | 4-$OCH_3$ | H | H | H | $OCH_3$ | |
| 2-343 | 3-$CF_3$ | H | H | H | $OCH_3$ | 78–81 |
| 2-344 | 4-$CF_3$ | H | H | H | $OCH_3$ | 110–113 |
| 2-345 | 3,4-$Cl_2$ | H | H | H | $OCH_3$ | |
| 2-346 | 3,4-$(CH_3)_2$ | H | H | H | $OCH_3$ | oily |
| 2-347 | 3,5-$(CH_3)_2$ | H | H | H | $OCH_3$ | |
| 2-348 | 3-$OCF_3$ | H | H | H | $OCH_3$ | |
| 2-349 | 4-$OCF_3$ | H | H | H | $OCH_3$ | |
| 2-350 | H | H | H | H | $OCHF_2$ | |
| 2-351 | 3-F | H | H | H | $OCHF_2$ | |
| 2-352 | 4-F | H | H | H | $OCHF_2$ | |
| 2-353 | 3-Cl | H | H | H | $OCHF_2$ | |
| 2-354 | 4-Cl | H | H | H | $OCHF_2$ | |
| 2-355 | 3-$CH_3$ | H | H | H | $OCHF_2$ | |
| 2-356 | 4-$CH_3$ | H | H | H | $OCHF_2$ | |
| 2-357 | 3-$C_2H_5$ | H | H | H | $OCHF_2$ | |
| 2-358 | 4-$C_2H_5$ | H | H | H | $OCHF_2$ | |
| 2-359 | 3-$C_3H_7$-i | H | H | H | $OCHF_2$ | |
| 2-360 | 4-$C_3H_7$-i | H | H | H | $OCHF_2$ | |
| 2-361 | 3-$C_4H_9$-t | H | H | H | $OCHF_2$ | |
| 2-362 | 4-$C_4H_9$-t | H | H | H | $OCHF_2$ | |
| 2-363 | 3-$OCH_3$ | H | H | H | $OCHF_2$ | |
| 2-364 | 4-$OCH_3$ | H | H | H | $OCHF_2$ | |
| 2-365 | 3-$CF_3$ | H | H | H | $OCHF_2$ | 63–66 |
| 2-366 | 4-$CF_3$ | H | H | H | $OCHF_2$ | |
| 2-367 | 3,4-$Cl_2$ | H | H | H | $OCHF_2$ | |
| 2-368 | 3,4-$(CH_3)_2$ | H | H | H | $OCHF_2$ | |
| 2-369 | 3,5-$(CH_3)_2$ | H | H | H | $OCHF_2$ | |

TABLE 23

| Comp. No. | Ym | $X^1$ | $X^2$ | $X^3$ | $X^4$ | m.p. (° C.) |
|---|---|---|---|---|---|---|
| 2-370 | 3-$OCF_3$ | H | H | H | $OCHF_2$ | |
| 2-371 | 4-$OCF_3$ | H | H | H | $OCHF_2$ | |
| 2-372 | H | H | F | H | F | |
| 2-373 | 3-F | H | F | H | F | |
| 2-374 | 4-F | H | F | H | F | |
| 2-375 | 3-Cl | H | F | H | F | |
| 2-376 | 4-Cl | H | F | H | F | |
| 2-377 | 3-$CH_3$ | H | F | H | F | |
| 2-378 | 4-$CH_3$ | H | F | H | F | |
| 2-379 | 3-$C_2H_5$ | H | F | H | F | |
| 2-380 | 4-$C_2H_5$ | H | F | H | F | |
| 2-381 | 3-$C_3H_7$-i | H | F | H | F | |
| 2-382 | 4-$C_3H_7$-i | H | F | H | F | |
| 2-383 | 3-$C_4H_9$-t | H | F | H | F | |
| 2-384 | 4-$C_4H_9$-t | H | F | H | F | |
| 2-385 | 3-$OCH_3$ | H | F | H | F | |
| 2-386 | 4-$OCH_3$ | H | F | H | F | |
| 2-387 | 3-$CF_3$ | H | F | H | F | |
| 2-388 | 4-$CF_3$ | H | F | H | F | |
| 2-389 | 3,4-$Cl_2$ | H | F | H | F | |
| 2-390 | 3,4-$(CH_3)_2$ | H | F | H | F | |
| 2-391 | 3,5-$(CH_3)_2$ | H | F | H | F | |
| 2-392 | 3-$OCF_3$ | H | F | H | F | |
| 2-393 | 4-$OCF_3$ | H | F | H | F | |
| 2-394 | H | H | H | $CF_3$ | H | |
| 2-395 | 3-Cl | H | H | $CF_3$ | H | |
| 2-396 | 4-Cl | H | H | $CF_3$ | H | |
| 2-397 | 3-$CH_3$ | H | H | $CF_3$ | H | |
| 2-398 | 4-$CH_3$ | H | H | $CF_3$ | H | |
| 2-399 | 3-$CF_3$ | H | H | $CF_3$ | H | |
| 2-400 | 4-$CF_3$ | H | H | $CF_3$ | H | |

TABLE 24

| Comp. No. | Ym | $X^1$ | $X^2$ | $X^3$ | $X^4$ | m.p. (° C.) |
|---|---|---|---|---|---|---|
| 2-401 | 3-$COCH_3$ | H | H | H | F | |
| 2-402 | 4-$COCH_3$ | H | H | H | F | |
| 2-403 | 3-Br | H | H | H | F | |
| 2-404 | 4-Br | H | H | H | F | |
| 2-405 | 3,4-$(OH)_2$ | H | H | H | F | |
| 2-406 | 3,4-$(OCH_3)_2$ | H | H | H | F | |
| 2-407 | 3,4-$(OCH_2O)$ | H | H | H | F | |
| 2-408 | 2,3-$Cl_2$ | H | H | H | F | |
| 2-409 | 2,4-$Cl_2$ | H | H | H | F | |
| 2-410 | 2,5-$Cl_2$ | H | H | H | F | |
| 2-411 | 2,4-$F_2$ | H | H | H | F | |
| 2-412 | 3,4-$F_2$ | H | H | H | F | 55–56 |
| 2-413 | 2,5-$F_2$ | H | H | H | F | |
| 2-414 | 2-F, 4-Cl | H | H | H | F | |
| 2-415 | 3-F, 4-Cl | H | H | H | F | |
| 2-416 | 3-Cl, 4-F | H | H | H | F | 101–103 |
| 2-417 | 2,4-$(CH_3)_2$ | H | H | H | F | |
| 2-418 | 2,5-$(CH_3)_2$ | H | H | H | F | |
| 2-419 | 2-F, 4-$CH_3$ | H | H | H | F | |
| 2-420 | 2-Cl, 4-$CH_3$ | H | H | H | F | |
| 2-421 | 2-F, 5-$CH_3$ | H | H | H | F | |
| 2-422 | 2-Cl, 5-$CH_3$ | H | H | H | F | |
| 2-423 | 2-$OCH_3$, 5-$CH_3$ | H | H | H | F | |
| 2-424 | 3-$C_2H_5$, 4-Cl | H | H | H | F | |
| 2-425 | 3-CN, 4-F | H | H | H | F | |
| 2-426 | 3-CN, 4-Cl | H | H | H | F | |
| 2-427 | 3-CN, 4-$OCH_3$ | H | H | H | F | |
| 2-428 | 3-$COCH_3$, 4-$OCH_3$ | H | H | H | F | |
| 2-429 | 3,5-$(CH_3)_2$, 4-Cl | H | H | H | F | |
| 2-430 | 3,5-$(CH_3)_2$, 4-$OCH_3$ | H | H | H | F | |
| 2-431 | 3,4,5-$(CH_3)_3$ | H | H | H | F | |

TABLE 25

| Comp. No. | Ym | $X^1$ | $X^2$ | $X^3$ | $X^4$ | m.p. (° C.) |
|---|---|---|---|---|---|---|
| 2-432 | 3,4,5-(OCH$_3$)$_3$ | H | H | H | F | |
| 2-433 | 3,5-(C$_2$H$_5$)$_2$, 4-Cl | H | H | H | F | |
| 2-434 | 3-CF$_3$, 4-F | H | H | H | F | |
| 2-435 | 3-CF$_3$, 4-Cl | H | H | H | F | |
| 2-436 | 3-F, 5-CF$_3$ | H | H | H | F | |
| 2-437 | 2-F, 5-CF$_3$ | H | H | H | F | |
| 2-438 | 2-Cl, 5-CF$_3$ | H | H | H | F | |
| 2-439 | 2-F, 3-CF$_3$ | H | H | H | F | |
| 2-440 | 2-F, 4-CF$_3$ | H | H | H | F | |
| 2-441 | 3,4-F$_2$, 5-CF$_3$ | H | H | H | F | |
| 2-442 | 3-COOCH$_3$, 4-Cl | H | H | H | F | |
| 2-443 | 3-COOCH$_3$, 4-CH$_3$ | H | H | H | F | |
| 2-444 | 3-C≡CH | H | H | H | F | |
| 2-445 | 4-C≡CH | H | H | H | F | |
| 2-446 | 3-C≡C—CH$_3$ | H | H | H | F | |
| 2-447 | 4-C≡C—CH$_3$ | H | H | H | F | |
| 2-448 | 3-OH | H | H | H | Cl | oily |
| 2-449 | 4-OH | H | H | H | Cl | 168–171 |
| 2-450 | 3-COCH$_3$ | H | H | H | Cl | 84–86 |
| 2-451 | 4-COCH$_3$ | H | H | H | Cl | 122–125 |
| 2-452 | 3-Br | H | H | H | Cl | |
| 2-453 | 4-Br | H | H | H | Cl | 124–127 |
| 2-454 | 3,4-(OH)$_2$ | H | H | H | Cl | 193–196 |
| 2-455 | 3,4-(OCH$_3$)$_2$ | H | H | H | Cl | 113–116 |
| 2-456 | 3,4-(OCH$_2$O) | H | H | H | Cl | 106–107 |
| 2-457 | 2,3-Cl$_2$ | H | H | H | Cl | 159–162 |
| 2-458 | 2,4-Cl$_2$ | H | H | H | Cl | oily |
| 2-459 | 2,5-Cl$_2$ | H | H | H | Cl | |
| 2-460 | 2,4-F$_2$ | H | H | H | Cl | |
| 2-461 | 3,4-F$_2$ | H | H | H | Cl | 68–71 |
| 2-462 | 2,5-F$_2$ | H | H | H | Cl | |

TABLE 26

| Comp. No. | Ym | $X^1$ | $X^2$ | $X^3$ | $X^4$ | m.p. (° C.) |
|---|---|---|---|---|---|---|
| 2-463 | 2-F, 4-Cl | H | H | H | Cl | |
| 2-464 | 3-F, 4-Cl | H | H | H | Cl | |
| 2-465 | 3-Cl, 4-F | H | H | H | Cl | 92–95 |
| 2-466 | 2,4-(CH$_3$)$_2$ | H | H | H | Cl | |
| 2-467 | 2,5-(CH$_3$)$_2$ | H | H | H | Cl | |
| 2-468 | 2-F, 4-CH$_3$ | H | H | H | Cl | |
| 2-469 | 2-Cl, 4-CH$_3$ | H | H | H | Cl | |
| 2-470 | 2-F, 5-CH$_3$ | H | H | H | Cl | |
| 2-471 | 2-Cl, 5-CH$_3$ | H | H | H | Cl | |
| 2-472 | 2-OCH$_3$, 5-CH$_3$ | H | H | H | Cl | |
| 2-473 | 3-C$_2$H$_5$, 4-Cl | H | H | H | Cl | |
| 2-474 | 3-CN, 4-F | H | H | H | Cl | |
| 2-475 | 3-CN, 4-Cl | H | H | H | Cl | |
| 2-476 | 3-CN, 4-OCH$_3$ | H | H | H | Cl | |
| 2-477 | 3-COCH$_3$, 4-OCH$_3$ | H | H | H | Cl | |
| 2-478 | 3,5-(CH$_3$)$_2$, 4-Cl | H | H | H | Cl | |
| 2-479 | 3,5-(CH$_3$)$_2$, 4-OCH$_3$ | H | H | H | Cl | |
| 2-480 | 3,4,5-(CH$_3$)$_3$ | H | H | H | Cl | |
| 2-481 | 3,4,5-(OCH$_3$)$_3$ | H | H | H | Cl | 120–121 |
| 2-482 | 3,5-(C$_2$H$_5$)$_2$, 4-Cl | H | H | H | Cl | |
| 2-483 | 3-CF$_3$, 4-F | H | H | H | Cl | |
| 2-484 | 3-CF$_3$, 4-Cl | H | H | H | Cl | |
| 2-485 | 3-F, 5-CF$_3$ | H | H | H | Cl | |
| 2-486 | 2-F, 5-CF$_3$ | H | H | H | Cl | |
| 2-487 | 2-Cl, 5-CF$_3$ | H | H | H | Cl | |
| 2-488 | 2-F, 3-CF$_3$ | H | H | H | Cl | |
| 2-489 | 2-F, 4-CF$_3$ | H | H | H | Cl | |
| 2-490 | 3, 4-F$_2$, 5-CF$_3$ | H | H | H | Cl | |
| 2-491 | 3-COOCH$_3$, 4-Cl | H | H | H | Cl | |
| 2-492 | 3-COOCH$_3$, 4-CH$_3$ | H | H | H | Cl | |
| 2-493 | 3-C≡CH | H | H | H | Cl | |

TABLE 27

| Comp. No. | Ym | $X^1$ | $X^2$ | $X^3$ | $X^4$ | m.p. (° C.) |
|---|---|---|---|---|---|---|
| 2-494 | 4-C≡CH | H | H | H | Cl | |
| 2-495 | 3-C≡C—CH$_3$ | H | H | H | Cl | |
| 2-496 | 4-C≡C—CH$_3$ | H | H | H | Cl | |
| 2-497 | 3-COCH$_3$ | H | H | H | Br | |
| 2-498 | 4-COCH$_3$ | H | H | H | Br | |
| 2-499 | 3-Br | H | H | H | Br | |
| 2-500 | 4-Br | H | H | H | Br | |
| 2-501 | 3,4-(OH)$_2$ | H | H | H | Br | |
| 2-502 | 3,4-(OCH$_3$)$_2$ | H | H | H | Br | |
| 2-503 | 3,4-(OCH$_2$O) | H | H | H | Br | |
| 2-504 | 2,4-Cl$_2$ | H | H | H | Br | |
| 2-505 | 2,5-Cl$_2$ | H | H | H | Br | |
| 2-506 | 2,4-F$_2$ | H | H | H | Br | |
| 2-507 | 3,4-F$_2$ | H | H | H | Br | |
| 2-508 | 2,5-F$_2$ | H | H | H | Br | |
| 2-509 | 2-F, 4-Cl | H | H | H | Br | |
| 2-510 | 3-F, 4-Cl | H | H | H | Br | |
| 2-511 | 3-Cl, 4-F | H | H | H | Br | |
| 2-512 | 2,4-(CH$_3$)$_2$ | H | H | H | Br | |
| 2-513 | 2,5-(CH$_3$)$_2$ | H | H | H | Br | |
| 2-514 | 2-F, 4-CH$_3$ | H | H | H | Br | |
| 2-515 | 2-Cl, 4-CH$_3$ | H | H | H | Br | |
| 2-516 | 2-F, 5-CH$_3$ | H | H | H | Br | |
| 2-517 | 2-Cl, 5-CH$_3$ | H | H | H | Br | |
| 2-518 | 2-OCH$_3$, 5-CH$_3$ | H | H | H | Br | |
| 2-519 | 3-C$_2$H$_5$, 4-Cl | H | H | H | Br | |
| 2-520 | 3-CN, 4-F | H | H | H | Br | |
| 2-521 | 3-CN, 4-Cl | H | H | H | Br | |
| 2-522 | 3-CN, 4-OCH$_3$ | H | H | H | Br | |
| 2-523 | 3-COCH$_3$, 4-OCH$_3$ | H | H | H | Br | |
| 2-524 | 3,5-(CH$_3$)$_2$, 4-Cl | H | H | H | Br | |

TABLE 28

| Comp. No. | Ym | $X^1$ | $X^2$ | $X^3$ | $X^4$ | m.p. (° C.) |
|---|---|---|---|---|---|---|
| 2-525 | 3,5-(CH$_3$)$_2$, 4-OCH$_3$ | H | H | H | Br | |
| 2-526 | 3,4 5-(CH$_3$)$_3$ | H | H | H | Br | |
| 2-527 | 3,4,5-(OCH$_3$)$_3$ | H | H | H | Br | |
| 2-528 | 3,5-(C$_2$H$_5$)$_2$, 4-Cl | H | H | H | Br | |
| 2-529 | 3-CF$_3$, 4-F | H | H | H | Br | |
| 2-530 | 3-CF$_3$, 4-Cl | H | H | H | Br | |
| 2-531 | 3-F, 5-CF$_3$ | H | H | H | Br | |
| 2-532 | 2-F, 5-CF$_3$ | H | H | H | Br | |
| 2-533 | 2-Cl, 5-CF$_3$ | H | H | H | Br | |
| 2-534 | 2-F, 3-CF$_3$ | H | H | H | Br | |
| 2-535 | 2-F, 4-CF$_3$ | H | H | H | Br | |
| 2-536 | 3,4-F$_2$, 5-CF$_3$ | H | H | H | Br | |
| 2-537 | 3-COOCH$_3$, 4-Cl | H | H | H | Br | |
| 2-538 | 3-COOCH$_3$, 4-CH$_3$ | H | H | H | Br | |
| 2-539 | 3-C≡CH | H | H | H | Br | |
| 2-540 | 4-C≡CH | H | H | H | Br | |
| 2-541 | 3-C≡C—CH$_3$ | H | H | H | Br | |
| 2-542 | 4-C≡C—CH$_3$ | H | H | H | Br | |
| 2-543 | H | H | H | H | I | |
| 2-544 | 3-F | H | H | H | I | |
| 2-545 | 4-F | H | H | H | I | |
| 2-546 | 3-Cl | H | H | H | I | |
| 2-547 | 4-Cl | H | H | H | I | |
| 2-548 | 3-Br | H | H | H | 1 | |
| 2-549 | 4-Br | H | H | H | I | |
| 2-550 | 3-CH$_3$ | H | H | H | I | |
| 2-551 | 4-CH$_3$ | H | H | H | I | 141–144 |
| 2-552 | 3-C$_2$H$_5$ | H | H | H | I | |
| 2-553 | 4-C$_2$H$_5$ | H | H | H | I | |
| 2-554 | 3-OCH$_3$ | H | H | H | I | |
| 2-555 | 4-OCH$_3$ | H | H | H | I | |

TABLE 29

| Comp. No. | Ym | $X^1$ | $X^2$ | $X^3$ | $X^4$ | m.p. (°C) |
|---|---|---|---|---|---|---|
| 2-556 | 3-$CF_3$ | H | H | H | I | |
| 2-557 | 4-$CF_3$ | H | H | H | I | |
| 2-558 | 3-$COCH_3$ | H | H | H | I | |
| 2-559 | 4-$COCH_3$ | H | H | H | I | |
| 2-560 | 2,4-$(CH_3)_2$ | H | H | H | I | |
| 2-561 | 2,5-$(CH_3)_2$ | H | H | H | I | |
| 2-562 | 3,4-$(CH_3)_2$ | H | H | H | I | |
| 2-563 | 3,5-$(CH_3)_2$ | H | H | H | I | |
| 2-564 | 3,4-$(OCH_3)_2$ | H | H | H | I | |
| 2-565 | 2,4-$Cl_2$ | H | H | H | I | |
| 2-566 | 2,5-$Cl_2$ | H | H | H | I | |
| 2-567 | 3,4-$Cl_2$ | H | H | H | I | |
| 2-568 | 2,4-$F_2$ | H | H | H | I | |
| 2-569 | 2,5-$F_2$ | H | H | H | I | |
| 2-570 | 3,4-$F_2$ | H | H | H | I | |
| 2-571 | 2-F, 4-Cl | H | H | H | I | |
| 2-572 | 3-F, 4-Cl | H | H | H | I | |
| 2-573 | 3-Cl, 4-F | H | H | H | I | |
| 2-574 | 2,4-$(CH_3)_2$ | H | H | H | I | |
| 2-575 | 2,5-$(CH_3)_2$ | H | H | H | I | |
| 2-576 | 2-F, 4-$CH_3$ | H | H | H | I | |
| 2-577 | 2-Cl, 4-$CH_3$ | H | H | H | I | |
| 2-578 | 2-F, 5-$CH_3$ | H | H | H | I | |
| 2-579 | 2-Cl, 5-$CH_3$ | H | H | H | I | |
| 2-580 | 2-$OCH_3$, 5-$CH_3$ | H | H | H | I | |
| 2-581 | 3-$CF_3$, 4-F | H | H | H | I | |
| 2-582 | 3-$CF_3$, 4-Cl | H | H | H | I | |
| 2-583 | 3-F, 5-$CF_3$ | H | H | H | I | |
| 2-584 | 2-F, 5-$CF_3$ | H | H | H | I | |
| 2-585 | 2-Cl, 5-$CF_3$ | H | H | H | I | |
| 2-586 | 2-F, 3-$CF_3$ | H | H | H | I | |

TABLE 30

| Comp. No. | Ym | $X^1$ | $X^2$ | $X^3$ | $X^4$ | m.p. (°C) |
|---|---|---|---|---|---|---|
| 2-587 | 2-F, 4-$CF_3$ | H | H | H | I | |
| 2-588 | 3-$COCH_3$ | H | H | H | $CH_3$ | |
| 2-589 | 4-$COCH_3$ | H | H | H | $CH_3$ | |
| 2-590 | 3-Br | H | H | H | $CH_3$ | |
| 2-591 | 4-Br | H | H | H | $CH_3$ | |
| 2-592 | 3,4-$(OH)_2$ | H | H | H | $CH_3$ | |
| 2-593 | 3,4-$(OCH_3)_2$ | H | H | H | $CH_3$ | |
| 2-594 | 3,4-$(OCH_2O)$ | H | H | H | $CH_3$ | |
| 2-595 | 2,4-$Cl_2$ | H | H | H | $CH_3$ | |
| 2-596 | 2,5-$Cl_2$ | H | H | H | $CH_3$ | |
| 2-597 | 2,4-$F_2$ | H | H | H | $CH_3$ | |
| 2-598 | 3,4-$F_2$ | H | H | H | $CH_3$ | |
| 2-599 | 2,5-$F_2$ | H | H | H | $CH_3$ | |
| 2-600 | 2-F, 4-Cl | H | H | H | $CH_3$ | |
| 2-601 | 3-F, 4-Cl | H | H | H | $CH_3$ | |
| 2-602 | 3-Cl, 4-F | H | H | H | $CH_3$ | |
| 2-603 | 2,4-$(CH_3)_2$ | H | H | H | $CH_3$ | |
| 2-604 | 2,5-$(CH_3)_2$ | H | H | H | $CH_3$ | |
| 2-605 | 2-F, 4-$CH_3$ | H | H | H | $CH_3$ | |
| 2-606 | 2-Cl, 4-$CH_3$ | H | H | H | $CH_3$ | |
| 2-607 | 2-F, 5-$CH_3$ | H | H | H | $CH_3$ | |
| 2-608 | 2-Cl, 5-$CH_3$ | H | H | H | $CH_3$ | |
| 2-609 | 2-$OCH_3$, 5-$CH_3$ | H | H | H | $CH_3$ | |
| 2-610 | 3-$C_2H_5$, 4-Cl | H | H | H | $CH_3$ | |
| 2-611 | 3-CN, 4-F | H | H | H | $CH_3$ | |
| 2-612 | 3-CN, 4-Cl | H | H | H | $CH_3$ | |
| 2-613 | 3-CN, 4-$OCH_3$ | H | H | H | $CH_3$ | |
| 2-614 | 3-$COCH_3$, 4-$OCH_3$ | H | H | H | $CH_3$ | |
| 2-615 | 3,5-$(CH_3)_2$, 4-Cl | H | H | H | $CH_3$ | |
| 2-616 | 3,5-$(CH_3)_2$, 4-$OCH_3$ | H | H | H | $CH_3$ | |
| 2-617 | 3,4,5-$(CH_3)_3$ | H | H | H | $CH_3$ | |

TABLE 31

| Comp. No. | Ym | $X^1$ | $X^2$ | $X^3$ | $X^4$ | m.p. (°C) |
|---|---|---|---|---|---|---|
| 2-618 | 3,4,5-$(OCH_3)_3$ | H | H | H | $CH_3$ | |
| 2-619 | 3,5-$(C_2H_5)_2$, 4-Cl | H | H | H | $CH_3$ | |
| 2-620 | 3-$CF_3$, 4-F | H | H | H | $CH_3$ | |
| 2-621 | 3-$CF_3$, 4-Cl | H | H | H | $CH_3$ | |
| 2-622 | 3-F, 5-$CF_3$ | H | H | H | $CH_3$ | |
| 2-623 | 2-F, 5-$CF_3$ | H | H | H | $CH_3$ | |
| 2-624 | 2-Cl, 5-$CF_3$ | H | H | H | $CH_3$ | |
| 2-625 | 2-F, 3-$CF_3$ | H | H | H | $CH_3$ | |
| 2-626 | 2-F, 4-$CF_3$ | H | H | H | $CH_3$ | |
| 2-627 | 3,4-$F_2$, 5-$CF_3$ | H | H | H | $CH_3$ | |
| 2-628 | 3-$COOCH_3$, 4-Cl | H | H | H | $CH_3$ | |
| 2-629 | 3-$COOCH_3$, 4-$CH_3$ | H | H | H | $CH_3$ | |
| 2-630 | 3-C≡CH | H | H | H | $CH_3$ | |
| 2-631 | 4-C≡CH | H | H | H | $CH_3$ | |
| 2-632 | 3-C≡C—$CH_3$ | H | H | H | $CH_3$ | |
| 2-633 | 4-C≡C—$CH_3$ | H | H | H | $CH_3$ | |
| 2-634 | H | H | H | $CH_3$ | $OCH_3$ | |
| 2-635 | 3-F | H | H | $CH_3$ | $OCH_3$ | |
| 2-636 | 4-F | H | H | $CH_3$ | $OCH_3$ | |
| 2-637 | 3-Cl | H | H | $CH_3$ | $OCH_3$ | |
| 2-638 | 4-Cl | H | H | $CH_3$ | $OCH_3$ | |
| 2-639 | 3-Br | H | H | $CH_3$ | $OCH_3$ | |
| 2-640 | 4-Br | H | H | $CH_3$ | $OCH_3$ | |
| 2-641 | 3-$CH_3$ | H | H | $CH_3$ | $OCH_3$ | |
| 2-642 | 4-$CH_3$ | H | H | $CH_3$ | $OCH_3$ | |
| 2-643 | 3-$C_2H_5$ | H | H | $CH_3$ | $OCH_3$ | |
| 2-644 | 4-$C_2H_5$ | H | H | $CH_3$ | $OCH_3$ | |
| 2-645 | 3-$OCH_3$ | H | H | $CH_3$ | $OCH_3$ | |
| 2-646 | 4-$OCH_3$ | H | H | $CH_3$ | $OCH_3$ | |
| 2-647 | 3-$CF_3$ | H | H | $CH_3$ | $OCH_3$ | |
| 2-648 | 4-$CF_3$ | H | H | $CH_3$ | $OCH_3$ | |

TABLE 32

| Comp. No. | Ym | $X^1$ | $X^2$ | $X^3$ | $X^4$ | m.p. (°C) |
|---|---|---|---|---|---|---|
| 2-649 | 3-$COCH_3$ | H | H | $CH_3$ | $OCH_3$ | |
| 2-650 | 4-$COCH_3$ | H | H | $CH_3$ | $OCH_3$ | |
| 2-651 | 2,4-$(CH_3)_2$ | H | H | $CH_3$ | $OCH_3$ | |
| 2-652 | 2,5-$(CH_3)_2$ | H | H | $CH_3$ | $OCH_3$ | |
| 2-653 | 3,4-$(CH_3)_2$ | H | H | $CH_3$ | $OCH_3$ | |
| 2-654 | 3,5-$(CH_3)_2$ | H | H | $CH_3$ | $OCH_3$ | |
| 2-655 | 3,4-$(OCH_3)_2$ | H | H | $CH_3$ | $OCH_3$ | |
| 2-656 | 2,4-$Cl_2$ | H | H | $CH_3$ | $OCH_3$ | |
| 2-657 | 2,5-$Cl_2$ | H | H | $CH_3$ | $OCH_3$ | |
| 2-658 | 3,4-$Cl_2$ | H | H | $CH_3$ | $OCH_3$ | |
| 2-659 | 2,4-$F_2$ | H | H | $CH_3$ | $OCH_3$ | |
| 2-660 | 2,5-$F_2$ | H | H | $CH_3$ | $OCH_3$ | |
| 2-661 | 3,4-$F_2$ | H | H | $CH_3$ | $OCH_3$ | |
| 2-662 | 2-F, 4-Cl | H | H | $CH_3$ | $OCH_3$ | |
| 2-663 | 3-F, 4-Cl | H | H | $CH_3$ | $OCH_3$ | |
| 2-664 | 3-Cl, 4-F | H | H | $CH_3$ | $OCH_3$ | |
| 2-665 | 2,4-$(CH_3)_2$ | H | H | $CH_3$ | $OCH_3$ | |
| 2-666 | 2,5-$(CH_3)_2$ | H | H | $CH_3$ | $OCH_3$ | |
| 2-667 | 2-F, 4-$CH_3$ | H | H | $CH_3$ | $OCH_3$ | |
| 2-668 | 2-Cl, 4-$CH_3$ | H | H | $CH_3$ | $OCH_3$ | |
| 2-669 | 2-F, 5-$CH_3$ | H | H | $CH_3$ | $OCH_3$ | |
| 2-670 | 2-Cl, 5-$CH_3$ | H | H | $CH_3$ | $OCH_3$ | |
| 2-671 | 2-$OCH_3$, 5-$CH_3$ | H | H | $CH_3$ | $OCH_3$ | |
| 2-672 | 3-$CF_3$, 4-F | H | H | $CH_3$ | $OCH_3$ | |
| 2-673 | 3-$CF_3$, 4-Cl | H | H | $CH_3$ | $OCH_3$ | |
| 2-674 | 3-F, 5-$CF_3$ | H | H | $CH_3$ | $OCH_3$ | |
| 2-675 | 2-F, 5-$CF_3$ | H | H | $CH_3$ | $OCH_3$ | |
| 2-676 | 2-Cl, 5-$CF_3$ | H | H | $CH_3$ | $OCH_3$ | |
| 2-677 | 2-F, 3-$CF_3$ | H | H | $CH_3$ | $OCH_3$ | |
| 2-678 | 2-F, 4-$CF_3$ | H | H | $CH_3$ | $OCH_3$ | |
| 2-679 | H | H | H | Cl | $OCH_3$ | |

TABLE 33

| Comp. No. | Ym | X¹ | X² | X³ | X⁴ | m.p. (° C.) |
|---|---|---|---|---|---|---|
| 2-680 | 3-F | H | H | Cl | OCH$_3$ | |
| 2-681 | 4-F | H | H | Cl | OCH$_3$ | |
| 2-682 | 3-Cl | H | H | Cl | OCH$_3$ | |
| 2-683 | 4-Cl | H | H | Cl | OCH$_3$ | |
| 2-684 | 3-Br | H | H | Cl | OCH$_3$ | |
| 2-685 | 4-Br | H | H | Cl | OCH$_3$ | I |
| 2-686 | 3-CH$_3$ | H | H | Cl | OCH$_3$ | |
| 2-687 | 4-CH$_3$ | H | H | Cl | OCH$_3$ | |
| 2-688 | 3-C$_2$H$_5$ | H | H | Cl | OCH$_3$ | |
| 2-689 | 4-C$_2$H$_5$ | H | H | Cl | OCH$_3$ | |
| 2-690 | 3-OCH$_3$ | H | H | Cl | OCH$_3$ | |
| 2-691 | 4-OCH$_3$ | H | H | Cl | OCH$_3$ | |
| 2-692 | 3-CF$_3$ | H | H | Cl | OCH$_3$ | |
| 2-693 | 4-CF$_3$ | H | H | Cl | OCH$_3$ | |
| 2-694 | 3-COCH$_3$ | H | H | Cl | OCH$_3$ | |
| 2-695 | 4-COCH$_3$ | H | H | Cl | OCH$_3$ | |
| 2-696 | 2,4-(CH$_3$)$_2$ | H | H | Cl | OCH$_3$ | |
| 2-697 | 2,5-(CH$_3$)$_2$ | H | H | Cl | OCH$_3$ | |
| 2-698 | 3,4-(CH$_3$)$_2$ | H | H | Cl | OCH$_3$ | |
| 2-699 | 3,5-(CH$_3$)$_2$ | H | H | Cl | OCH$_3$ | |
| 2-700 | 3,4-(OCH$_3$)$_2$ | H | H | Cl | OCH$_3$ | |
| 2-701 | 2,4-Cl$_2$ | H | H | Cl | OCH$_3$ | |
| 2-702 | 2,5-Cl$_2$ | H | H | Cl | OCH$_3$ | |
| 2-703 | 3,4-Cl$_2$ | H | H | Cl | OCH$_3$ | |
| 2-704 | 2,4-F$_2$ | H | H | Cl | OCH$_3$ | |
| 2-705 | 2,5-F$_2$ | H | H | Cl | OCH$_3$ | |
| 2-706 | 3,4-F$_2$ | H | H | Cl | OCH$_3$ | |
| 2-707 | 2-F, 4-Cl | H | H | Cl | OCH$_3$ | |
| 2-708 | 3-F, 4-Cl | H | H | Cl | OCH$_3$ | |
| 2-709 | 3-Cl, 4-F | H | H | Cl | OCH$_3$ | |
| 2-710 | 2,4-(CH$_3$)$_2$ | H | H | Cl | OCH$_3$ | |

TABLE 34

| Comp. No. | Ym | X¹ | X² | X³ | X⁴ | m.p. (° C.) |
|---|---|---|---|---|---|---|
| 2-711 | 2,5-(CH$_3$)$_2$ | H | H | Cl | OCH$_3$ | |
| 2-712 | 2-F, 4-CH$_3$ | H | H | Cl | OCH$_3$ | |
| 2-713 | 2-Cl, 4-CH$_3$ | H | H | Cl | OCH$_3$ | |
| 2-714 | 2-F, 5-CH$_3$ | H | H | Cl | OCH$_3$ | |
| 2-715 | 2-Cl, 5-CH$_3$ | H | H | Cl | OCH$_3$ | |
| 2-716 | 2-OCH$_3$, 5-CH$_3$ | H | H | Cl | OCH$_3$ | |
| 2-717 | 3-CF$_3$, 4-F | H | H | Cl | OCH$_3$ | |
| 2-718 | 3-CF$_3$, 4-Cl | H | H | Cl | OCH$_3$ | |
| 2-719 | 3-F, 5-CF$_3$ | H | H | Cl | OCH$_3$ | |
| 2-720 | 2-F, 5-CF$_3$ | H | H | Cl | OCH$_3$ | |
| 2-721 | 2-Cl, 5-CF$_3$ | H | H | Cl | OCH$_3$ | |
| 2-722 | 2-F, 3-CF$_3$ | H | H | Cl | OCH$_3$ | |
| 2-723 | 2-F, 4-CF$_3$ | H | H | Cl | OCH$_3$ | |

TABLE 35

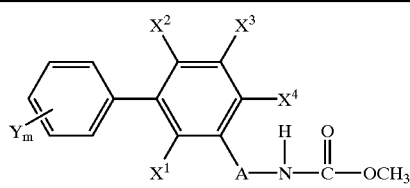

| Comp. No. | Ym | X¹ | X² | X³ | X⁴ | A | m.p. (° C.) |
|---|---|---|---|---|---|---|---|
| 3-1 | H | H | H | H | H | CH(CH$_3$) | oily |
| 3-2 | 3-F | H | H | H | H | CH(CH$_3$) | |
| 3-3 | 4-F | H | H | H | H | CH(CH$_3$) | |
| 3-4 | 3-Cl | H | H | H | H | CH(CH$_3$) | |
| 3-5 | 4-Cl | H | H | H | H | CH(CH$_3$) | 105–107 |
| 3-6 | 3-CH$_3$ | H | H | H | H | CH(CH$_3$) | oily |
| 3-7 | 4-CH$_3$ | H | H | H | H | CH(CH$_3$) | 99–101 |
| 3-8 | 3-C$_2$H$_5$ | H | H | H | H | CH(CH$_3$) | |
| 3-9 | 4-C$_2$H$_5$ | H | H | H | H | CH(CH$_3$) | |
| 3-10 | 3-C$_3$H$_7$-i | H | H | H | H | CH(CH$_3$) | |
| 3-11 | 4-C$_3$H$_7$-i | H | H | H | H | CH(CH$_3$) | |
| 3-12 | 3-C$_4$H$_9$-t | H | H | H | H | CH(CH$_3$) | |
| 3-13 | 4-C$_4$H$_9$-t | H | H | H | H | CH(CH$_3$) | |
| 3-14 | 3-OCH$_3$ | H | H | H | H | CH(CH$_3$) | |
| 3-15 | 4-OCH$_3$ | H | H | H | H | CH(CH$_3$) | 117–119 |
| 3-16 | 3-CF$_3$ | H | H | H | H | CH(CH$_3$) | oily |
| 3-17 | 4-CF$_3$ | H | H | H | H | CH(CH$_3$) | 87–89 |
| 3-18 | 2,4-Cl$_2$ | H | H | H | H | CH(CH$_3$) | oily |
| 3-19 | 3,4-Cl$_2$ | H | H | H | H | CH(CH$_3$) | |
| 3-20 | 3,5-Cl$_2$ | H | H | H | H | CH(CH$_3$) | oily |
| 3-21 | 3-Cl,4-F | H | H | H | H | CH(CH$_3$) | 55–58 |
| 3-22 | 3,4-(CH$_3$)$_2$ | H | H | H | H | CH(CH$_3$) | |
| 3-23 | 3,5-(CH$_3$)$_2$ | H | H | H | H | CH(CH$_3$) | |
| 3-24 | 3-OCF$_3$ | H | H | H | H | CH(CH$_3$) | |
| 3-25 | 4-OCF$_3$ | H | H | H | H | CH(CH$_3$) | |
| 3-26 | H | H | H | H | F | CH(CH$_3$) | oily |
| 3-27 | 3-F | H | H | H | F | CH(CH$_3$) | |
| 3-28 | 4-F | H | H | H | F | CH(CH$_3$) | 104–105 |

TABLE 36

| Comp. No. | Ym | X¹ | X² | X³ | X⁴ | A | m.p. (° C.) |
|---|---|---|---|---|---|---|---|
| 3-29 | 3-Cl | H | H | H | F | CH(CH$_3$) | |
| 3-30 | 4-Cl | H | H | H | F | CH(CH$_3$) | 131–134 |
| 3-31 | 3-CH$_3$ | H | H | H | F | CH(CH$_3$) | |
| 3-32 | 4-CH$_3$ | H | H | H | F | CH(CH$_3$) | 106–107 |
| 3-33 | 3-C$_2$H$_5$ | H | H | H | F | CH(CH$_3$) | |
| 3-34 | 4-C$_2$H$_5$ | H | H | H | F | CH(CH$_3$) | |
| 3-35 | 3-C$_3$H$_7$-i | H | H | H | F | CH(CH$_3$) | |
| 3-36 | 4-C$_3$H$_7$-i | H | H | H | F | CH(CH$_3$) | |
| 3-37 | 3-C$_4$H$_9$-t | H | H | H | F | CH(CH$_3$) | |
| 3-38 | 4-C$_4$H$_9$-t | H | H | H | F | CH(CH$_3$) | |
| 3-39 | 3-OCH$_3$ | H | H | H | F | CH(CH$_3$) | |
| 3-40 | 4-OCH$_3$ | H | H | H | F | CH(CH$_3$) | |
| 3-41 | 3-CF$_3$ | H | H | H | F | CH(CH$_3$) | 126–128 |
| 3-42 | 4-CF$_3$ | H | H | H | F | CH(CH$_3$) | 97–100 |
| 3-43 | 2,4-Cl$_2$ | H | H | H | F | CH(CH$_3$) | |
| 3-44 | 3,4-Cl$_2$ | H | H | H | F | CH(CH$_3$) | |
| 3-45 | 3,5-Cl$_2$ | H | H | H | F | CH(CH$_3$) | |
| 3-46 | 3-Cl, 4-F | H | H | H | F | CH(CH$_3$) | |
| 3-47 | 3,4-(CH$_3$)$_2$ | H | H | H | F | CH(CH$_3$) | |
| 3-48 | 3,5-(CH$_3$)$_2$ | H | H | H | F | CH(CH$_3$) | |
| 3-49 | 3-OCF$_3$ | H | H | H | F | CH(CH$_3$) | |
| 3-50 | 4-OCF$_3$ | H | H | H | F | CH(CH$_3$) | |
| 3-51 | H | H | H | H | Cl | CH(CH$_3$) | 130–133 |
| 3-52 | 3-F | H | H | H | Cl | CH(CH$_3$) | |
| 3-53 | 4-F | H | H | H | Cl | CH(CH$_3$) | |
| 3-54 | 3-Cl | H | H | H | Cl | CH(CH$_3$) | |
| 3-55 | 4-Cl | H | H | H | Cl | CH(CH$_3$) | 135–138 |
| 3-56 | 3-CH$_3$ | H | H | H | Cl | CH(CH$_3$) | |
| 3-57 | 4-CH$_3$ | H | H | H | Cl | CH(CH$_3$) | 114–117 |
| 3-58 | 3-C$_2$H$_5$ | H | H | H | Cl | CH(CH$_3$) | |
| 3-59 | 4-C$_2$H$_5$ | H | H | H | Cl | CH(CH$_3$) | |

TABLE 37

| Comp. No. | Ym | X¹ | X² | X³ | X⁴ | A | m.p. (° C.) |
|---|---|---|---|---|---|---|---|
| 3-60 | 3-C₃H₇-i | H | H | H | Cl | CH(CH₃) | |
| 3-61 | 4-C₃H₇-i | H | H | H | Cl | CH(CH₃) | |
| 3-62 | 3-C₄H₉-t | H | H | H | Cl | CH(CH₃) | |
| 3-63 | 4-C₄H₉-t | H | H | H | Cl | CH(CH₃) | |
| 3-64 | 3-OCH₃ | H | H | H | Cl | CH(CH₃) | |
| 3-65 | 4-OCH₃ | H | H | H | Cl | CH(CH₃) | |
| 3-66 | 3-CF₃ | H | H | H | Cl | CH(CH₃) | 143–146 |
| 3-67 | 4-CF₃ | H | H | H | Cl | CH(CH₃) | |
| 3-68 | 2,4-Cl₂ | H | H | H | Cl | CH(CH₃) | |
| 3-69 | 3,4-Cl₂ | H | H | H | Cl | CH(CH₃) | |
| 3-70 | 3,5-Cl₂ | H | H | H | Cl | CH(CH₃) | |
| 3-71 | 3-Cl, 4-F | H | H | H | Cl | CH(CH₃) | |
| 3-72 | 3,4-(CH₃)₂ | H | H | H | Cl | CH(CH₃) | |
| 3-73 | 3,5-(CH₃)₂ | H | H | H | Cl | CH(CH₃) | |
| 3-74 | 3-OCF₃ | H | H | H | Cl | CH(CH₃) | |
| 3-75 | 4-OCF₃ | H | H | H | Cl | CH(CH₃) | |
| 3-76 | H | H | H | H | OCH₃ | CH(CH₃) | 130–131 |
| 3-77 | 3-F | H | H | H | OCH₃ | CH(CH₃) | |
| 3-78 | 4-F | H | H | H | OCH₃ | CH(CH₃) | |
| 3-79 | 3-Cl | H | H | H | OCH₃ | CH(CH₃) | |
| 3-80 | 4-Cl | H | H | H | OCH₃ | CH(CH₃) | 140–143 |
| 3-81 | 3-CH₃ | H | H | H | OCH₃ | CH(CH₃) | |
| 3-82 | 4-CH₃ | H | H | H | OCH₃ | CH(CH₃) | |
| 3-83 | 3-C₂H₅ | H | H | H | OCH₃ | CH(CH₃) | |
| 3-84 | 4-C₂H₅ | H | H | H | OCH₃ | CH(CH₃) | |
| 3-85 | 3-C₃H₇-i | H | H | H | OCH₃ | CH(CH₃) | |
| 3-86 | 4-C₃H₇-i | H | H | H | OCH₃ | CH(CH₃) | |
| 3-87 | 3-C₄H₉-t | H | H | H | OCH₃ | CH(CH₃) | |
| 3-88 | 4-C₄H₉-t | H | H | H | OCH₃ | CH(CH₃) | |
| 3-89 | 3-OCH₃ | H | H | H | OCH₃ | CH(CH₃) | |
| 3-90 | 4-OCH₃ | H | H | H | OCH₃ | CH(CH₃) | |

TABLE 38

| Comp. No. | Ym | X¹ | X² | X³ | X⁴ | A | m.p. (° C.) |
|---|---|---|---|---|---|---|---|
| 3-91 | 3-CF₃ | H | H | H | OCH₃ | CH(CH₃) | |
| 3-92 | 4-CF₃ | H | H | H | OCH₃ | CH(CH₃) | 127–130 |
| 3-93 | 2,4-Cl₂ | H | H | H | OCH₃ | CH(CH₃) | |
| 3-94 | 3,4-Cl₂ | H | H | H | OCH₃ | CH(CH₃) | |
| 3-95 | 3,5-Cl₂ | H | H | H | OCH₃ | CH(CH₃) | |
| 3-96 | 3-Cl, 4-F | H | H | H | OCH₃ | CH(CH₃) | |
| 3-97 | 3,4-(CH₃)₂ | H | H | H | OCH₃ | CH(CH₃) | |
| 3-98 | 3,5-(CH₃)₂ | H | H | H | OCH₃ | CH(CH₃) | |
| 3-99 | 3-OCF₃ | H | H | H | OCH₃ | CH(CH₃) | |
| 3-100 | 4-OCF₃ | H | H | H | OCH₃ | CH(CH₃) | |
| 3-101 | H | H | H | H | H | CH(C₂H₅) | 68–69 |
| 3-102 | 3-F | H | H | H | H | CH(C₂H₅) | |
| 3-103 | 4-F | H | H | H | H | CH(C₂H₅) | |
| 3-104 | 3-Cl | H | H | H | H | CH(C₂H₅) | |
| 3-105 | 4-Cl | H | H | H | H | CH(C₂H₅) | 86–89 |
| 3-106 | 3-CH₃ | H | H | H | H | CH(C₂H₅) | |
| 3-107 | 4-CH₃ | H | H | H | H | CH(C₂H₅) | 79–82 |
| 3-108 | 4-C₂H₅ | H | H | H | H | CH(C₂H₅) | |
| 3-109 | 4-OCH₃ | H | H | H | H | CH(C₂H₅) | |
| 3-110 | 3-CF₃ | H | H | H | H | CH(C₂H₅) | |
| 3-111 | 4-CF₃ | H | H | H | H | CH(C₂H₅) | |
| 3-112 | 3,4-Cl₂ | H | H | H | H | CH(C₂H₅) | |
| 3-113 | 3,5-Cl₂ | H | H | H | H | CH(C₂H₅) | |
| 3-114 | 3-Cl, 4-F | H | H | H | H | CH(C₂H₅) | |
| 3-115 | 3,4-(CH₃)₂ | H | H | H | H | CH(C₂H₅) | |
| 3-116 | 3,5-(CH₃)₂ | H | H | H | H | CH(C₂H₅) | |
| 3-117 | H | H | H | H | F | CH(C₂H₅) | |
| 3-118 | 3-F | H | H | H | F | CH(C₂H₅) | |
| 3-119 | 4-F | H | H | H | F | CH(C₂H₅) | |
| 3-120 | 3-Cl | H | H | H | F | CH(C₂H₅) | |
| 3-121 | 4-Cl | H | H | H | F | CH(C₂H₅) | |

TABLE 39

| Comp. No. | Ym | X¹ | X² | X³ | X⁴ | A | m.p. (° C.) |
|---|---|---|---|---|---|---|---|
| 3-122 | 3-CH₃ | H | H | H | F | CH(C₂H₅) | |
| 3-123 | 4-CH₃ | H | H | H | F | CH(C₂H₅) | |
| 3-124 | 3-C₂H₅ | H | H | H | F | CH(C₂H₅) | |
| 3-125 | 4-C₂H₅ | H | H | H | F | CH(C₂H₅) | |
| 3-126 | 3-OCH₃ | H | H | H | F | CH(C₂H₅) | |
| 3-127 | 4-OCH₃ | H | H | H | F | CH(C₂H₅) | |
| 3-128 | 3-CF₃ | H | H | H | F | CH(C₂H₅) | |
| 3-129 | 4-CF₃ | H | H | H | F | CH(C₂H₅) | |
| 3-130 | 2,4-Cl₂ | H | H | H | F | CH(C₂H₅) | |
| 3-131 | 3,4-Cl₂ | H | H | H | F | CH(C₂H₅) | |
| 3-132 | 3,5-Cl₂ | H | H | H | F | CH(C₂H₅) | |
| 3-133 | 3-Cl, 4-F | H | H | H | F | CH(C₂H₅) | |
| 3-134 | 3,4-(CH₃)₂ | H | H | H | F | CH(C₂H₅) | |
| 3-135 | 3,5-(CH₃)₂ | H | H | H | F | CH(C₂H₅) | |
| 3-136 | 3-OCF₃ | H | H | H | F | CH(C₂H₅) | |
| 3-137 | 4-OCF₃ | H | H | H | F | CH(C₂H₅) | |
| 3-138 | H | H | H | H | Cl | CH(C₂H₅) | |
| 3-139 | 3-F | H | H | H | Cl | CH(C₂H₅) | |
| 3-140 | 4-F | H | H | H | Cl | CH(C₂H₅) | |
| 3-141 | 3-Cl | H | H | H | Cl | CH(C₂H₅) | |
| 3-142 | 4-Cl | H | H | H | Cl | CH(C₂H₅) | |
| 3-143 | 3-CH₃ | H | H | H | Cl | CH(C₂H₅) | |
| 3-144 | 4-CH₃ | H | H | H | Cl | CH(C₂H₅) | |
| 3-145 | 3-C₂H₅ | H | H | H | Cl | CH(C₂H₅) | |
| 3-146 | 4-C₂H₅ | H | H | H | Cl | CH(C₂H₅) | |
| 3-147 | 3-OCH₃ | H | H | H | Cl | CH(C₂H₅) | |
| 3-148 | 4-OCH₃ | H | H | H | Cl | CH(C₂H₅) | |
| 3-149 | 3-CF₃ | H | H | H | Cl | CH(C₂H₅) | |
| 3-150 | 4-CF₃ | H | H | H | Cl | CH(C₂H₅) | |
| 3-151 | 2,4-Cl₂ | H | H | H | Cl | CH(C₂H₅) | |
| 3-152 | 3,4-Cl₂ | H | H | H | Cl | CH(C₂H₅) | |

TABLE 40

| Comp. No. | Ym | X¹ | X² | X³ | X⁴ | A | m.p. (° C.) |
|---|---|---|---|---|---|---|---|
| 3-153 | 3,5-Cl₂ | H | H | H | Cl | CH(C₂H₅) | |
| 3-154 | 3-Cl, 4-F | H | H | H | Cl | CH(C₂H₅) | |
| 3-155 | 3,4-(CH₃)₂ | H | H | H | Cl | CH(C₂H₅) | |
| 3-156 | 3,5-(CH₃)₂ | H | H | H | Cl | CH(C₂H₅) | |
| 3-157 | 3-OCF₃ | H | H | H | Cl | CH(C₂H₅) | |
| 3-158 | 4-OCF₃ | H | H | H | Cl | CH(C₂H₅) | |
| 3-159 | H | H | H | H | H | CH(C₃H₇) | |
| 3-160 | 4-F | H | H | H | H | CH(C₃H₇) | |
| 3-161 | 4-Cl | H | H | H | H | CH(C₃H₇) | |
| 3-162 | 3-CH₃ | H | H | H | H | CH(C₃H₇) | |
| 3-163 | 4-CH₃ | H | H | H | H | CH(C₃H₇) | |
| 3-164 | 4-OCH₃ | H | H | H | H | CH(C₃H₇) | |
| 3-165 | 3-CF₃ | H | H | H | H | CH(C₃H₇) | |
| 3-166 | 4-CF₃ | H | H | H | H | CH(C₃H₇) | |
| 3-167 | 3,4-Cl₂ | H | H | H | H | CH(C₃H₇) | |
| 3-168 | 3,5-Cl₂ | H | H | H | H | CH(C₃H₇) | |
| 3-169 | 3,4-(CH₃)₂ | H | H | H | H | CH(C₃H₇) | |
| 3-170 | 3,5-(CH₃)₂ | H | H | H | H | CH(C₃H₇) | |
| 3-171 | H | H | H | H | F | CH(C₃H₇) | |
| 3-172 | 4-F | H | H | H | F | CH(C₃H₇) | |
| 3-173 | 4-Cl | H | H | H | F | CH(C₃H₇) | |
| 3-174 | 3-CH₃ | H | H | H | F | CH(C₃H₇) | |
| 3-175 | 4-CH₃ | H | H | H | F | CH(C₃H₇) | |
| 3-176 | 4-C₂H₅ | H | H | H | F | CH(C₃H₇) | |
| 3-177 | 4-OCH₃ | H | H | H | F | CH(C₃H₇) | |
| 3-178 | 3-CF₃ | H | H | H | F | CH(C₃H₇) | |
| 3-179 | 4-CF₃ | H | H | H | F | CH(C₃H₇) | |
| 3-180 | 3,4-Cl₂ | H | H | H | F | CH(C₃H₇) | |
| 3-181 | 3,5-Cl₂ | H | H | H | F | CH(C₃H₇) | |
| 3-182 | 3,4-(CH₃)₂ | H | H | H | F | CH(C₃H₇) | |
| 3-183 | 3,5-(CH₃)₂ | H | H | H | F | CH(C₃H₇) | |

TABLE 41

| Comp. No. | Ym | X¹ | X² | X³ | X⁴ | A | m.p. (° C.) |
|---|---|---|---|---|---|---|---|
| 3-184 | H | H | H | H | Cl | CH(C$_3$H$_7$) | |
| 3-185 | 4-F | H | H | H | Cl | CH(C$_3$H$_7$) | |
| 3-186 | 3-Cl | H | H | H | Cl | CH(C$_3$H$_7$) | |
| 3-187 | 4-Cl | H | H | H | Cl | CH(C$_3$H$_7$) | |
| 3-188 | 3-CH$_3$ | H | H | H | Cl | CH(C$_3$H$_7$) | |
| 3-189 | 4-CH$_3$ | H | H | H | Cl | CH(C$_3$H$_7$) | |
| 3-190 | 4-OCH$_3$ | H | H | H | Cl | CH(C$_3$H$_7$) | |
| 3-191 | 3-CF$_3$ | H | H | H | Cl | CH(C$_3$H$_7$) | |
| 3-192 | 4-CF$_3$ | H | H | H | Cl | CH(C$_3$H$_7$) | |
| 3-193 | 3,4-Cl$_2$ | H | H | H | Cl | CH(C$_3$H$_7$) | |
| 3-194 | 3,5-Cl$_2$ | H | H | H | Cl | CH(C$_3$H$_7$) | |
| 3-195 | 3,4-(CH$_3$)$_2$ | H | H | H | Cl | CH(C$_3$H$_7$) | |
| 3-196 | 3,5-(CH$_3$)$_2$ | H | H | H | Cl | CH(C$_3$H$_7$) | |
| 3-197 | H | H | H | H | H | C(CH$_3$)$_2$ | |
| 3-198 | 3-F | H | H | H | H | C(CH$_3$)$_2$ | |
| 3-199 | 4-F | H | H | H | H | C(CH$_3$)$_2$ | |
| 3-200 | 3-Cl | H | H | H | H | C(CH$_3$)$_2$ | |
| 3-201 | 4-Cl | H | H | H | H | C(CH$_3$)$_2$ | |
| 3-202 | 3-CH$_3$ | H | H | H | H | C(CH$_3$)$_2$ | |
| 3-203 | 4-CH$_3$ | H | H | H | H | C(CH$_3$)$_2$ | |
| 3-204 | 3-CF$_3$ | H | H | H | H | C(CH$_3$)$_2$ | |
| 3-205 | 4-CF$_3$ | H | H | H | H | C(CH$_3$)$_2$ | |
| 3-206 | 3,4-Cl$_2$ | H | H | H | H | C(CH$_3$)$_2$ | |
| 3-207 | 3,5-Cl$_2$ | H | H | H | H | C(CH$_3$)$_2$ | |
| 3-208 | 3,4-(CH$_3$)$_2$ | H | H | H | H | C(CH$_3$)$_2$ | |
| 3-209 | 3,5-(CH$_3$)$_2$ | H | H | H | H | C(CH$_3$)$_2$ | |
| 3-210 | H | H | H | H | H | CH$_2$CH$_2$ | |
| 3-211 | 3-F | H | H | H | H | CH$_2$CH$_2$ | |
| 3-212 | 4-F | H | H | H | H | CH$_2$CH$_2$ | |
| 3-213 | 3-Cl | H | H | H | H | CH$_2$CH$_2$ | |
| 3-214 | 4-Cl | H | H | H | H | CH$_2$CH$_2$ | |

TABLE 42

| Comp. No. | Ym | X¹ | X² | X³ | X⁴ | A | m.p. (° C.) |
|---|---|---|---|---|---|---|---|
| 3-215 | 3-CH$_3$ | H | H | H | H | CH$_2$CH$_2$ | |
| 3-216 | 4-CH$_3$ | H | H | H | H | CH$_2$CH$_2$ | |
| 3-217 | 3-CF$_3$ | H | H | H | H | CH$_2$CH$_2$ | |
| 3-218 | 4-CF$_3$ | H | H | H | H | CH$_2$CH$_2$ | |
| 3-219 | 3,4-Cl$_2$ | H | H | H | H | CH$_2$CH$_2$ | |
| 3-220 | 3,5-Cl$_2$ | H | H | H | H | CH$_2$CH$_2$ | |
| 3-221 | 3,4-(CH$_3$)$_2$ | H | H | H | H | CH$_2$CH$_2$ | |
| 3-222 | 3,5-(CH$_3$)$_2$ | H | H | H | H | CH$_2$CH$_2$ | |

TABLE 43

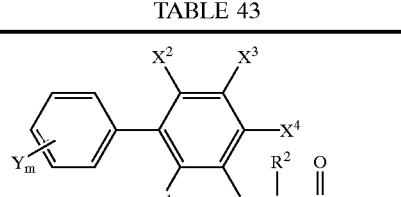

| Comp. No. | Ym | X¹ | X² | X³ | X⁴ | R² | m.p. (° C.) |
|---|---|---|---|---|---|---|---|
| 4-1 | H | CH$_3$ | H | H | H | CH$_3$ | |
| 4-2 | 3-Cl | CH$_3$ | H | H | H | CH$_3$ | |
| 4-3 | 4-Cl | CH$_3$ | H | H | H | CH$_3$ | |
| 4-4 | 3-CH$_3$ | CH$_3$ | H | H | H | CH$_3$ | |
| 4-5 | 4-CH$_3$ | CH$_3$ | H | H | H | CH$_3$ | |
| 4-6 | 3,4-(CH$_3$)$_2$ | CH$_3$ | H | H | H | CH$_3$ | |
| 4-7 | 3,4-Cl$_2$ | CH$_3$ | H | H | H | CH$_3$ | |
| 4-8 | H | CH$_3$ | H | H | H | CH$_2$OCH$_3$ | |
| 4-9 | 3-Cl | CH$_3$ | H | H | H | CH$_2$OCH$_3$ | |
| 4-10 | 4-Cl | CH$_3$ | H | H | H | CH$_2$OCH$_3$ | |
| 4-11 | 3-CH$_3$ | CH$_3$ | H | H | H | CH$_2$OCH$_3$ | |
| 4-12 | 4-CH$_3$ | CH$_3$ | H | H | H | CH$_2$OCH$_3$ | |
| 4-13 | 3,4-(CH$_3$)$_2$ | CH$_3$ | H | H | H | CH$_2$OCH$_3$ | |

TABLE 43-continued

| Comp. No. | Ym | X¹ | X² | X³ | X⁴ | R² | m.p. (° C.) |
|---|---|---|---|---|---|---|---|
| 4-14 | 3,4-Cl$_2$ | CH$_3$ | H | H | H | CH$_2$OCH$_3$ | |
| 4-15 | H | CH$_3$ | H | H | H | CH$_2$CH=CH$_2$ | |
| 4-16 | 3-Cl | CH$_3$ | H | H | H | CH$_2$CH=CH$_2$ | |
| 4-17 | 4-Cl | CH$_3$ | H | H | H | CH$_2$CH=CH$_2$ | |
| 4-18 | 3-CH$_3$ | CH$_3$ | H | H | H | CH$_2$CH=CH$_2$ | |
| 4-19 | 4-CH$_3$ | CH$_3$ | H | H | H | CH$_2$CH=CH$_2$ | |
| 4-20 | 3,4-(CH$_3$)$_2$ | CH$_3$ | H | H | H | CH$_2$CH=CH$_2$ | |
| 4-21 | 3,4-Cl$_2$ | CH$_3$ | H | H | H | CH$_2$CH=CH$_2$ | |
| 4-22 | H | CH$_3$ | H | H | H | OCH$_3$ | oily |
| 4-23 | 3-Cl | CH$_3$ | H | H | H | OCH$_3$ | |
| 4-24 | 4-Cl | CH$_3$ | H | H | H | OCH$_3$ | |
| 4-25 | 3-CH$_3$ | CH$_3$ | H | H | H | OCH$_3$ | |
| 4-26 | 4-CH$_3$ | CH$_3$ | H | H | H | OCH$_3$ | |
| 4-27 | 3,4-(CH$_3$)$_2$ | CH$_3$ | H | H | H | OCH$_3$ | |
| 4-28 | 3,4-Cl$_2$ | CH$_3$ | H | H | H | OCH$_3$ | |

TABLE 44

| Comp. No. | Ym | X¹ | X² | X³ | X⁴ | R² | m.p. (° C.) |
|---|---|---|---|---|---|---|---|
| 4-29 | H | H | Cl | H | H | CH$_3$ | |
| 4-30 | 3-Cl | H | Cl | H | H | CH$_3$ | |
| 4-31 | 4-Cl | H | Cl | H | H | CH$_3$ | |
| 4-32 | 3-CH$_3$ | H | Cl | H | H | CH$_3$ | |
| 4-33 | 4-CH$_3$ | H | Cl | H | H | CH$_3$ | |
| 4-34 | 3,4-(CH$_3$)$_2$ | H | Cl | H | H | CH$_3$ | |
| 4-35 | 3,4-Cl$_2$ | H | Cl | H | H | CH$_3$ | |
| 4-36 | H | H | Cl | H | H | CH$_2$OCH$_3$ | |
| 4-37 | 3-Cl | H | Cl | H | H | CH$_2$OCH$_3$ | |
| 4-38 | 4-Cl | H | Cl | H | H | CH$_2$OCH$_3$ | |
| 4-39 | 3-CH$_3$ | H | Cl | H | H | CH$_2$OCH$_3$ | |
| 4-40 | 4-CH$_3$ | H | Cl | H | H | CH$_2$OCH$_3$ | |
| 4-41 | 3,4-(CH$_3$)$_2$ | H | Cl | H | H | CH$_2$OCH$_3$ | |
| 4-42 | 3,4-Cl$_2$ | H | Cl | H | H | CH$_2$OCH$_3$ | |
| 4-43 | H | H | Cl | H | H | CH$_2$CH=CH$_2$ | |
| 4-44 | 3-Cl | H | Cl | H | H | CH$_2$CH=CH$_2$ | |
| 4-45 | 4-Cl | H | Cl | H | H | CH$_2$CH=CH$_2$ | |
| 4-46 | 3-CH$_3$ | H | Cl | H | H | CH$_2$CH=CH$_2$ | |
| 4-47 | 4-CH$_3$ | H | Cl | H | H | CH$_2$CH=CH$_2$ | |
| 4-48 | 3,4-(CH$_3$)$_2$ | H | Cl | H | H | CH$_2$CH=CH$_2$ | |
| 4-49 | 3,4-Cl$_2$ | H | Cl | H | H | CH$_2$CH=CH$_2$ | |
| 4-50 | H | H | Cl | H | H | OCH$_3$ | |
| 4-51 | 3-Cl | H | Cl | H | H | OCH$_3$ | |
| 4-52 | 4-Cl | H | Cl | H | H | OCH$_3$ | |
| 4-53 | 3-CH$_3$ | H | Cl | H | H | OCH$_3$ | |
| 4-54 | 4-CH$_3$ | H | Cl | H | H | OCH$_3$ | |
| 4-55 | 3,4-(CH$_3$)$_2$ | H | Cl | H | H | OCH$_3$ | |
| 4-56 | 3,4-Cl$_2$ | H | Cl | H | H | OCH$_3$ | |
| 4-57 | H | H | OCH$_3$ | H | H | CH$_3$ | |
| 4-58 | 3-Cl | H | OCH$_3$ | H | H | CH$_3$ | |
| 4-59 | 4-Cl | H | OCH$_3$ | H | H | CH$_3$ | |

TABLE 45

| Comp. No. | Ym | X¹ | R² | X³ | X⁴ | R² | m.p. (° C.) |
|---|---|---|---|---|---|---|---|
| 4-60 | 3-CH$_3$ | H | OCH$_3$ | H | H | CH$_3$ | |
| 4-61 | 4-CH$_3$ | H | OCH$_3$ | H | H | CH$_3$ | |

TABLE 45-continued

| Comp. No. | Ym | X¹ | R² | X³ | X⁴ | R² | m.p. (°C.) |
|---|---|---|---|---|---|---|---|
| 4-62 | 3,4-(CH$_3$)$_2$ | H | OCH$_3$ | H | H | CH$_3$ | |
| 4-63 | 3,4-Cl$_2$ | H | OCH$_3$ | H | H | CH$_3$ | |
| 4-64 | H | H | OCH$_3$ | H | H | CH$_2$OCH$_3$ | |
| 4-65 | 3-Cl | H | OCH$_3$ | H | H | CH$_2$OCH$_3$ | |
| 4-66 | 4-Cl | H | OCH$_3$ | H | H | CH$_2$OCH$_3$ | |
| 4-67 | 3-CH$_3$ | H | OCH$_3$ | H | H | CH$_2$OCH$_3$ | |
| 4-68 | 4-CH$_3$ | H | OCH$_3$ | H | H | CH$_2$OCH$_3$ | |
| 4-69 | 3,4-(CH$_3$)$_2$ | H | OCH$_3$ | H | H | CH$_2$OCH$_3$ | |
| 4-70 | 3,4-Cl$_2$ | H | OCH$_3$ | H | H | CH$_2$OCH$_3$ | |
| 4-71 | H | H | OCH$_3$ | H | H | CH$_2$CH=CH$_2$ | |
| 4-72 | 3-Cl | H | OCH$_3$ | H | H | CH$_2$CH=CH$_2$ | |
| 4-73 | 4-Cl | H | OCH$_3$ | H | H | CH$_2$CH=CH$_2$ | |
| 4-74 | 3-CH$_3$ | H | OCH$_3$ | H | H | CH$_2$CH=CH$_2$ | |
| 4-75 | 4-CH$_3$ | H | OCH$_3$ | H | H | CH$_2$CH=CH$_2$ | |
| 4-76 | 3,4-(CH$_3$)$_2$ | H | OCH$_3$ | H | H | CH$_2$CH=CH$_2$ | |
| 4-77 | 3,4-Cl$_2$ | H | OCH$_3$ | H | H | CH$_2$CH=CH$_2$ | |
| 4-78 | H | H | OCH$_3$ | H | H | OCH$_3$ | |
| 4-79 | 3-Cl | H | OCH$_3$ | H | H | OCH$_3$ | |
| 4-80 | 4-Cl | H | OCH$_3$ | H | H | OCH$_3$ | |
| 4-81 | 3-CH$_3$ | H | OCH$_3$ | H | H | OCH$_3$ | |
| 4-82 | 4-CH$_3$ | H | OCH$_3$ | H | H | OCH$_3$ | |
| 4-83 | 3,4-(CH$_3$)$_2$ | H | OCH$_3$ | H | H | OCH$_3$ | |
| 4-84 | 3,4-Cl$_2$ | H | OCH$_3$ | H | H | OCH$_3$ | |
| 4-85 | H | H | H | H | F | CH$_3$ | |
| 4-86 | 3-Cl | H | H | H | F | CH$_3$ | |
| 4-87 | 4-Cl | H | H | H | F | CH$_3$ | |
| 4-88 | 3-CH$_3$ | H | H | H | F | CH$_3$ | |
| 4-89 | 4-CH$_3$ | H | H | H | F | CH$_3$ | |
| 4-90 | 3-C$_2$H$_5$ | H | H | H | F | CH$_3$ | |

TABLE 46

| Comp. No. | Ym | X¹ | X² | X³ | X⁴ | R² | m.p. (°C.) |
|---|---|---|---|---|---|---|---|
| 4-91 | 4-C$_2$H$_5$ | H | H | H | F | CH$_3$ | |
| 4-92 | 3-CF$_3$ | H | H | H | F | CH$_3$ | |
| 4-93 | 4-CF$_3$ | H | H | H | F | CH$_3$ | |
| 4-94 | 3-OCH$_3$ | H | H | H | F | CH$_3$ | |
| 4-95 | 4-OCH$_3$ | H | H | H | F | CH$_3$ | |
| 4-96 | 3-OCF$_3$ | H | H | H | F | CH$_3$ | |
| 4-97 | 4-OCF$_3$ | H | H | H | F | CH$_3$ | |
| 4-98 | 3,4-Cl$_2$ | H | H | H | F | CH$_3$ | |
| 4-99 | 3,4-(CH$_3$)$_2$ | H | H | H | F | CH$_3$ | |
| 4-100 | 3,5-(CH$_3$)$_2$ | H | H | H | F | CH$_3$ | |
| 4-101 | H | H | H | H | F | CH$_2$CH=CH$_2$ | |
| 4-102 | 3-Cl | H | H | H | F | CH$_2$CH=CH$_2$ | |
| 4-103 | 4-Cl | H | H | H | F | CH$_2$CH=CH$_2$ | |
| 4-104 | 3-CH$_3$ | H | H | H | F | CH$_2$CH=CH$_2$ | |
| 4-105 | 4-CH$_3$ | H | H | H | F | CH$_2$CH=CH$_2$ | |
| 4-106 | 3-C$_2$H$_5$ | H | H | H | F | CH$_2$CH=CH$_2$ | |
| 4-107 | 4-C$_2$H$_5$ | H | H | H | F | CH$_2$CH=CH$_2$ | |
| 4-108 | 3-CF$_3$ | H | H | H | F | CH$_2$CH=CH$_2$ | |
| 4-109 | 4-CF$_3$ | H | H | H | F | CH$_2$CH=CH$_2$ | |
| 4-110 | 3-OCH$_3$ | H | H | H | F | CH$_2$CH=CH$_2$ | |
| 4-111 | 4-OCH$_3$ | H | H | H | F | CH$_2$CH=CH$_2$ | |
| 4-112 | 3-OCF$_3$ | H | H | H | F | CH$_2$CH=CH$_2$ | |
| 4-113 | 4-OCF$_3$ | H | H | H | F | CH$_2$CH=CH$_2$ | |
| 4-114 | 3,4-Cl$_2$ | H | H | H | F | CH$_2$CH=CH$_2$ | |
| 4-115 | 3,4-(CH$_3$)$_2$ | H | H | H | F | CH$_2$CH=CH$_2$ | |
| 4-116 | 3,5-(CH$_3$)$_2$ | H | H | H | F | CH$_2$CH=CH$_2$ | |
| 4-117 | H | H | H | H | F | CH$_2$C≡CH | |
| 4-118 | 3-Cl | H | H | H | F | CH$_2$C≡CH | |
| 4-119 | 4-Cl | H | H | H | F | CH$_2$C≡CH | |
| 4-120 | 3-CH$_3$ | H | H | H | F | CH$_2$C≡CH | |
| 4-121 | 4-CH$_3$ | H | H | H | F | CH$_2$C≡CH | |

TABLE 47

| Comp. No. | Ym | X¹ | X² | X³ | X⁴ | R² | m.p. (°C.) |
|---|---|---|---|---|---|---|---|
| 4-122 | 3-C$_2$H$_5$ | H | H | H | F | CH$_2$C≡CH | |
| 4-123 | 4-C$_2$H$_5$ | H | H | H | F | CH$_2$C≡CH | |
| 4-124 | 3-CF$_3$ | H | H | H | F | CH$_2$C≡CH | |
| 4-125 | 4-CF$_3$ | H | H | H | F | CH$_2$C≡CH | |
| 4-126 | 3-OCH$_3$ | H | H | H | F | CH$_2$C≡CH | |
| 4-127 | 4-OCH$_3$ | H | H | H | F | CH$_2$C≡CH | |
| 4-128 | 3-OCF$_3$ | H | H | H | F | CH$_2$C≡CH | |
| 4-129 | 4-OCF$_3$ | H | H | H | F | CH$_2$C≡CH | |
| 4-130 | 3,4-Cl$_2$ | H | H | H | F | CH$_2$C≡CH | |
| 4-131 | 3,4-(CH$_3$)$_2$ | H | H | H | F | CH$_2$C≡CH | |
| 4-132 | 3,5-(CH$_3$)$_2$ | H | H | H | F | CH$_2$C≡CH | |
| 4-133 | H | H | H | H | F | OCH$_3$ | |
| 4-134 | 3-Cl | H | H | H | F | OCH$_3$ | |
| 4-135 | 4-Cl | H | H | H | F | OCH$_3$ | |
| 4-136 | 3-CH$_3$ | H | H | H | F | OCH$_3$ | |
| 4-137 | 4-CH$_3$ | H | H | H | F | OCH$_3$ | |
| 4-138 | 3-C$_2$H$_5$ | H | H | H | F | OCH$_3$ | |
| 4-139 | 4-C$_2$H$_5$ | H | H | H | F | OCH$_3$ | |
| 4-140 | 3-CF$_3$ | H | H | H | F | OCH$_3$ | |
| 4-141 | 4-CF$_3$ | H | H | H | F | OCH$_3$ | |
| 4-142 | 3-OCH$_3$ | H | H | H | F | OCH$_3$ | |
| 4-143 | 4-OCH$_3$ | H | H | H | F | OCH$_3$ | |
| 4-144 | 3-OCF$_3$ | H | H | H | F | OCH$_3$ | |
| 4-145 | 4-OCF$_3$ | H | H | H | F | OCH$_3$ | |
| 4-146 | 3,4-Cl$_2$ | H | H | H | F | OCH$_3$ | |
| 4-147 | 3,4-(CH$_3$)$_2$ | H | H | H | F | OCH$_3$ | |
| 4-148 | 3,5-(CH$_3$)$_2$ | H | H | H | F | OCH$_3$ | |
| 4-149 | H | H | H | H | Cl | CH$_3$ | |
| 4-150 | 3-Cl | H | H | H | Cl | CH$_3$ | |
| 4-151 | 4-Cl | H | H | H | Cl | CH$_3$ | |
| 4-152 | 3-CH$_3$ | H | H | H | Cl | CH$_3$ | |

TABLE 48

| Comp. No. | Ym | X¹ | X² | X³ | X⁴ | R² | m.p. (°C.) |
|---|---|---|---|---|---|---|---|
| 4-153 | 4-CH$_3$ | H | H | H | Cl | CH$_3$ | |
| 4-154 | 3-C$_2$H$_5$ | H | H | H | Cl | CH$_3$ | |
| 4-155 | 4-C$_2$H$_5$ | H | H | H | Cl | CH$_3$ | |
| 4-156 | 3-CF$_3$ | H | H | H | Cl | CH$_3$ | |
| 4-157 | 4-CF$_3$ | H | H | H | Cl | CH$_3$ | |
| 4-158 | 3-OCH$_3$ | H | H | H | Cl | CH$_3$ | |
| 4-159 | 4-OCH$_3$ | H | H | H | Cl | CH$_3$ | |
| 4-160 | 3-OCF$_3$ | H | H | H | Cl | CH$_3$ | |
| 4-161 | 4-OCF$_3$ | H | H | H | Cl | CH$_3$ | |
| 4-162 | 3,4-Cl$_2$ | H | H | H | Cl | CH$_3$ | |
| 4-163 | 3,4-(CH$_3$)$_2$ | H | H | H | Cl | CH$_3$ | |
| 4-164 | 3,5-(CH$_3$)$_2$ | H | H | H | Cl | CH$_3$ | |
| 4-165 | H | H | H | H | Cl | CH$_2$CH=CH$_2$ | |
| 4-166 | 3-Cl | H | H | H | Cl | CH$_2$CH=CH$_2$ | |
| 4-167 | 4-Cl | H | H | H | Cl | CH$_2$CH=CH$_2$ | |
| 4-168 | 3-CH$_3$ | H | H | H | Cl | CH$_2$CH=CH$_2$ | |
| 4-169 | 4-CH$_3$ | H | H | H | Cl | CH$_2$CH=CH$_2$ | |
| 4-170 | 3-C$_2$H$_5$ | H | H | H | Cl | CH$_2$CH=CH$_2$ | |
| 4-171 | 4-C$_2$H$_5$ | H | H | H | Cl | CH$_2$CH=CH$_2$ | |
| 4-172 | 3-CF$_3$ | H | H | H | Cl | CH$_2$CH=CH$_2$ | |
| 4-173 | 4-CF$_3$ | H | H | H | Cl | CH$_2$CH=CH$_2$ | |
| 4-174 | 3-OCH$_3$ | H | H | H | Cl | CH$_2$CH=CH$_2$ | |
| 4-175 | 4-OCH$_3$ | H | H | H | Cl | CH$_2$CH=CH$_2$ | |
| 4-176 | 3-OCF$_3$ | H | H | H | Cl | CH$_2$CH=CH$_2$ | |
| 4-177 | 4-OCF$_3$ | H | H | H | Cl | CH$_2$CH=CH$_2$ | |
| 4-178 | 3,4-Cl$_2$ | H | H | H | Cl | CH$_2$CH=CH$_2$ | |
| 4-179 | 3,4-(CH$_3$)$_2$ | H | H | H | Cl | CH$_2$CH=CH$_2$ | |
| 4-180 | 3,5-(CH$_3$)$_2$ | H | H | H | Cl | CH$_2$CH=CH$_2$ | |
| 4-181 | H | H | H | H | Cl | CH$_2$C≡CH | |
| 4-182 | 3-Cl | H | H | H | Cl | CH$_2$C≡CH | |
| 4-183 | 4-Cl | H | H | H | Cl | CH$_2$C≡CH | |

TABLE 49

| Comp. No. | Ym | $X^1$ | $X^2$ | $X^3$ | $X^4$ | $R^2$ | m.p. (° C.) |
|---|---|---|---|---|---|---|---|
| 4-184 | 3-$CH_3$ | H | H | H | Cl | $CH_2C\equiv CH$ | |
| 4-185 | 4-$CH_3$ | H | H | H | Cl | $CH_2C\equiv CH$ | |
| 4-186 | 3-$C_2H_5$ | H | H | H | Cl | $CH_2C\equiv CH$ | |
| 4-187 | 4-$C_2H_5$ | H | H | H | Cl | $CH_2C\equiv CH$ | |
| 4-188 | 3-$CF_3$ | H | H | H | Cl | $CH_2C\equiv CH$ | |
| 4-189 | 4-$CF_3$ | H | H | H | Cl | $CH_2C\equiv CH$ | |
| 4-190 | 3-$OCH_3$ | H | H | H | Cl | $CH_2C\equiv CH$ | |
| 4-191 | 4-$OCH_3$ | H | H | H | Cl | $CH_2C\equiv CH$ | |
| 4-192 | 3-$OCF_3$ | H | H | H | Cl | $CH_2C\equiv CH$ | |
| 4-193 | 4-$OCF_3$ | H | H | H | Cl | $CH_2C\equiv CH$ | |
| 4-194 | 3,4-$Cl_2$ | H | H | H | Cl | $CH_2C\equiv CH$ | |
| 4-195 | 3,4-$(CH_3)_2$ | H | H | H | Cl | $CH_2C\equiv CH$ | |
| 4-196 | 3,5-$(CH_3)_2$ | H | H | H | Cl | $CH_2C\equiv CH$ | |
| 4-197 | H | H | H | H | Cl | $OCH_3$ | |
| 4-198 | 3-Cl | H | H | H | Cl | $OCH_3$ | |
| 4-199 | 4-Cl | H | H | H | Cl | $OCH_3$ | oily |
| 4-200 | 3-$CH_3$ | H | H | H | Cl | $OCH_3$ | |
| 4-201 | 4-$CH_3$ | H | H | H | Cl | $OCH_3$ | oily |
| 4-202 | 3-$C_2H_5$ | H | H | H | Cl | $OCH_3$ | |
| 4-203 | 4-$C_2H_5$ | H | H | H | Cl | $OCH_3$ | |
| 4-204 | 3-$CF_3$ | H | H | H | Cl | $OCH_3$ | |
| 4-205 | 4-$CF_3$ | H | H | H | Cl | $OCH_3$ | |
| 4-206 | 3-$OCH_3$ | H | H | H | Cl | $OCH_3$ | |
| 4-207 | 4-$OCH_3$ | H | H | H | Cl | $OCH_3$ | |
| 4-208 | 3-$OCF_3$ | H | H | H | Cl | $OCH_3$ | |
| 4-209 | 4-$OCF_3$ | H | H | H | Cl | $OCH_3$ | |
| 4-210 | 3,4-$Cl_2$ | H | H | H | Cl | $OCH_3$ | |
| 4-211 | 3,4-$(CH_3)_2$ | H | H | H | Cl | $OCH_3$ | |
| 4-212 | 3,5-$(CH_3)_2$ | H | H | H | Cl | $OCH_3$ | |
| 4-213 | H | H | H | H | $CH_3$ | $CH_3$ | |
| 4-214 | 3-Cl | H | H | H | $CH_3$ | $CH_3$ | |

TABLE 50

| Comp. No. | Ym | $X^1$ | $X^2$ | $X^3$ | $X^4$ | $R^2$ | m.p. (° C.) |
|---|---|---|---|---|---|---|---|
| 4-215 | 4-Cl | H | H | H | $CH_3$ | $CH_3$ | |
| 4-216 | 3-$CH_3$ | H | H | H | $CH_3$ | $CH_3$ | |
| 4-217 | 4-$CH_3$ | H | H | H | $CH_3$ | $CH_3$ | |
| 4-218 | 3-$C_2H_5$ | H | H | H | $CH_3$ | $CH_3$ | |
| 4-219 | 4-$C_2H_5$ | H | H | H | $CH_3$ | $CH_3$ | |
| 4-220 | 3-$CF_3$ | H | H | H | $CH_3$ | $CH_3$ | |
| 4-221 | 4-$CF_3$ | H | H | H | $CH_3$ | $CH_3$ | |
| 4-222 | 3-$OCH_3$ | H | H | H | $CH_3$ | $CH_3$ | |
| 4-223 | 4-$OCH_3$ | H | H | H | $CH_3$ | $CH_3$ | |
| 4-224 | 3-$OCF_3$ | H | H | H | $CH_3$ | $CH_3$ | |
| 4-225 | 4-$OCF_3$ | H | H | H | $CH_3$ | $CH_3$ | |
| 4-226 | 3,4-$Cl_2$ | H | H | H | $CH_3$ | $CH_3$ | |
| 4-227 | 3,4-$(CH_3)_2$ | H | H | H | $CH_3$ | $CH_3$ | |
| 4-228 | 3,5-$(CH_3)_2$ | H | H | H | $CH_3$ | $CH_3$ | |
| 4-229 | H | H | H | H | $CH_3$ | $CH_2CH=CH_2$ | |
| 4-230 | 3-Cl | H | H | H | $CH_3$ | $CH_2CH=CH_2$ | |
| 4-231 | 4-Cl | H | H | H | $CH_3$ | $CH_2CH=CH_2$ | |
| 4-232 | 3-$CH_3$ | H | H | H | $CH_3$ | $CH_2CH=CH_2$ | |
| 4-233 | 4-$CH_3$ | H | H | H | $CH_3$ | $CH_2CH=CH_2$ | |
| 4-234 | 3-$C_2H_5$ | H | H | H | $CH_3$ | $CH_2CH=CH_2$ | |
| 4-235 | 4-$C_2H_5$ | H | H | H | $CH_3$ | $CH_2CH=CH_2$ | |
| 4-236 | 3-$CF_3$ | H | H | H | $CH_3$ | $CH_2CH=CH_2$ | |
| 4-237 | 4-$CF_3$ | H | H | H | $CH_3$ | $CH_2CH=CH_2$ | |
| 4-238 | 3-$OCH_3$ | H | H | H | $CH_3$ | $CH_2CH=CH_2$ | |
| 4-239 | 4-$OCH_3$ | H | H | H | $CH_3$ | $CH_2CH=CH_2$ | |
| 4-240 | 3-$OCF_3$ | H | H | H | $CH_3$ | $CH_2CH=CH_2$ | |
| 4-241 | 4-$OCF_3$ | H | H | H | $CH_3$ | $CH_2CH=CH_2$ | |
| 4-242 | 3,4-$Cl_2$ | H | H | H | $CH_3$ | $CH_2CH=CH_2$ | |
| 4-243 | 3,4-$(CH_3)_2$ | H | H | H | $CH_3$ | $CH_2CH=CH_2$ | |
| 4-244 | 3,5-$(CH_3)_2$ | H | H | H | $CH_3$ | $CH_2CH=CH_2$ | |
| 4-245 | H | H | H | H | $CH_3$ | $CH_2C\equiv CH$ | |

TABLE 51

| Comp. No. | Ym | $X^1$ | $X^2$ | $X^3$ | $X^4$ | $R^2$ | m.p. (° C.) |
|---|---|---|---|---|---|---|---|
| 4-246 | 3-Cl | H | H | H | $CH_3$ | $CH_2C\equiv CH$ | |
| 4-247 | 4-Cl | H | H | H | $CH_3$ | $CH_2C\equiv CH$ | |
| 4-248 | 3-$CH_3$ | H | H | H | $CH_3$ | $CH_2C\equiv CH$ | |
| 4-249 | 4-$CH_3$ | H | H | H | $CH_3$ | $CH_2C\equiv CH$ | |
| 4-250 | 3-$C_2H_5$ | H | H | H | $CH_3$ | $CH_2C\equiv CH$ | |
| 4-251 | 4-$C_2H_5$ | H | H | H | $CH_3$ | $CH_2C\equiv CH$ | |
| 4-252 | 3-$CF_3$ | H | H | H | $CH_3$ | $CH_2C\equiv CH$ | |
| 4-253 | 4-$CF_3$ | H | H | H | $CH_3$ | $CH_2C\equiv CH$ | |
| 4-254 | 3-$OCH_3$ | H | H | H | $CH_3$ | $CH_2C\equiv CH$ | |
| 4-255 | 4-$OCH_3$ | H | H | H | $CH_3$ | $CH_2C\equiv CH$ | |
| 4-256 | 3-$OCF_3$ | H | H | H | $CH_3$ | $CH_2C\equiv CH$ | |
| 4-257 | 4-$OCF_3$ | H | H | H | $CH_3$ | $CH_2C\equiv CH$ | |
| 4-258 | 3,4-$Cl_2$ | H | H | H | $CH_3$ | $CH_2C\equiv CH$ | |
| 4-259 | 3,4-$(CH_3)_2$ | H | H | H | $CH_3$ | $CH_2C\equiv CH$ | |
| 4-260 | 3,5-$(CH_3)_2$ | H | H | H | $CH_3$ | $CH_2C\equiv CH$ | |
| 4-261 | H | H | H | H | $CH_3$ | $OCH_3$ | |
| 4-262 | 3-Cl | H | H | H | $CH_3$ | $OCH_3$ | |
| 4-263 | 4-Cl | H | H | H | $CH_3$ | $OCH_3$ | |
| 4-264 | 3-$CH_3$ | H | H | H | $CH_3$ | $OCH_3$ | |
| 4-265 | 4-$CH_3$ | H | H | H | $CH_3$ | $OCH_3$ | |
| 4-266 | 3-$C_2H_5$ | H | H | H | $CH_3$ | $OCH_3$ | |
| 4-267 | 4-$C_2H_5$ | H | H | H | $CH_3$ | $OCH_3$ | |
| 4-268 | 3-$CF_3$ | H | H | H | $CH_3$ | $OCH_3$ | |
| 4-269 | 4-$CF_3$ | H | H | H | $CH_3$ | $OCH_3$ | |
| 4-270 | 3-$OCH_3$ | H | H | H | $CH_3$ | $OCH_3$ | |
| 4-271 | 4-$OCH_3$ | H | H | H | $CH_3$ | $OCH_3$ | |
| 4-272 | 3-$OCF_3$ | H | H | H | $CH_3$ | $OCH_3$ | |
| 4-273 | 4-$OCF_3$ | H | H | H | $CH_3$ | $OCH_3$ | |
| 4-274 | 3,4-$Cl_2$ | H | H | H | $CH_3$ | $OCH_3$ | |
| 4-275 | 3,4-$(CH_3)_2$ | H | H | H | $CH_3$ | $OCH_3$ | |
| 4-276 | 3,5-$(CH_3)_2$ | H | H | H | $CH_3$ | $OCH_3$ | |

TABLE 52

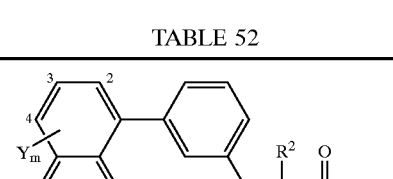

| Comp. No. | Ym | G | $R^1$ | $R^2$ | m.p. (° C.) |
|---|---|---|---|---|---|
| 5-1 | H | O | $CH_3$ | H | 127–130 |
| 5-2 | 4-Cl | O | $CH_3$ | H | |
| 5-3 | 2,4-$Cl_2$ | O | $CH_3$ | H | |
| 5-4 | 2-$CH_3$ | O | $CH_3$ | H | |
| 5-5 | 4-$OCH_3$ | O | $CH_3$ | H | |
| 5-6 | 4-$COCH_3$ | O | $CH_3$ | H | |
| 5-7 | H | O | $CH_3$ | $CH_3$ | |
| 5-8 | H | O | $CH_3$ | $CH_2CH=CH_2$ | |
| 5-9 | H | O | $CH_3$ | $CH_2C\equiv CH$ | |
| 5-10 | H | O | $CH_3$ | $OCH_3$ | |

TABLE 53

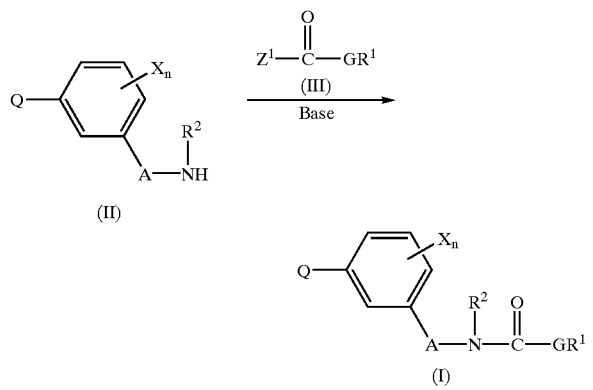

| Comp. No. | Ym | G | R¹ | R² | m.p. (° C.) |
|---|---|---|---|---|---|
| 6-1 | 1-CH₃ | O | CH₃ | H | 84–86 |
| 6-2 | 6-OCH₃ | O | CH₃ | H | |
| 6-3 | 1-COCH₃ | O | CH₃ | H | |
| 6-4 | 3-OCH₃ | O | CH₃ | H | |
| 6-5 | 4-OCH₃ | O | CH₃ | H | |
| 6-6 | H | O | CH₃ | H | |
| 6-7 | H | O | CH₃ | CH₃ | |
| 6-8 | H | O | CH₃ | CH₂CH=CH₂ | |
| 6-9 | H | O | CH₃ | CH₂C≡CH | |
| 6-10 | H | O | CH₃ | OCH₃ | |

Typical processes for production of the biarylalkylenecarbamic acid derivatives as the compounds of the present invention are exemplified below.

Process 1

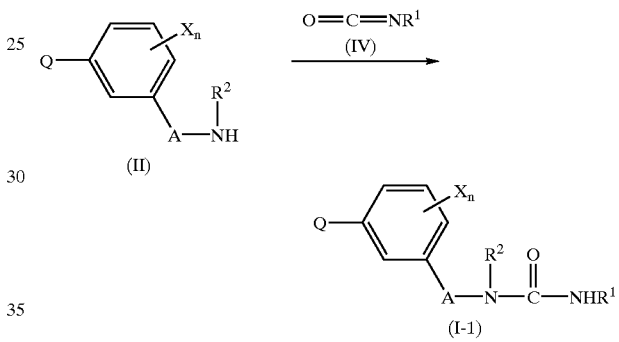

(wherein A, G, Q, R¹, R², X and n are the same as defined above, and Z is a halogen atom.)

A compound (I) of the present invention is obtainable by reaction of a compound (II) with a compound (III) in an inert solvent in the presence of a base.

With respect to the amounts of the starting compounds used in the reaction, the compound (III) relative to the compound (II) is appropriately selected within the range of from 0.5 to 3.0 eq, preferably from 0.8 to 1.5 eq.

As the inert solvent to be used in the reaction, any solvent that does not inhibit the progress of the reaction, and for example, ketones such as acetone, methyl ethyl ketone or cyclohexanone, ethers such as diethyl ether, diisopropyl ether, tetrahydrofuran, dioxane, monoglyme and diglyme, esters such as ethyl acetate and methyl acetate, halogenated hydrocarbons such as dichloroethane, chloroform, carbon tetrachloride and tetrachloroethane, aromatic hydrocarbons such as benzene, chlorobenzene, nitrobenzene and toluene, nitriles such as acetonitrile, N,N-dimethylformamide, N,N-dimethylacetamide, 1,3-dimethyl-2-imidazolinone and dimethyl sulfoxide may be used. These inert solvents may be used alone or in combination.

In the reaction, the base may be inorganic or organic, and as inorganic bases, carbonates or hydroxides of alkali metal atoms or alkaline earth metal atoms, such as sodium carbonate, potassium carbonate, calcium carbonate, sodium hydrogencarbonate, sodium hydroxide, potassium hydroxide and calcium hydroxide or hydrides of alkali metal atoms such as lithium hydride and sodium hydride may be used, and as organic bases, for example, triethylamine, diisopropylethylamine and pyridine may be used. These bases may be used alone or in combination. The amount of a base is appropriately selected within the range of from 0.5 to 3.0 eq, preferably from 0.8 to 2.0 eq, based on the compound (II).

The reaction temperature is selected within the range of from −70° C. to the boiling point of the inert solvent to be used, preferably from −40° C. to 40° C. The reaction time is usually selected within the range of from several minutes to 48 hours, though it depends on the reaction temperature, the amounts of the reactants and the like. After the reaction, the desired product is isolated from the reaction system by a conventional method and, if necessary, purified by column chromatography or recrystallization.

Process 2

(wherein A, Q, R¹, R², X and n are the same as defined above.)

A compound (I-1) of the present invention is obtainable by reaction of a compound (II) with a compound (IV) in an inert solvent.

With respect to the amounts of the starting compounds used in the reaction, the compound (IV) relative to the compound (II) is appropriately selected within the range of from 0.5 to 3.0 eq, preferably from 0.8 to 2.0 eq.

In the reaction, as the inert solvent, the solvents exemplified for Process 1 may be used.

The reaction temperature is selected within the range of from −70° C. to the boiling point of the inert solvent to be used, preferably from −10° C. to the boiling point of the inert solvent. The reaction time is usually selected within the range of from several minutes to 48 hours, though it depends on the reaction temperature, the amounts of the reactants and the like. After the reaction, the desired product is isolated from the reaction system by a conventional method and, if necessary, purified by column chromatography or recrystallization.

Process 3

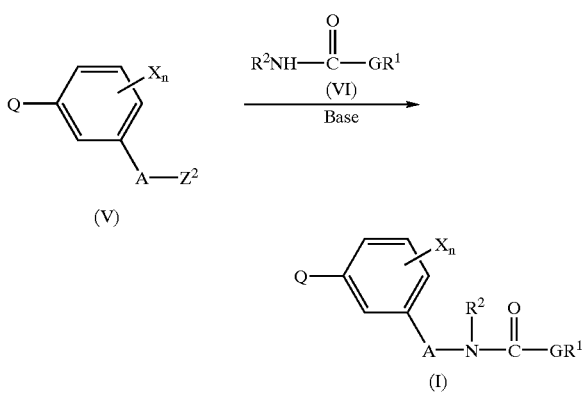

(wherein A, G, Q, $R^1$, $R^2$, X and n are the same as defined above, and Z2 is a chlorine atom, a bromine atom, an iodine atom, a tosyloxy group or a mesyloxy group.)

A compound (I) of the present invention is obtainable by reaction of a compound (V) with a compound (VI) in an inert solvent in the presence of a base.

With respect to the amounts of the starting compounds used in the reaction, the compound (VI) relative to the compound (V) is appropriately selected within the range of from 0.5 eq to an excess, preferably from 0.8 to 2.0 eq.

In the reaction, as the inert solvent, solvents exemplified for Process 1 may be used.

In the reaction, as the base, the bases exemplified for Process 1 may be used. The amount of a base is appropriately selected within the range of from 1 eq to an excess, preferably from 1 eq to 2 eq, based on the compound (V).

The reaction temperature is selected within the range of from −70° C. to the boiling point of the reaction mixture to be used, preferably from −10° C. to the boiling point of the reaction mixture. The reaction time is usually selected within the range of from several minutes to 48 hours, though it depends on the reaction temperature, the amounts of the reactants and the like. After the reaction, the desired product is isolated from the reaction system by a conventional method and, if necessary, purified by column chromatography or recrystallization.

Process 4

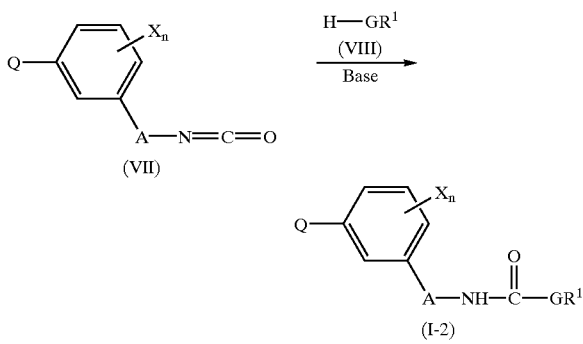

(wherein A, G, Q, $R^1$, X and n are the same as defined above.)

A compound (I-2) of the present invention is obtainable by reaction of a compound (VII) with a compound (VIII) in an inert solvent.

With respect to the amounts of the starting compounds used in the reaction, the compound (VIII) relative to the compound (VII) is appropriately selected within the range of from 1 eq to an excess, preferably from 1.0 to 2.0 eq.

In the reaction, as the inert solvent, the solvents exemplified for Process 1 may be used.

The reaction temperature is selected within the range of from −70° C. to the boiling point of the reaction mixture to be used, preferably from −10° C. to the boiling point of the reaction mixture. The reaction time is usually selected within the range of from several minutes to 48 hours, though it depends on the reaction temperature, the amounts of the reactants and the like. After the reaction, the desired product is isolated from the reaction system by a conventional method and, if necessary, purified by column chromatography or recrystallization.

Process 5

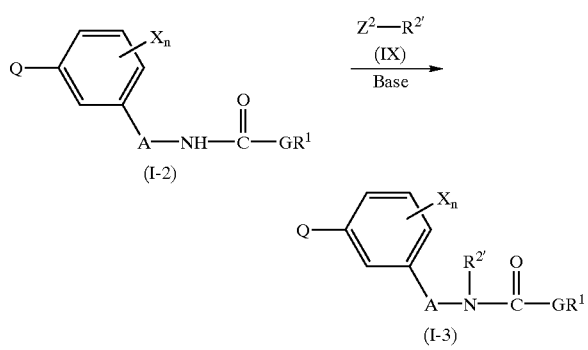

(wherein A, G, Q, $R^1$, X and n are the same as defined above, $R^{2'}$ is $R^2$ (which is the same as defined above) exclusive of a hydrogen atom, and $Z^2$ is a chlorine atom, a bromine atom, an iodine atom, a tosyloxy group or a mesyloxy group.)

A compound (I-3) of the present invention is obtainable by reaction of a compound (I-2) of the present invention with a compound (IX) in an inert solvent in the presence of a base.

With respect to the amounts of the starting compounds used in the reaction, the compound (IX) relative to the compound (I-2) is appropriately selected within the range of from 1 eq to an excess, preferably from 1.0 to 3.0 eq.

In the reaction, as the inert solvent, the solvents exemplified for Process 1 may be used.

In the reaction, as the base, the bases exemplified for Process 1 may be used. The amount of a base is appropriately selected within the range of from 1 eq to an excess, preferably from 1 eq to 2 eq, based on the compound (I-2).

The reaction temperature is selected within the range of from −70° C. to the boiling point of the inert solvent to be used. The reaction time is usually selected within the range of from several minutes to 48 hours, though it depends on the reaction temperature, the amounts of the reactants and the like. After the reaction, the desired product is isolated from the reaction system by a conventional method and, if necessary, purified by column chromatography or recrystallization.

Process 6

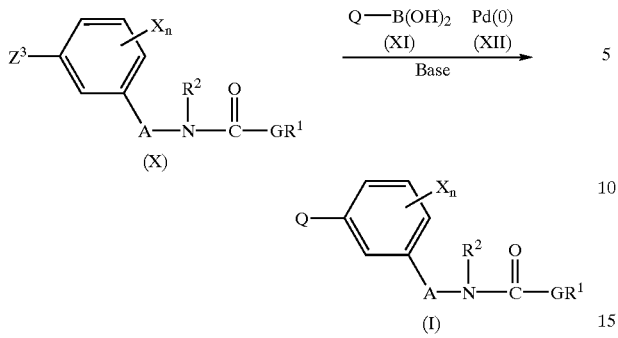

(wherein A, G, Q, $R^1$, $R^2$, X and n are the same as defined above, and $Z^3$ is a bromine atom, an iodine atom or a trifluoromethanesulfonyloxy group.)

A compound (I) of the present invention is obtainable by reaction of a compound (X) with a compound (XI) in an inert solvent in the presence of a zero-valent palladium catalyst (XII) and a base by a conventional method (for example, Synthetic Communications, vol. 11, p.513 (1981)).

With respect to the amounts of the starting compounds used in the reaction, the compound (XI) relative to the compound (X) is appropriately selected within the range of from 1 eq to an excess, preferably from 1.0 eq to 2.0 eq.

As the inert solvent to be used in the reaction, any solvent that does not inhibit the progress of the reaction, and for example, ethers such as diethyl ether, diisopropyl ether, tetrahydrofuran, dioxane, monoglyme and diglyme, aromatic hydrocarbons such as benzene, chlorobenzene, nitrobenzene and toluene, nitrites such as acetonitrile, alcohols such as methanol, ethanol, propanol and 2-propanol, esters such as methyl acetate and ethyl acetate, N,N-dimethylformamide, N,N-dimethylacetamide and water may be used. These solvents may be used alone or in combination.

As the zero-valent palladium catalyst to be used in the reaction, a palladium complex such as tetrakis(triphenylphosphine)palladium (0), bis(dibenzylideneacetone)palladium (0) or tris(dibenzylideneacetone)dipalladium (0) may be used. The amount of a zero-valent palladium catalyst is appropriately selected within the range of from 0.001 eq to 1 eq, preferably from 0.01 eq to 0.2 eq, based on the compound (X).

As the base to be used in the reaction, carbonates or hydroxides of alkali metal atoms or alkaline earth metal atoms, such as sodium carbonate, potassium carbonate, calcium carbonate, sodium hydrogencarbonate, sodium hydroxide, potassium hydroxide, calcium hydroxide and barium hydroxide may be used. These bases may be used alone or in combination. The amount of a base is appropriately selected within the range of from 1.0 eq to an excess, preferably from 1 eq to 2 eq, based on the compound (X).

The reaction temperature is selected within the range of from −70° C. to the boiling point of the inert solvent to be used, preferably from room temperature to the boiling temperature of the reaction mixture. The reaction time is usually selected within the range of from several minutes to 48 hours, though it depends on the reaction temperature, the amounts of the reactants and the like. After the reaction, the desired product is isolated from the reaction system by a conventional method and, if necessary, purified by column chromatography or recrystallization.

The boric acid derivative as the compound (XI) is obtainable by a known method (for example, Jikken Kagaku Koza, 4th edition, vol. 24, p.80, Maruzen).

Process 7

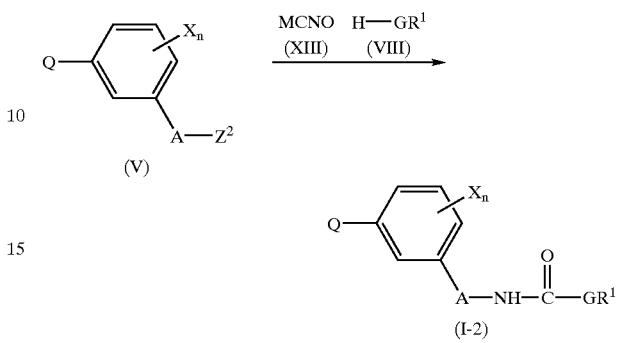

(wherein A, G, Q, $R^1$, X, n and $Z^2$ are the same as defined above, and M is a sodium atom or a potassium atom.)

A compound (I-2) of the present invention is obtainable by reaction of a compound (V) with a compound (XIII) and a compound (VIII) in an inert solvent.

With respect to the amounts of the starting compounds used in the reaction, the compound (XIII) relative to the compound (V) is appropriately selected within the range of from 1.0 to 5.0 eq, preferably from 1.0 to 3.0 eq, and the compound (VIII) relative to the compound (V) is appropriately selected within the range of from 1.0 eq to an excess.

In the reaction, as the inert solvent, the solvents exemplified for Process 1 may be used.

The reaction temperature is selected within the range of from room temperature to the boiling point of the reaction mixture to be used, preferably from 30° C. to the boiling point of the reaction mixture. The reaction time is usually selected within the range of from 1 hour to 24 hours, though it depends on the reaction temperature, the amounts of the reactants and the like. After the reaction, the desired product is isolated from the reaction system by a conventional method and, if necessary, purified by column chromatography or recrystallization.

Preparation of Compounds (II)

Compounds (II) can be synthesized in accordance with Processes a to d as follows. However, its synthesis is not restricted to these processes.

(Process a)

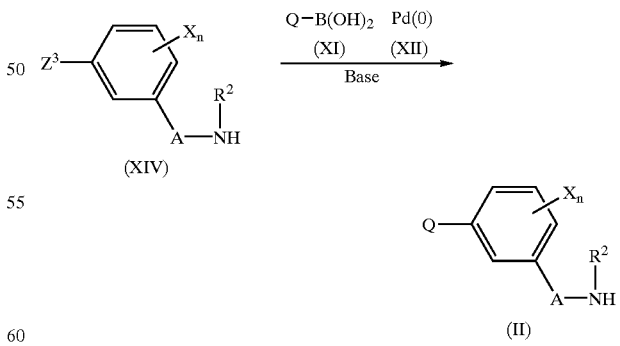

(wherein A, Q, $R^1$, X, n and $Z^3$ are the same as defined above.)

A compound (II) is obtainable by reaction of a compound (XIV) with a compound (XI) in an inert solvent in the presence of a compound (XII) and a base in accordance with Process 6 as mentioned above.

(Process b)

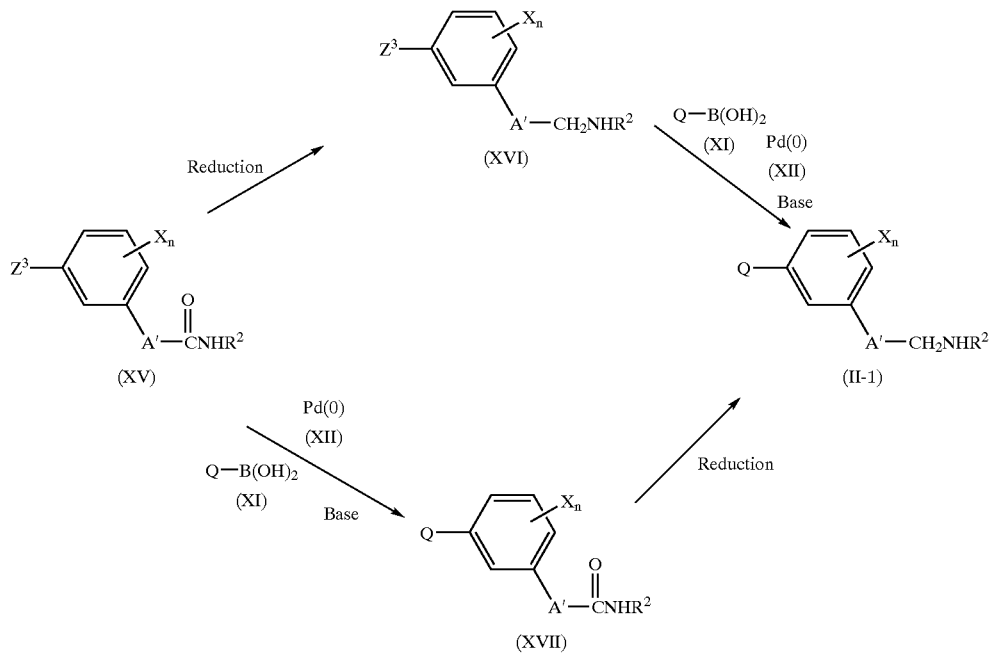

(wherein Q, R¹, X, n and Z³ are the same as defined above, and A' is a ($C_1$–$C_6$) alkylene group which may be branched or a bond.)

A compound (II-1) is obtainable by reduction of a compound (XV) and subsequent reaction of the resulting compound (XVI) with a compound (XI) in the presence of a compound (XII) and a base in an inert solvent in accordance with Process 6 as mentioned above.

A compound (II-1) is also obtainable by reaction of a compound (XV) with a compound (XI) in the presence of a compound (XII) and a base in an inert solvent in accordance with Process 6 as mentioned above and subsequent reduction of the resulting compound (XVII).

(Process c)

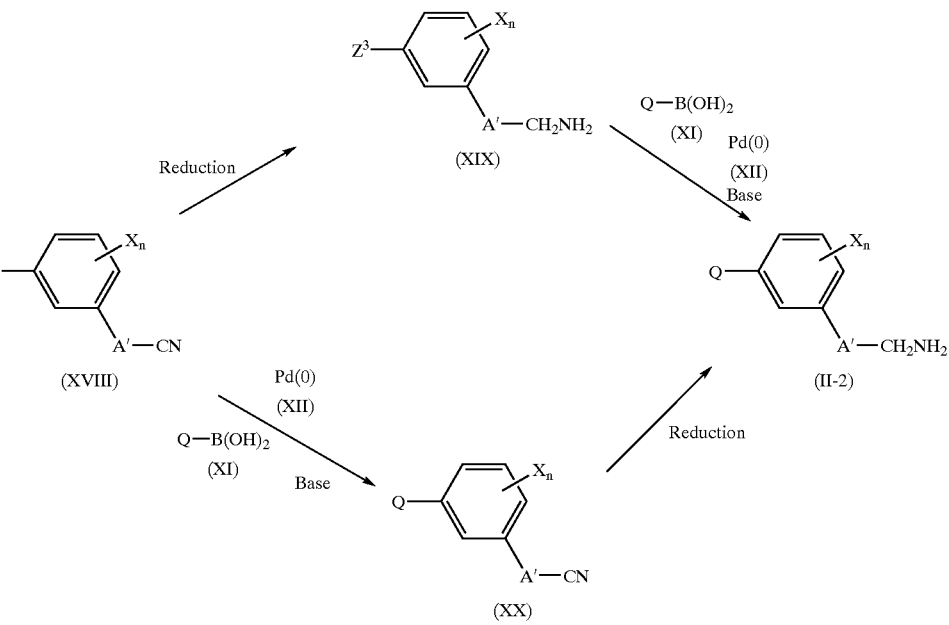

(wherein A', Q, X, n and Z³ are the same as defined above.)

A compound (II-2) is obtainable by reduction of a compound (XVIII) followed by reaction of the resulting compound (XIX) with a compound (XI) in the presence of a compound (XII) and a base in an inert solvent in accordance with Process 6 as mentioned above.

A compound (II-2) is also obtainable by reaction of a compound (XVIII) with a compound (XI) in the presence of a compound (XII) and a base in an inert solvent in accordance with Process 6 as mentioned above, followed by reduction of the resulting compound (XX).

(Process d)

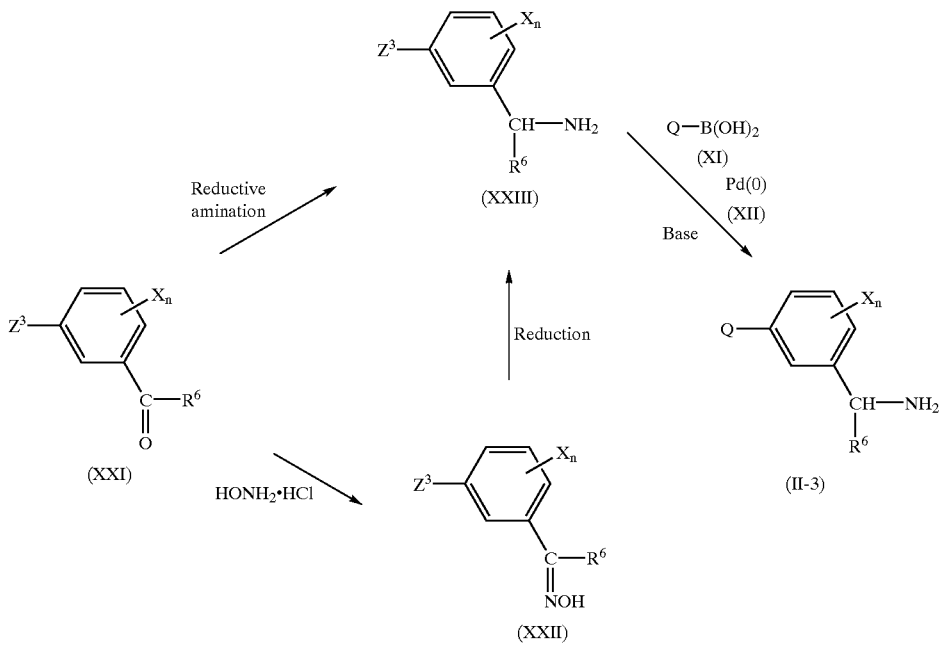

(wherein Q, X, n and $Z^3$ are the same as defined above, and $R^6$ is an alkyl group.)

A compound (II-3) is obtainable by conversion of a compound (XXI) into a compound (XXIII) by reductive amination or by reaction with a hydroxylamine hydrochloride in an inert solvent followed by reduction of the resulting compound (XXII), and subsequent reaction of the resulting compound (XXIII) with a compound (XI) in the presence of a compound (XII) and a base in an inert solvent in accordance with Process 6 as mentioned above.

Preparation of compounds (V)

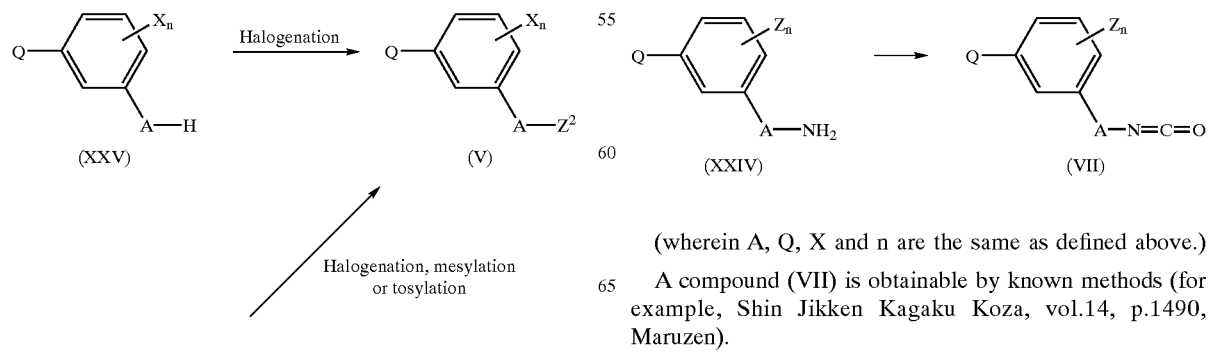

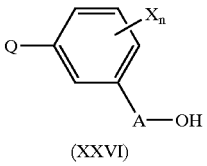

(wherein A, Q, X, n and $Z^2$ are the same as defined above.)

A compound (V) is obtainable by halogenation of a compound (XXV), or halogenation, mesylation or tosylation of a compound (XXVI).

Preparation of compounds (VII)

(wherein A, Q, X and n are the same as defined above.)

A compound (VII) is obtainable by known methods (for example, Shin Jikken Kagaku Koza, vol.14, p.1490, Maruzen).

Preparation of Compounds (X)

A compound (X) is obtainable in accordance with Processes 1–5 or Process 7 as a compound of general formula (I) wherein Q is $Z^3$.

BEST MODE FOR CARRYING OUT THE INVENTION

Now, preparation, formulation and use of the compounds of the present invention will be illustrated by the following specific Examples.

PREPARATION EXAMPLE 1

Preparation of Methyl N-(3-phenylbenzyl) carbamate (Compound No. 1-1)

11.18 g of 3-phenylbenzylamine in toluene (250 ml) was mixed with 7.24 g of pyridine at room temperature. The resulting solution was stirred under cooling with ice while 9.58 g of methyl chloroformate was added dropwise and then stirred at room temperature for 2 hours. After the reaction, the reaction solution was poured into aqueous citric acid and extracted with ethyl acetate, and the organic layer was washed with aqueous citric acid, dried over anhydrous magnesium sulfate and evaporated under reduced pressure for removal of the solvent. The residue was purified by silica gel column chromatography to give 8.61 g of methyl N-(3-phenylbenzyl)carbamate as pale yellow crystals. m.p. 49-52° C.

$^1$H-NMR: (CDCl$_3$/TMS, δ (ppm)) 3.70 (s, 3H), 4.43 (d, 2H), 5.06 (br, 1H), 7.16–7.59 (m, 9H).

PREPARATION EXAMPLE 2

Preparation of Methyl N-[3-(3,4-dichlorophenyl) benzyl]carbamate (Compound No. 1-118)

1.30 g of methyl N-(3-bromobenzyl)carbamate, 0.56 g of sodium carbonate in aqueous solution (20 ml) and 0.13 g of tetrakis(triphenylphosphine)palladium (0) were added to toluene (40 ml) under a nitrogen atmosphere. The resulting solution was mixed with 1.02 g of 3,4-dichlorophenylboric acid in ethanol (20 ml) at room temperature with stirring and refluxed under heating for 2 hours. After the reaction, the reaction solution was cooled to room temperature, poured into saturated aqueous sodium chloride and extracted with ethyl acetate, and the organic layer was dried over anhydrous magnesium sulfate and evaporated under reduced pressure for removal of the solvent. The residue was purified by silica gel column chromatography to give 1.45 g of methyl N-[3-(3,4-dichlorophenyl)benzyl]carbamate as a yellow transparent viscous liquid.

$^1$H-NMR: (CDCl$_3$/TMS, δ (ppm)) 3.69 (s, 3H). 4.40 (d, 2H), 5.23 (br, 1H), 7.25–7.63 (m, 7H).

PREPARATION EXAMPLE 3

Preparation of Isopropyl N-(3-phenylbenzyl) carbamate (Compound No. 1-150)

1.20 g of isopropyl N-(3-bromobenzyl)carbamate, 0.47 g of sodium carbonate in aqueous solution (20 ml) and 0.10 g of tetrakis(triphenylphosphine)palladium (0) were added to toluene (40 ml) under a nitrogen atmosphere. The resulting solution was mixed with 0.54 g of phenylboric acid in ethanol (20 ml) at room temperature with stirring and refluxed under heating for 2 hours. After the reaction, the reaction solution was cooled to room temperature, poured into saturated aqueous sodium chloride and extracted with ethyl acetate, and the organic layer was dried over anhydrous magnesium sulfate and evaporated under reduced pressure for removal of the solvent. The residue was purified by silica gel column chromatography to give 0.85 g of isopropyl N-(3-phenylbenzyl)carbamate as white crystals. m.p. 61–64° C.

$^1$H-NMR: (CDCl$_3$/TMS, δ (ppm)) 1.24 (d, 6H), 4.43 (d, 2H), 4.95 (br, 1H), 4.96 (m, 1H), 7.26–7.59 (m, 9H).

PREPARATION EXAMPLE 4

Preparation of Methyl N-(3-phenylbenzyl)-N-(2-propynyl)carbamate (Compound No. 1-178)

0.70 g of methyl N-(3-phenylbenzyl)carbamate in tetrahydrofuran (20 ml) was stirred together with 0.15 g of 60% sodium hydride at room temperature for 30 minutes. 0.52 g of propargyl bromide was added dropwise at room temperature, and the resulting solution was stirred overnight. After the reaction, the reaction solution was poured into water and extracted with ethyl acetate, and the organic layer was separated, dried over anhydrous magnesium sulfate and evaporated under reduced pressure for removal of the solvent. The residue was purified by silica gel column chromatography to give 0.54 g of methyl N-(3-phenylbenzyl)N-(2-propynyl)carbamate as a yellow transparent viscous liquid.

$^1$H-NMR: (CDCl$_3$/TMS, δ (ppm)) 2.24 (t, 1H), 3.79 (s, 3H), 3.99–4.10 (m, 2H), 4.67 (s, 2H), 7.25–7.59 (m, 9H).

PREPARATION EXAMPLE 5

Preparation of Methyl N-methoxymethyl-N-(3-phenylbenzyl)carbamate (Compound No. 1-192)

1.00 g of methyl N-(3-phenylbenzyl)carbamate in tetrahydrofuran (20 ml) was stirred together with 0.22 g of 60% sodium hydride at room temperature for 30 minutes. 0.78 g of methoxymethyl bromide was added dropwise at room temperature, and the resulting solution was stirred overnight. After the reaction, the reaction solution was poured into water and extracted with ethyl acetate, and the organic layer was separated, dried over anhydrous magnesium sulfate and evaporated under reduced pressure for removal of the solvent. The residue was purified by silica gel column chromatography to give 0.90 g of methyl N-methoxymethyl-N-(3-phenylbenzyl)carbamate as a pale yellow transparent viscous liquid.

$^1$H-NMR: (CDCl$_3$/TMS, δ (ppm)) 3.29–3.34 (m, 3H), 3.77 (s, 3H), 4.48–4.62 (dd, 2H), 4.66–4.78 (dd, 2H), 7.06–7.58 (m, 9H).

PREPARATION EXAMPLE 6

Preparation of Methyl N-(2-methyl-3-phenylbenzyl) carbamate (Compound No. 2-1)

3.57 g of 2-methyl-3-phenylbenzyl bromide, 1.66 g of potassium cyanate and 7.00 g of methanol in N,N-dimethylformamide (30 ml) were stirred at 80° C. for 5 hours. After the reaction, the reaction solution was poured into water and extracted with ethyl acetate, and the organic layer was separated, dried over anhydrous magnesium sulfate and evaporated under reduced pressure for removal of the solvent. The residue was purified by silica gel column chromatography to give 2.01 g of methyl N-(2-methyl-3-phenylbenzyl)carbamate as colorless crystals. m.p. 91–94° C.

$^1$H-NMR: (CDCl$_3$/TMS, δ (ppm)) 2.20 (s, 3H), 3.71 (s, 3H), 4.43 (d, 2H), 5.24 (br, 1H), 7.2–7.4 (m, 8H).

PREPARATION EXAMPLE 7

Preparation of Methyl N-{1-[3-(4-methoxyphenyl)phenyl]ethyl}carbamate (Compound No. 3-15)

1.00 g of methyl N-[1-(3-bromophenyl)ethyl]carbamate, 0.41 g of sodium carbonate in aqueous solution (20 ml) and 0.09 g of tetrakis(triphenylphosphine)palladium (0) were added to toluene (40 ml) under a nitrogen atmosphere. The resulting solution was mixed with 0.59 g of 4-methoxyphenylboric acid in ethanol (20 ml) at room temperature with stirring and refluxed under heating for 2 hours. After the reaction, the reaction solution was cooled to room temperature, poured into saturated aqueous sodium chloride and extracted with ethyl acetate, and the organic layer was dried over anhydrous magnesium sulfate and evaporated under reduced pressure for removal of the solvent. The residue was purified by silica gel column chromatography to give 1.45 g of methyl N-{1-[3-(4-methoxyphenyl)phenyl]ethyl}carbamate as pale yellow crystals. m.p. 117–119° C.

$^1$H-NMR: (CDCl$_3$/TMS, δ (ppm)) 1.51 (d, 3H), 3.66 (s, 3H), 3.84 (s, 3H), 4.89 (br, 1H), 4.99 (br, 1H), 6.94–7.52 (m, 8H).

PREPARATION EXAMPLE 8

Preparation of Methyl N-methoxy-N-(2-methyl-3-phenylbenzyl)carbamate (Compound No. 4-22)

0.40 g of methyl N-methoxycarbamate in N,N-dimethylformamide (20 ml) was stirred together with 0.18 g of 60% sodium hydride at room temperature for 30 minutes. 1.00 g of 2-methyl-3-phenylbenzyl bromide was added dropwise at room temperature, and the resulting solution was stirred for 3 hours. After the reaction, the reaction solution was poured into water and extracted with ethyl acetate, and the organic layer was separated, dried over anhydrous magnesium sulfate and evaporated under reduced pressure for removal of the solvent. The residue was purified by silica gel column chromatography to give 0.55 g of methyl N-methoxy-N-(2-methyl-3-phenylbenzyl)carbamate as a transparent viscous liquid.

$^1$H-NMR: (CDCl$_3$/TMS, δ (ppm)) 2.23 (s, 3H), 3.55 (s, 3H), 3.83 (s, 3H), 4.75 (s, 2H), 7.2–7.5 (m, 8H).

Now, the $^1$H-NMR data (CDCl$_3$/TMS, δ (ppm)) of some examples of the compounds of the present invention are shown below.

TABLE 54

| Comp. No. | $^1$H-NMR δ (ppm) Solvent CDCl$_3$ |
|---|---|
| 1-2 | 3.70 (s, 3H); 4.55 (d, 2H); 5.10 (br, 1H); 7.3–7.5 (m, 8H) |
| 1-3 | 3.71 (s, 3H); 4.43 (d, 2H); 5.07 (br, 1H); 7.2–7.6 (m, 8H) |
| 1-6 | 3.71 (s, 3H); 4.43 (d, 2H); 5.11 (br, 1H); 7.0–7.1 (m, 1H); 7.3–7.5 (m, 7H) |
| 1-10 | 2.25 (s, 3H); 3.69 (s, 3H); 4.42 (d, 2H); 5.06 (br, 1H); 7.2–7.4 (m, 8H) |
| 1-11 | 2.42 (s, 3H); 3.71 (s, 3H); 4.43 (d, 2H); 5.05 (br, 1H); 7.1–7.5 (m, 8H) |
| 1-13 | 1.29 (t, 3H); 2.72 (q, 2H); 3.71 (s, 3H); 4.44 (d, 2H); 5.04 (s, 1H); 7.2–7.5 (m, 8H) |
| 1-17 | 1.30 (d, 6H); 2.97 (sept, 1H); 3.70 (s, 3H); 4.43 (d, 2H); 5.08 (br, 1H); 7.22–7.51 (m, 8H) |
| 1-34 | 3.71 (s, 3H); 4.44 (d, 2H); 5.13 (br, 1H); 7.3–7.8 (m, 8H) |
| 1-40 | 3.66 (s, 3H); 3.77 (s 3H); 4.38 (d, 2H); 5.14 (br, 1H); 6.95–7.03 (m, 2H); 7.2–7.4 (m, 6H) |
| 1-41 | 3.70 (s, 3H); 3.85 (s, 3H); 4.42 (d, 2H); 5.10 (br, 1H); 6.87–6.91 (m, 1H); 7.1–7.5 (m, 7H) |

TABLE 54-continued

| Comp. No. | $^1$H-NMR δ (ppm) Solvent CDCl$_3$ |
|---|---|
| 1-71 | 3.71 (s, 3H); 4.44 (d, 2H); 5.10 (br, 1H); 7.19–7.53 (m, 8H) |
| 1-119 | 3.72 (s, 3H); 4.44 (d, 2H); 5.08 (br, 1H); 7.3–7.4 (m, 7H) |
| 1-125 | 2.30 (s, 3H); 2.32 (s, 3H); 3.69 (s, 3H); 4.41 (d, 2H); 5.08 (br, 1H); 7.2–7.5 (m, 7H) |
| 1-146 | 1.25 (t, 3H); 4.16 (q, 2H); 4.43 (d, 2H); 5.04 (br, 1H); 7.2–7.6 (m, 9H) |

TABLE 55

| Comp. No. | $^1$H-NMR δ (ppm) Solvent CDCl$_3$ |
|---|---|
| 1-147 | 0.93 (t, 3H); 1.6–1.7 (m, 2H); 4.06 (t, 2H); 4.43 (d, 2H); 5.05 (br, 1H); 7.2–7.6 (m, 9H) |
| 1-148 | 0.92 (t, 3H); 1.34–1.41 (m, 2H); 1.55–1.67 (m, 2H); 4.10 (t, 2H); 4.43 (d, 2H); 5.04 (br, 1H); 7.2–7.6 (m, 9H) |
| 1-163 | 2.89 (d, 3H); 3.75 (s, 3H); 4.53 (d, 2H); 7.2–7.7 (m, 9H) |
| 1-165 | 1.10 (br, 3H); 3.30 (br, 2H); 3.75 (s, 3H); 4.54 (s, 2H); 7.3–7.6 (m, 9H) |
| 1-166 | 0.86 (br, 3H); 1.55 (br, 2H); 3.21 (m, 2H); 3.74 (s, 3H); 4.56 (s, 2H); 7.2–7.6 (m, 9H) |
| 1-168 | 3.76 (s, 3H); 3.86 (d, 2H); 4.54 (m, 2H); 5.15 (m, 2H); 5.76 (br, 1H); 7.2–7.6 (m, 9H) |
| 1-188 | 3.81 (s, 3H); 4.41 (d, 2H); 4.51 (s, 2H); 7.2–7.6 (m, 14H) |
| 1-193 | 2.25 (s, 3H); 3.30 (d, 3H); 3.76 (s, 3H); 4.59 (d, 2H); 4.73 (d, 2H); 7.2–7.4 (m, 8H) |
| 1-194 | 2.42 (s, 3H); 3.32 (d, 3H); 3.78 (s, 3H); 4.61 (d, 2H); 4.73 (d, 2H); 7.1–7.5 (m, 8H) |
| 1-195 | 2.60 (s, 3H); 3.33 (d, 3H); 3.78 (s, 3H); 4.60 (d, 2H); 4.73 (d, 2H); 7.2–7.5 (m, 8H) |
| 1-198 | 3.32 (d, 3H); 3.78 (s, 3H); 3.85 (s, 3H); 4.60 (d 2H); 4.73 (d, 2H); 6.79 (d, 2H); 7.3–7.5 (m, 6H) |
| 1-201 | 3.32 (d, 3H); 3.78 (s, 3H); 4.60 (d, 2H); 4.74 (d, 2H); 7.1–7.5 (m, 8H) |

TABLE 56

| Comp. No. | $^1$H-NMR δ (ppm) Solvent CDCl$_3$ |
|---|---|
| 1-202 | 3.30 (d, 3H); 3.77 (s, 3H); 4.49–4.62 (dd, 2H); 4.69–4.78 (dd, 2H); 7.2–7.5 (m, 8H) |
| 1-231 | 2.57 (s, 3H); 3.79 (s, 3H); 4.99 (s, 2H); 7.15–7.58 (m, 9H) |
| 1-262 | 2.87 (s, 6H); 4.49 (d, 2H); 4.76 (br, 1H); 7.3–7.7 (m, 9H) |
| 1-264 | 3.70 (s, 3H); 3.62 (s, 3H); 4.72 (s, 2H); 7.3–7.6 (m, 9H) |
| 1-266 | 2.42 (s, 3H); 3.62 (s, 3H); 3.82 (s, 3H); 4.71 (s, 2H); 7.2–7.5 (m, 8H) |
| 1-275 | 3.63 (s, 3H); 3.82 (s, 3H); 4.72 (s, 2H); 7.2–7.6 (m, 8H) |
| 1-277 | 3.64 (s, 3H); 3.83 (s, 3H); 4.73 (s, 2H); 7.3–7.8 (m, 8H) |
| 2-22 | 2.40 (s, 3H); 3.67 (s, 3H); 4.35 (d, 2H); 5.20 (br, 1H); 7.0–7.3 (m, 7H) |
| 2-98 | 2.42 (s, 3H); 3.72 (s, 3H); 4.41 (d, 2H); 5.07 (br, 1H); 7.14–7.80 (m, 7H) |
| 2-106 | 3.69 (s, 3H); 4.46 (d, 2H); 5.20 (br, 1H); 7.11 (t, 1H); 7.26–7.53 (m, 6H) |
| 2-109 | 2.41 (s, 3H); 3.68 (s, 3H); 4.45 (d, 2H); 5.16 (br, 1H); 7.0–7.5 (m, 7H) |
| 2-111 | 1.28 (t, 3H); 2.72 (q, 2H); 3.68 (s, 3H); 4.46 (d, 2H); 5.14 (br, 1H); 7.07–7.53 (m, 7H) |
| 2-113 | 1.30 (d, 6H); 2.97 (sept, 1H); 3.69 (s, 3H); 4.47 (d, 2H); 5.12 (br, 1H); 7.10 (dd, 1H); 7.23–7.55 (m, 6H) |
| 2-116 | 1.36 (s, 9H); 3.69 (s, 3H); 4.46 (d, 2H); 5.13 (br, 1H); 7.07 (dd, 1H); 7.0–7.5 (m, 6H) |

TABLE 57

| Comp. No. | $^1$H-NMR δ (ppm) Solvent CDCl$_3$ |
|---|---|
| 2-123 | 3.68 (s, 3H); 3.86 (s, 3H); 4.46 (d, 2H); 5.14 (br, 1H); 6.89 (dd, 1H); 7.04–7.53 (m, 6H) |
| 2-125 | 3.70 (s, 3H); 4.47 (d, 2H); 5.15 (br, 1H); 7.10–7.55 (m, 7H) |
| 2-126 | 3.69 (s, 3H); 4.46 (d, 2H); 5.21 (br, 1H); 6.9–7.5 (m, 7H) |
| 2-166 | 2.29 (s, 3H); 2.32 (s, 3H); 3.68 (s, 3H); 4.45 (d, 2H); 5.17 (br, 1H); 7.00 (t, 1H); 7.1–7.6 (m, 5H) |
| 2-185 | 3.68 (s, 3H); 4.48 (dd, 2H); 5.21 (br, 1H); 7.22–7.46 (m, 7H) |
| 2-186 | 3.69 (s, 3H); 4.49 (d, 2H); 5.29 (br, 1H); 7.33–7.58 (m, 7H) |
| 2-188 | 2.24 (s, 3H); 3.66 (s, 3H); 4.49 (d, 2H); 5.25 (br, 1H); 7.16–7.51 (m, 7H) |
| 2-189 | 2.41 (s, 3H); 3.68 (s, 3H); 4.50 (d, 2H); 5.26 (br, 1H); 7.08–7.59 (m, 7H) |
| 2-191 | 1.28 (t, 3H); 2.72 (q, 2H); 3.69 (s, 3H); 4.51 (d, 2H); 5.21 (br, 1H); 7.21–7.60 (m, 7H) |
| 2-193 | 1.29 (d, 6H); 2.97 (sept, 1H); 3.68 (s, 3H); 4.50 (d, 2H); 5.25 (br, 1H); 7.25–7.59 (m, 7H) |
| 2-196 | 1.36 (s, 9H); 3.69 (s, 3H); 4.51 (d, 2H); 5.19 (br, 1H); 7.39–7.60 (m, 7H) |
| 2-284 | 2.36 (s, 3H); 3.69 (s, 3H); 4.42 (d, 2H); 4.94 (br, 1H); 7.22–7.57 (m, 8H) |
| 2-333 | 2.41 (s, 3H); 3.67 (s, 3H); 3.88 (s, 3H); 4.41 (d, 2H); 5.25 (br, 1H); 6.92 (d, 1H); 7.13–7.50 (m, 6H) |

TABLE 58

| Comp. No. | $^1$H-NMR δ (ppm) Solvent CDCl$_3$ |
|---|---|
| 2-346 | 2.29(s, 3H); 3.32(s, 3H); 3.67(s, 3H); 3.88(s, 3H); 4.41(d, 2H); 5.24(br, 1H); 6.92(d, 1H); 7.16–7.48(m, 5H) |
| 2-448 | 3.70(s, 3H); 4.49(d, 2H); 5.40(br, 1H); 6.32(br, 1H); 6.83–7.56(m, 7H) |
| 3-1 | 1.51(d, 3H); 3.65(s, 3H); 4.91 (m, 1H); 5.09(br, 1H); 7.15–7.72(m, 9H) |
| 3-6 | 1.50(d, 3H); 2.41(s, 3H); 3.65(s, 3H); 4.90(br, 1H); 5.12(br, 1H); 7.1–7.5(m, 8H) |
| 3-16 | 1.52(d, 3H); 3.66(s, 3H); 4.91 (br, 1H); 5.14(br, 1H); 7.1–7.8(m, 8H) |
| 3-18 | 1.51(d, 3H); 3.66(s, 3H); 4.90(br, 2H); 7.3–7.5(m, 7H) |
| 3-20 | 1.49(d, 3H); 3.65(s, 3H); 4.89(br, 1H); 5.24(br, 1H); 7.3–7.4(m, 7H) |
| 3-26 | 1.53(d, 3H); 3.66(s, 3H); 5.07(q, 1H); 5.19(br, 1H); 7.10(dd, 8H); 7.31–7.54 (m, 7H) |
| 4-199 | 3.65(s, 3H); 3.83(s, 3H); 4.86(s, 2H); 7.38–7.53(m, 7H) |
| 4-201 | 2.39(s, 3H); 3.63(s, 3H); 3.82(s, 3H); 4.85(s, 2H); 7.22–7.57(m, 7H) |

Now, preparation of intermediates of the compounds of the present invention will be illustrated by Reference Examples.

REFERENCE EXAMPLE 1

Preparation of Methyl N-(3-bromobenzyl)carbamate 10.00 g of 3-bromobenzylamine hydrochloride suspended in chloroform (100 ml) was mixed with 9.55 g of triethylamine at room temperature. The resulting solution was stirred under cooling with ice while 4.67 g of methyl chloroformate was added dropwise and then stirred at room temperature for 2 hours. After the reaction, the reaction solution was poured into saturated aqueous sodium chloride, and the organic layer was separated, dried over anhydrous magnesium sulfate and evaporated at ordinary pressure for removal of the solvent. The residue was purified by silica gel column chromatography to give 9.54 g of methyl N-(3-bromobenzyl)carbamate as white crystals. m.p. 41–44° C.

$^1$H-NMR: (CDCl$_3$/TMS, δ (ppm)) 3.69 (s, 3H), 4.33 (d, 2H), 5.17 (br, 1H), 7.16–7.42 (m, 4H).

REFERENCE EXAMPLE 2

Preparation of Isopropyl N-(3-bromobenzyl)carbamate 3.00 g of 3-bromobenzylamine hydrochloride suspended in chloroform (20 ml) was mixed with 2.86 g of triethylamine at room temperature. The resulting solution was stirred under cooling with ice while 1.82 g of isopropyl chloroformate was added dropwise and then stirred at room temperature for 2 hours. After the reaction, the reaction solution was poured into saturated aqueous sodium chloride, and the organic layer was separated, dried over anhydrous magnesium sulfate and evaporated at ordinary pressure for removal of the solvent. The residue was purified by silica gel column chromatography to give 3.33 g of isopropyl N-(3-bromobenzyl)carbamate as a colorless transparent viscous liquid.

$^1$H-NMR: (CDCl$_3$/TMS, δ (ppm)) 1.24 (d, 6H), 4.32 (d, 2H), 4.96 (m, 1H), 5.02 (br, 1H), 7.16–7.43 (m, 4H).

REFERENCE EXAMPLE 3

Preparation of 3-phenylbenzylamine 18.25 g of 3-bromobenzylamine hydrochloride, 17.39 g of sodium carbonate in aqueous solution (120 ml) and 1.90 g of tetrakis(triphenylphosphine)palladium (0) were added to toluene (240 ml) under a nitrogen atmosphere. The resulting solution was mixed with 10.00 g of phenylboric acid in ethanol (120 ml) at room temperature with stirring and refluxed under heating for 2 hours. After the reaction, the reaction solution was cooled to room temperature, poured into saturated aqueous sodium chloride and extracted with ethyl acetate, and the organic layer was dried over anhydrous magnesium sulfate and evaporated under reduced pressure for removal of the solvent to give 11.18 g of crude 3-phenylbenzylamine as a brown viscous liquid.

REFERENCE EXAMPLE 4

Preparation of Methyl N-[1-(3-bromophenyl)ethyl]carbamate 23.77 g of 3-bromo-a-methylbenzylamine in toluene (120 ml) was mixed with 14.08 g of pyridine at room temperature. The resulting solution was stirred under cooling with ice while 18.64 g of methyl chloroformate was added dropwise and then stirred at room temperature for 2 hours. After the reaction, the reaction solution was poured into aqueous citric acid and extracted with ethyl acetate, and the organic layer was washed with aqueous citric acid, dried over anhydrous magnesium sulfate and evaporated under reduced pressure for removal of the solvent. The residue was purified by silica gel column chromatography to give 10.50 g of methyl N-[1-(3-bromophenyl)ethyl]carbamate as a colorless transparent viscous liquid.

$^1$H-NMR: (CDCl$_3$/TMS, δ (ppm)) 1.46 (d, 3H), 3.65 (s, 3H), 4.78 (br, 1H), 5.14 (br, 1H), 7.16-7.42 (m, 4H).

REFERENCE EXAMPLE 5

Preparation of Methyl N-methoxy-N-(3-bromobenzyl)carbamate 2.52 g of methyl N-methoxycarbamate in N,N-dimethylformamide (30 ml) was stirred together with 1.15 g of 60% sodium hydride at room temperature for 30 minutes. 1.00 g of 3-bromobenzyl bromide was added dropwise at room temperature, and the resulting solution was stirred for 3 hours. After the reaction, the reaction solution was poured into water and extracted with ethyl acetate, and the organic layer was separated, dried over anhydrous magnesium sulfate and evaporated under reduced pressure for removal of the solvent. The residue was purified by silica gel column chromatography to give 4.99 g of methyl N-methoxy-N-(3-bromobenzyl)carbamate as a transparent viscous liquid.

$^1$H-NMR: (CDCl$_3$/TMS, δ (ppm)) 3.62 (s, 3H), 3.81 (s, 3H), 4.61 (s, 2H), 7.0–7.6 (m, 4H).

The agricultural and horticultural fungicides of the present invention contain biarylalkylenecarbamic acid derivatives represented by general formula (I) as active ingredients. When the compounds of the present invention are used for agricultural and horticultural fungicides, the active ingredient can be used in appropriate formulations depending on the purpose. The active ingredient is usually diluted with an inert liquid or solid carrier and is used in an appropriate dosage form such as a dust, a wettable powder, an emulsifiable concentrate or a granule by blending it with a surfactant and other ingredients, depending on its use.

Preferable examples of carriers include solid carriers such as talc, bentonite, clay, kaolin, diatomaceous earth, white carbon, vermiculite, slaked lime, silica sand, ammonium sulfate and urea and liquid carriers such as isopropyl alcohol, xylene, cyclohexanone and methylnaphthalene. Examples of surfactants and dispersants include dinaphthylmethanesulfonates, alcohol-sulfuric acid ester salts, alkylarylsulfonates, lignin sulfonate, polyoxyethylene glycol ether, polyoxyethylene alkyl aryl ethers and polyoxyethylene sorbitan monoalkylate. Examples of adjuvants include carboxymethyl cellulose and the like. These formulations are applied after diluted to appropriate concentrations or directly.

The agricultural and horticultural fungicides of the present invention may be used for foliage treatment, soil treatment or submerged treatment. The blending proportion of the active ingredient is suitably selected depending on the case. However, the preferable proportion is from 0.1 to 20% (by weight) in the cases of a dust or a granule, and from 5 to 80% (by weight) in the cases of an emulsifiable concentrate or a wettable powder.

The dose of the agricultural and horticultural fungicides of the present invention depends on the type of the compound, the disease to be controlled, the tendency of disease development, the degrees of the damage, the environmental conditions and the type of the formulation to be used. For example, for direct use as a dust or a granule, the dose of the active ingredient is selected suitably within the range of from 0.1 g to 5 kg, preferably from 1 g to 1 kg, per are. For use in a liquid state as an emulsifiable concentrate or a wettable powder, the dose is selected suitably within the range of from 0.1 ppm to 10,000 ppm, preferably from 10 to 3,000 ppm.

The compounds of the present invention in the above-mentioned formulations prevent plant diseases caused by Oomycetes, Ascomycetes, Deuteromycetes and Basidiomycetes. Specific but non-restrictive examples of microorganisms are given below. Pseudoperonospora genus such as Pseudoperonospora cubensis, Erysiphe genus such as Erysiphe graminis, Venturia genus such as Venturia inaecualis, Pyricularia genus such as *Pyricularia orvzae*, Botrytis genus such as *Botrytis cinerea* and Rhizoctonia genus such as *Rhizoctonia solani*.

The compounds of the present invention may be used in combination with an insecticide, another fungicide, a herbicide, a plant growth regulator or a fertilizer, as the case requires. Now, typical formulations of the agricultural and horticultural fungicides of the present invention will be described by referring to Formulation Examples. Hereinafter, "%" means "% by weight".

FORMULATION EXAMPLE 1

Dust

2% of Compound (2-102), 5% of diatomaceous earth and 93% of clay were uniformly mixed and pulverized to give a dust.

FORMULATION EXAMPLE 2

Wettable Powder

50% of Compound (1-12), 45% of diatomaceous earth, 2% of sodium dinaphthylmethanedisulfonate and 3% of sodium lignin sulfonate were uniformly mixed and pulverized to give a wettable powder.

FORMULATION EXAMPLE 3

Emulsifiable Concentrate

30% of Compound (1-41), 20% of cyclohexanone, 11% of polyoxyethylene alkyl aryl ether, 4% of calcium alkylbenzenesulfonate and 35% of methylnaphthalene were uniformly dissolved to give an emulsifiable concentrate.

FORMULATION EXAMPLE 4

Granule

5% of Compound (1-1), 2% of the sodium salt of the lauryl alcohol sulfuric ester, 5% of sodium lignin sulfonate, 2% of carboxymethyl cellulose and 86% of clay were uniformly mixed and pulverized. The resulting mixture was kneaded with 20% of water by relative amount, granulated to 14 to 32 mesh by means of an extrusion granulator, dried to give a granule.

Now, the effects of the agricultural and horticultural fungicides will be described by referring to specific Test Examples.

TEST EXAMPLE 1

Test for Preventive Effect on Cucumber Downy Mildew 9 cucumber seeds (variety: Sagami-hanpaku) were sown in each 9 cm×9 cm polyvinyl chloride pot and grown in a greenhouse for 7 days. The cotyledonary cucumber seedlings were treated with 10 ml per pot of aqueous solutions of wettable powders prepared in accordance with Formulation Example 2, at a concentration of 500 ppm in terms of the active ingredients, and dried in the air. Then, the seedlings were inoculated with *Pseudoperonospora cubensis* zoosporangia in suspension by spraying and immediately placed in a moist chamber at 22° C. for 24 hours. Thereafter, the seedlings were placed in a greenhouse. 7 days after the inoculation, the total diseased area in each pot was observed and evaluated on the basis of the standards shown in Table 59. The results are shown in Tables 60 to 61.

TABLE 59

| Evaluation | Preventive value |
| --- | --- |
| A | No diseased area |
| B | Diseased area of less than 25% |
| C | Diseased area of at least 25% but less than 50% |
| D | Diseased area of at least 50% |

TABLE 60

| Comp. No. | Evaluation |
|---|---|
| 1-3 | A |
| 1-7 | B |
| 1-11 | A |
| 1-12 | B |
| 1-33 | B |
| 1-34 | A |
| 1-41 | A |
| 1-103 | B |
| 1-118 | B |
| 1-119 | B |
| 1-125 | A |
| 1-118 | B |
| 1-253 | B |
| 1-266 | B |
| 2-91 | B |
| 2-98 | B |
| 2-102 | A |
| 2-106 | A |
| 2-107 | A |
| 2-109 | A |
| 2-110 | A |
| 2-111 | A |
| 2-113 | B |
| 2-121 | A |
| 2-122 | B |
| 2-123 | A |
| 2-126 | B |
| 2-183 | A |
| 2-184 | B |
| 2-186 | B |
| 2-189 | B |
| 2-191 | A |

TABLE 61

| No. Comp. | Evaluation |
|---|---|
| 2-193 | A |
| 2-201 | A |
| 2-203 | B |
| 2-205 | A |
| 2-215 | A |
| 2-246 | B |
| 2-247 | B |
| 2-257 | B |
| 2-266 | B |
| 2-268 | A |
| 2-288 | A |
| 2-290 | A |
| 2-299 | A |
| 2-300 | B |
| 2-328 | A |
| 2-331 | A |
| 2-333 | A |
| 2-334 | B |
| 2-343 | A |
| 2-346 | B |
| 2-450 | A |
| 3-1 | A |
| 3-6 | A |
| 3-15 | A |
| 3-16 | A |
| 3-21 | A |

TEST EXAMPLE 2

Test for Preventive Effect on Apple Scab 5 apple seeds (variety: Kogyoku) were sown in each 9 cm×9 cm polyvinyl chloride pot and grown in a greenhouse for 20 days. The 4-foliage-leaf apple seedlings were treated with 20 ml per pot of aqueous solutions of wettable powders prepared in accordance with Formulation Example 2, at a concentration of 500 ppm in terms of the active ingredients, and dried in the air. Then, the seedlings were inoculated with *Venturia inaequalis* spores in suspension by spraying and immediately placed in a moist chamber at 22° C. for 48 hours. Thereafter, the seedlings were placed in a greenhouse for development of the disease. 14 days after the inoculation, the diseased areas of the upper two of the inoculated leaves were observed and evaluated on the basis of the standards shown in Table 59. The results are shown in Tables 62 to 66.

TABLE 62

| Comp. No. | Evaluation |
|---|---|
| 1-1 | A |
| 1-2 | A |
| 1-3 | A |
| 1-4 | A |
| 1-6 | A |
| 1-7 | A |
| 1-10 | A |
| 1-11 | A |
| 1-12 | A |
| 1-13 | A |
| 1-14 | A |
| 1-17 | A |
| 1-18 | A |
| 1-33 | A |
| 1-34 | A |
| 1-35 | A |
| 1-40 | A |
| 1-41 | A |
| 1-42 | A |
| 1-72 | A |
| 1-103 | A |
| 1-117 | A |
| 1-118 | A |
| 1-119 | A |
| 1-120 | A |
| 1-122 | A |
| 1-125 | A |
| 1-137 | A |
| 1-146 | B |
| 1-163 | A |
| 1-165 | A |
| 1-166 | B |

TABLE 63

| Comp. No. | Evaluation |
|---|---|
| 1-168 | A |
| 1-178 | A |
| 1-192 | A |
| 1-193 | A |
| 1-194 | A |
| 1-195 | A |
| 1-198 | A |
| 1-201 | A |
| 1-202 | A |
| 1-262 | B |
| 1-264 | A |
| 1-266 | A |
| 1-275 | A |
| 1-277 | A |
| 1-298 | A |
| 2-17 | A |
| 2-21 | A |
| 2-22 | A |
| 2-65 | B |
| 2-91 | A |
| 2-95 | A |
| 2-97 | A |
| 2-98 | A |
| 2-102 | A |

TABLE 63-continued

| Comp. No. | Evaluation |
|---|---|
| 2-106 | A |
| 2-107 | A |
| 2-109 | A |
| 2-110 | A |
| 2-111 | A |
| 2-112 | A |
| 2-113 | A |
| 2-114 | A |

TABLE 64

| Comp. No. | Evaluation |
|---|---|
| 2-121 | A |
| 2-122 | A |
| 2-123 | A |
| 2-124 | A |
| 2-126 | A |
| 2-130 | A |
| 2-164 | A |
| 2-166 | A |
| 2-183 | A |
| 2-184 | A |
| 2-185 | A |
| 2-186 | A |
| 2-187 | A |
| 2-188 | A |
| 2-189 | A |
| 2-190 | A |
| 2-191 | A |
| 2-192 | A |
| 2-193 | A |
| 2-194 | A |
| 2-201 | A |
| 2-202 | A |
| 2-203 | A |
| 2-204 | A |
| 2-205 | A |
| 2-206 | A |
| 2-207 | A |
| 2-208 | A |
| 2-215 | A |
| 2-216 | A |
| 2-220 | A |
| 2-223 | A |

TABLE 65

| Comp. No. | Evaluation |
|---|---|
| 2-226 | B |
| 2-244 | A |
| 2-245 | A |
| 2-246 | A |
| 2-247 | A |
| 2-248 | A |
| 2-249 | A |
| 2-251 | A |
| 2-257 | A |
| 2-266 | A |
| 2-268 | A |
| 2-277 | A |
| 2-280 | A |
| 2-284 | A |
| 2-288 | A |
| 2-290 | A |
| 2-299 | A |
| 2-300 | A |
| 2-328 | B |

TABLE 65-continued

| Comp. No. | Evaluation |
|---|---|
| 2-331 | A |
| 2-332 | A |
| 2-333 | A |
| 2-334 | A |
| 2-343 | A |
| 2-344 | A |
| 2-346 | A |
| 2-365 | A |
| 2-412 | A |
| 2-448 | A |
| 2-450 | A |
| 2-451 | B |
| 2-453 | A |

TABLE 66

| Comp. No. | Evaluation |
|---|---|
| 2-455 | A |
| 2-461 | A |
| 2-465 | A |
| 2-551 | A |
| 3-1 | A |
| 3-5 | A |
| 3-6 | A |
| 3-7 | A |
| 3-16 | A |
| 3-17 | A |
| 3-18 | A |
| 3-21 | A |
| 3-26 | A |
| 3-28 | A |
| 3-30 | B |
| 3-32 | B |
| 3-51 | A |
| 3-55 | A |
| 3-57 | A |
| 3-66 | A |
| 3-107 | B |
| 4-22 | A |
| 4-199 | A |
| 4-201 | A |
| 6-1 | A |

TEST EXAMPLE 3

Test for Preventive Effect on Wheat Powdery Mildew 9 wheat seeds (variety: Norin-61-go) were sown in each 9 cm×9 cm polyvinyl chloride pot, grown in a greenhouse for 8 days, then treated with 10 ml per pot of aqueous solutions of wettable powders prepared in accordance with Formulation Example 2, at a concentration of 500 ppm in terms of the active ingredients and dried in the air. Then, the seedlings were inoculated with *Ervsiphe graminis* spores in suspension and placed in a greenhouse at 25 to 30° C. 10 days after the inoculation, the total diseases area of the first leaves in each pot was observed and evaluated on the basis of the standards shown in Table 59. The results are shown in Tables 67 to 71.

TABLE 67

| Comp. No. | Evaluation |
|---|---|
| 1-1 | A |
| 1-2 | A |

TABLE 67-continued

| Comp. No. | Evaluation |
|---|---|
| 1-3 | A |
| 1-4 | B |
| 1-6 | A |
| 1-7 | A |
| 1-10 | A |
| 1-11 | A |
| 1-12 | A |
| 1-13 | A |
| 1-14 | B |
| 1-17 | B |
| 1-18 | A |
| 1-33 | A |
| 1-34 | A |
| 1-35 | A |
| 1-40 | A |
| 1-41 | A |
| 1-42 | B |
| 1-72 | A |
| 1-118 | A |
| 1-119 | A |
| 1-120 | A |
| 1-122 | A |
| 1-125 | A |
| 1-146 | B |
| 1-148 | B |
| 1-150 | B |
| 1-163 | A |
| 1-165 | B |
| 1-166 | B |
| 1-168 | A |

TABLE 68

| Comp. No. | Evaluation |
|---|---|
| 1-178 | A |
| 1-192 | A |
| 1-193 | B |
| 1-194 | A |
| 1-195 | A |
| 1-198 | A |
| 1-201 | A |
| 1-202 | A |
| 1-264 | A |
| 1-266 | A |
| 1-275 | A |
| 1-277 | A |
| 2-1 | A |
| 2-17 | B |
| 2-21 | B |
| 2-22 | B |
| 2-91 | A |
| 2-95 | A |
| 2-97 | A |
| 2-98 | A |
| 2-102 | A |
| 2-106 | A |
| 2-107 | A |
| 2-109 | A |
| 2-110 | B |
| 2-111 | B |
| 2-112 | B |
| 2-113 | A |
| 2-114 | A |
| 2-121 | A |
| 2-122 | A |
| 2-123 | A |

TABLE 69

| Comp. No. | Evaluation |
|---|---|
| 2-126 | B |
| 2-164 | A |
| 2-166 | A |
| 2-183 | B |
| 2-184 | B |
| 2-185 | B |
| 2-186 | B |
| 2-187 | A |
| 2-188 | A |
| 2-189 | A |
| 2-190 | A |
| 2-191 | A |
| 2-192 | B |
| 2-193 | A |
| 2-194 | A |
| 2-201 | A |
| 2-202 | B |
| 2-203 | A |
| 2-204 | A |
| 2-205 | A |
| 2-206 | B |
| 2-207 | A |
| 2-208 | A |
| 2-215 | B |
| 2-216 | B |
| 2-220 | B |
| 2-223 | B |
| 2-244 | B |
| 2-245 | A |
| 2-246 | B |
| 2-247 | A |
| 2-249 | A |

TABLE 70

| Comp. No. | Evaluation |
|---|---|
| 2-251 | B |
| 2-266 | A |
| 2-268 | B |
| 2-277 | A |
| 2-280 | A |
| 2-284 | A |
| 2-288 | A |
| 2-290 | B |
| 2-299 | A |
| 2-300 | A |
| 2-328 | B |
| 2-331 | B |
| 2-332 | B |
| 2-333 | B |
| 2-334 | B |
| 2-343 | B |
| 2-346 | A |
| 2-365 | B |
| 2-412 | A |
| 2-448 | A |
| 2-450 | A |
| 2-453 | A |
| 2-455 | B |
| 2-461 | A |
| 2-465 | A |
| 2-551 | B |
| 3-1 | B |
| 3-5 | B |
| 3-6 | A |
| 3-7 | A |
| 3-16 | A |
| 3-17 | A |

TABLE 71

| Comp. No. | Evaluation |
|---|---|
| 3-18 | A |
| 3-21 | B |
| 3-26 | B |
| 3-28 | B |
| 3-30 | B |
| 3-32 | B |
| 3-41 | B |
| 3-42 | B |
| 3-57 | B |
| 3-80 | A |
| 3-101 | B |
| 3-105 | B |
| 3-107 | B |
| 4-22 | A |
| 4-199 | A |
| 4-201 | B |
| 6-1 | B |

TEST EXAMPLE 4
Test for Preventive Effect on Rice Blast 15 rice seeds (variety: Aichi-asahi) were sown in each unglazed pot of 7 cm in diameter and grown in a greenhouse for 2 to 3 weeks. The rice seedlings with completely developed 4th leaves were treated 10 ml per pot of aqueous solutions of wettable powders prepared in accordance with Formulation Example 2, at a concentration of 500 ppm in terms of the active ingredients and dried in the air. Then, the seedlings were inoculated with Pyricularia oryzae spores in suspension by spraying and immediately placed in a moist chamber at 25° C. for 24 hours. Thereafter, the seedlings were placed in a greenhouse. 5 days after the inoculation, the spotty lesions on the 4th leaves were counted, and the preventive values were calculated in accordance with numerical expression 1 and evaluated on the basis of the standards shown in Table 72. The results are shown in Tables 73 to 75.

Preventive value (%) = (Numerical expression 1)

$$\left(1 - \frac{\text{Number of lesions in treated area}}{\text{Number of lesions in untreated area}}\right) \times 100$$

TABLE 72

| Evaluation | Preventive value |
|---|---|
| A | 100% |
| B | Less than 100% but at least 80.0% |
| C | Less than 80.0% but at least 50.0% |
| D | Less than 50.0% |

TABLE 73

| Comp. No. | Evaluation |
|---|---|
| 1-1 | A |
| 1-2 | A |
| 1-3 | B |
| 1-6 | A |
| 1-10 | A |

TABLE 73-continued

| Comp. No. | Evaluation |
|---|---|
| 1-12 | A |
| 1-13 | B |
| 1-14 | B |
| 1-17 | B |
| 1-18 | B |
| 1-33 | B |
| 1-34 | B |
| 1-118 | B |
| 1-120 | B |
| 1-125 | B |
| 1-146 | B |
| 1-147 | B |
| 1-148 | B |
| 1-150 | B |
| 1-163 | A |
| 1-165 | A |
| 1-166 | B |
| 1-168 | B |
| 1-178 | A |
| 1-188 | B |
| 1-192 | B |
| 1-193 | B |
| 1-194 | B |
| 1-195 | B |
| 1-198 | B |
| 1-201 | B |
| 1-202 | B |

TABLE 74

| Comp. No. | Evaluation |
|---|---|
| 1-266 | B |
| 1-275 | A |
| 2-1 | B |
| 2-17 | B |
| 2-97 | B |
| 2-102 | B |
| 2-106 | A |
| 2-109 | B |
| 2-110 | B |
| 2-111 | A |
| 2-112 | B |
| 2-113 | A |
| 2-114 | B |
| 2-121 | B |
| 2-164 | B |
| 2-166 | A |
| 2-183 | A |
| 2-184 | A |
| 2-185 | B |
| 2-186 | A |
| 2-187 | B |
| 2-188 | A |
| 2-189 | B |
| 2-190 | A |
| 2-192 | B |
| 2-193 | A |
| 2-194 | B |
| 2-196 | B |
| 2-201 | B |
| 2-202 | B |
| 2-203 | B |
| 2-204 | B |

TABLE 75

| Comp. No. | Evaluation |
|---|---|
| 2-205 | B |
| 2-206 | B |
| 2-207 | B |
| 2-208 | B |
| 2-215 | B |
| 2-220 | B |
| 2-226 | B |
| 2-244 | B |
| 2-246 | A |
| 2-247 | B |
| 2-248 | A |
| 2-249 | B |
| 2-251 | A |
| 2-277 | B |
| 2-284 | A |
| 2-288 | A |
| 2-290 | B |
| 2-300 | B |
| 2-328 | B |
| 2-346 | B |
| 2-412 | B |
| 2-448 | B |
| 2-451 | B |
| 2-461 | A |
| 3-1 | A |
| 3-6 | B |
| 3-16 | B |
| 3-17 | B |
| 3-57 | B |
| 3-101 | B |
| 4-22 | A |
| 4-201 | A |
| 6-1 | B |

TEST EXAMPLE 5

Test for Preventive Effect on Cucumber Gray Mold 9 cucumber seeds (variety: Sagami-hanziro) were sown in each 9 cm–9 cm polyvinyl chloride pot and grown in a greenhouse for 7 days. The cotyledonary cucumber seedlings were treated with 10 ml per pot of aqueous solutions of wettable powders prepared in accordance with Formulation Example 2, at a concentration of 500 ppm in terms of the active ingredients, and dried in the air. Then, the seedlings were inoculated with milled *Botrytis cinerea* hyphae in solution by spraying and immediately placed in a moist chamber at 22° C. 3 days after the inoculation, the total diseased area in each pot was observed and evaluated on the basis of the standards shown in Table 59. The results are shown in Tables 76 to 77.

TABLE 76

| Comp. No. | Evaluation |
|---|---|
| 1-4 | A |
| 1-11 | B |
| 1-12 | A |
| 1-35 | B |
| 1-42 | B |
| 1-298 | A |
| 2-65 | B |
| 2-111 | B |
| 2-122 | A |
| 2-189 | B |
| 2-190 | A |
| 2-191 | A |
| 2-193 | A |
| 2-204 | B |

TABLE 76-continued

| Comp. No. | Evaluation |
|---|---|
| 2-205 | A |
| 2-207 | A |
| 2-215 | B |
| 2-216 | B |
| 2-226 | A |
| 2-246 | B |
| 2-247 | B |
| 2-248 | A |
| 2-249 | B |
| 2-257 | B |
| 2-268 | B |
| 2-288 | B |
| 2-300 | A |
| 2-331 | A |
| 2-332 | B |
| 2-334 | A |
| 2-343 | B |
| 2-346 | B |

TABLE 77

| Comp. No. | Evaluation |
|---|---|
| 2-448 | A |
| 2-450 | A |
| 2-453 | A |
| 2-455 | B |
| 2-551 | B |
| 3-5 | B |
| 3-28 | B |
| 3-30 | B |
| 3-51 | B |
| 3-55 | A |
| 3-57 | A |
| 3-66 | A |

TEST EXAMPLE 6

Test for Preventive Effect on Rice Sheath Blight 15 rice seeds (variety: Kinmaze) were sown in each unglazed pot of 7 cm in diameter and grown in a greenhouse for 4 to 5 weeks. The rice seedlings with completely developed 5th leaves were treated 10 ml per pot of aqueous solutions of wettable powders prepared in accordance with Formulation Example 2, at a concentration of 500 ppm in terms of the active ingredients and dried in the air. Then, the roots of the seedlings were inoculated with *Rhizoctonia solani* grown in a chaff bran medium, and the seedlings were immediately placed in a moist chamber at 28° C. 6 days later, the heights of the lesions on the leaf sheaths were measured, and the preventive values were calculated in accordance with numerical expression 2 and evaluated on the basis of the standards shown in Table 72. The results are shown in Tables 78 to 79.

$$\text{Preventive value } (\%) = \left(1 - \frac{\text{Height of lesions in treated area}}{\text{Height of lesions in untreated area}}\right) \times 100 \quad \text{(Numerical expression 2)}$$

TABLE 78

| Comp. No. | Evaluation |
| --- | --- |
| 1-10 | B |
| 1-11 | B |
| 1-13 | B |
| 1-14 | B |
| 1-34 | A |
| 1-35 | B |
| 1-119 | B |
| 1-120 | A |
| 1-122 | B |
| 1-125 | B |
| 1-137 | B |
| 1-178 | B |
| 2-98 | B |
| 2-102 | A |
| 2-107 | B |
| 2-109 | B |
| 2-110 | B |
| 2-111 | B |
| 2-112 | B |
| 2-113 | B |
| 2-114 | A |
| 2-121 | A |
| 2-122 | B |
| 2-126 | B |
| 2-166 | A |
| 2-190 | B |
| 2-194 | B |
| 2-196 | B |
| 2-201 | B |
| 2-205 | A |
| 2-206 | B |
| 2-244 | B |

TABLE 79

| Comp. No. | Evaluation |
| --- | --- |
| 2-247 | B |
| 2-249 | B |
| 2-251 | B |
| 2-277 | B |
| 2-412 | B |
| 2-450 | B |
| 3-6 | B |
| 3-16 | B |
| 3-21 | B |

What is claimed is:

1. A biarylalkylenecarbamic acid derivative represented by formula (I):

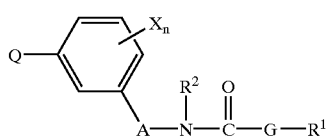

(I)

wherein X is a halogen atom, a $(C_1-C_6)$ alkyl group, a $(C_1-C_6)$ alkoxy group, a $(C_1-C_4)$ haloalkyl group or a $(C_1-C_4)$ haloalkoxy group, n is 0 or an integer of from 1 to 4, $R^1$ is a $(C_1-C_6)$ alkyl group, a $(C_2-C_6)$ alkenyl group, a $(C_2-C_6)$ alkynyl group, a $(C_3-C_6)$ cycloalkyl group or a $(C_1-C_4)$ haloalkyl group, $R^2$ is a hydrogen atom, a $(C_1-C_6)$ alkyl group, a $(C_2-C_6)$ alkenyl group, a $(C_2-C_6)$ alkynyl group, a $(C_1-C_4)$ alkoxy group, a $(C_1-C_6)$ alkoxy $(C_1-C_4)$ alkyl group, a $(C_1-C_6)$ alkylthio $(C_1-C_4)$ alkyl group, a $(C_1-C_4)$ haloalkyl group, a $(C_1-C_6)$ alkylcarbonyl group, a phenylcarbonyl group, a $(C_1-C_4)$ alkoxycarbonyl group or an aryl $(C_1-C_4)$ alkyl group which may be substituted with a halogen atom, a $(C_1-C_3)$ alkyl group or a $(C_1-C_3)$ alkoxy group, A is a $(C_1-C_7)$ alkylene group which may be branched, G is an oxygen atom, a sulfur atom or a group —$NR^3$— wherein $R^3$ is a hydrogen atom or a $(C_1-C_4)$ alkyl group and when $R^3$ is a hydrogen atom $R^1$ is a $(C_2-C_6)$ alkenyl group, a $(C_2-C_6)$ alkynyl group or a $(C_1-C_4)$ haloalkyl group, and Q is a group represented by formula:

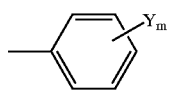

(A-1)

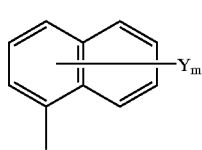

(A-2)

or

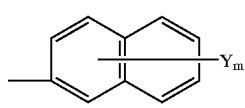

(A-3)

wherein Y is a halogen atom, nitro, cyano, hydroxy, a $(C_1-C_6)$ alkyl group, a $(C_2-C_6)$ alkenyl group, a $(C_2-C_6)$ alkynyl group, a $(C_3-C_6)$ cycloalkyl group, a $(C_3-C_6)$ cycloalkyl $(C_1-C_4)$ alkyl group, a $(C_1-C_6)$ alkoxy group, a $(C_2-C_6)$ alkenyloxy group, a $(C_2-C_6)$ alkynyloxy group, a $(C_3-C_6)$ cycloalkoxy group, a $(C_1-C_6)$ alkylthio group, a $(C_1-C_6)$ alkylsulfinyl group, a $(C_1-C_6)$ alkylsulfonyl group, a $(C_1-C_4)$ alkoxy $(C_1-C_4)$ alkyl group, a $(C_1-C_4)$ alkylthio $(C_1-C_4)$ alkyl group, a $(C_1-C_4)$ haloalkyl group, a $(C_1-C_4)$ haloalkoxy group, a $(C_1-C_4)$ haloalkylthio group, a $(C_1-C_4)$ haloalkylsulfinyl group, a $(C_1-C_4)$ haloalkylsulfonyl group, a $(C_1-C_4)$ alkylcarbonyl group, a $(C_1-C_4)$ alkoxycarbonyl group, a group —$CONR^4R^5$ wherein $R^4$ and $R^5$ may be the same or different, are hydrogen atoms or $(C_1-C_4)$ alkyl groups, an amino group, a mono($C_1-C_4$) alkylamino group, a di $(C_1-C_4)$ alkylamino group, a $(C_1-C_4)$ alkylcarbonylamino group, an aryl group which may be substituted with a halogen atom, a $(C_1-C_4)$ alkyl group or a $(C_1-C_4)$ alkoxy group, an aryloxy group which may be substituted with a halogen atom, a $(C_1-C_4)$ alkyl group or a $(C_1-C_4)$ alkoxy group, an aryl $(C_1-C_4)$ alkoxy group which may be substituted with a halogen atom, a $(C_1-C_4)$ alkyl group or a $(C_1-C_4)$ alkoxy group, or may form a methylenedioxy group together with an adjacent Y, and m is 0 or an integer of from 1 to 5.

2. An agricultural and horticultural fungicide containing the biarylalkylenecarbamic acid derivative according to claim 1 as an active ingredient.

3. The biarylalkylenecarbamic acid derivative as claimed in claim 1, wherein the halogen atom is selected from the group consisting of fluorine, chlorine, bromine, and iodine.

4. The biarylalkylenecarbamic acid derivative as claimed in claim 1, wherein said derivative is methyl N-(3-phenylbenzyl)carbamate.

5. The biarylalkylenecarbamic acid derivative as claimed in claim 1, wherein said derivative is isopropyl N-(3-phenylbenzyl)carbamate.

6. The biarylalkylenecarbamic acid derivative as claimed in claim 1, wherein said derivative is methyl N-(3-phenylbenzyl)-N-(2-propynyl)carbamate.

7. The biarylalkylenecarbamic acid derivative as claimed in claim 1, wherein said derivative is methyl N-methoxymethyl-N-(3-phenylbenzyl)carbamate.

8. The biarylalkylenecarbamic acid derivative as claimed in claim 1, wherein said derivative is methyl N-(2-methyl-3-phenylbenzyl)carbamate.

9. The biarylalkylenecarbamic acid derivative as claimed in claim 1, wherein said derivative is methyl N-{1-[3-(4-methoxyphenyl)phenyl]ethyl}carbamate.

10. The biarylalkylenecarbamic acid derivative as claimed in claim 1, wherein said derivative is methyl N-methoxy-N-(2-methyl-3-phenylbenzyl)carbamate.

11. The fungicide as claimed in claim 2, further comprising a component selected from the group consisting of an inert liquid, a solid carrier, a surfactant and combinations thereof.

12. The fungicide claimed in claim 11, wherein the solid carrier is selected from the group consisting of talc, bentonite, clay, kaolin, diatomaceous earth, white carbon, vermiculite, slaked lime, silica sand, urea and ammonium sulfate.

13. The fungicide claimed in claim 11, wherein the inert liquid is selected from the group consisting of isopropyl alcohol, xylene, cyclohexanone and methylnaphthalene.

14. The fungicide claimed in claim 11, wherein the surfactant is selected from the group consisting of alcohol sulfuric acid ester salts, alkylarylsulfonates, lignin sulfonate, polyoxyethylene glycol ether, polyoxyethylene alkyl aryl ethers and polyoxyethylene sorbitan monoalkylate.

15. The fungicide as claimed in claim 11, wherein said fungicide comprises from 0.1 to 20% by weight of the biarylalkylenecarbamic acid derivative.

16. A method comprising applying the fungicide as claimed in claim 2 to a plant, a soil or a submerged object.

17. The method as claim in claim 16, wherein the fungicide prevents plant diseases caused by Oomycetes, Ascomycetes, Deuteromycetes or Basidiomycetes.

18. The method as claimed in claim 16, wherein the fungicide is applied in combination with another fungicide, an insecticide, herbicide, plant growth regulator or fertilizer.

19. A fungicide comprising 2% of the biarylalkylalkylenecarbamic acid derivative of formula (I) claimed in claim 1, wherein Q is $4\text{-}CF_3C_6H_4$, A is $CH_2$, $R^2$ is a hydrogen atom, G is O, and $R^1$ is $CH_3$, 5% diatomaceous earth, and 93% clay.

20. A fungicide comprising 50% of the biarylalkylalkylenecarbamic acid derivative of formula (I) claimed in claim 1, wherein Q is $4\text{-}CH_3C_6H_4$, A is $CH_2$, $R^2$ is a hydrogen atom, G is O, and $R^1$ is $CH_3$, 45% diatomaceous earth, 2% sodium dinaphthylmethanedisulfonate, and 3% sodium lignin sulfonate.

* * * * *